US012440639B2

(12) United States Patent
Tan et al.

(10) Patent No.: US 12,440,639 B2
(45) Date of Patent: Oct. 14, 2025

(54) POSITIONING AND STABILISING STRUCTURE FOR A PATIENT INTERFACE

(71) Applicant: ResMed Asia Pte. Ltd., Singapore (SG)

(72) Inventors: Beng Hai Tan, Singapore (SG); Wai Hoong Leng, Singapore (SG)

(73) Assignee: ResMed Asia Pte. Ltd., Singapore (SG)

(*) Notice: Subject to any disclaimer, the term of this patent is extended or adjusted under 35 U.S.C. 154(b) by 854 days.

(21) Appl. No.: 17/623,513

(22) PCT Filed: Jun. 24, 2020

(86) PCT No.: PCT/IB2020/055965
§ 371 (c)(1),
(2) Date: Dec. 28, 2021

(87) PCT Pub. No.: WO2020/261137
PCT Pub. Date: Dec. 30, 2020

(65) Prior Publication Data

US 2022/0395657 A1 Dec. 15, 2022

(30) Foreign Application Priority Data

Jun. 28, 2019 (AU) ................................ 2019902272

(51) Int. Cl.
*A61M 16/06* (2006.01)
*A61M 16/00* (2006.01)

(52) U.S. Cl.
CPC .... *A61M 16/0683* (2013.01); *A61M 16/0066* (2013.01); *A61M 16/0616* (2014.02);
(Continued)

(58) Field of Classification Search
CPC .. A61M 16/00; A61M 16/0003; A61M 16/06; A61M 16/0683; A61M 16/0694;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

AU 2007100084 A 3/2007
CN 102933245 A 2/2013
(Continued)

OTHER PUBLICATIONS

Office Action dated Sep. 12, 2023 issued in Chinese Application No. 202080047014.2 with English translation (20 pages).
(Continued)

*Primary Examiner* — Colin W Stuart
(74) *Attorney, Agent, or Firm* — Nixon & Vanderhye P.C.

(57) ABSTRACT

A positioning and stabilising structure for a full-face mask of a patient interface comprises a superior strap portion, an inferior strap portion, and two anterior strap portions. Each anterior strap portion having a generally triangular surface with a first width and a second width that is less than the first width and disposed more anterior while in use. The superior strap portion and the inferior strap portion are each connected to or formed integrally with each anterior strap portion at a respective corner of the generally triangular surface. Each anterior strap portion is connected or connectable to a connection portion that engages the plenum chamber. The connection portion is releasably engageable from the plenum chamber. The superior strap portion and the inferior strap portion are joined to the anterior strap portions anterior to the patient's ears, when in use.

20 Claims, 49 Drawing Sheets

(52) U.S. Cl.
CPC ............... *A61M 2016/0661* (2013.01); *A61M 2205/0216* (2013.01)

(58) Field of Classification Search
CPC .......... A61M 16/0688; A61M 16/0616; A61M 2016/0661; A61M 2205/0216; A62B 18/084
See application file for complete search history.

(56) References Cited

U.S. PATENT DOCUMENTS

| | | | | |
|---|---|---|---|---|
| 6,123,082 | A | 9/2000 | Berthon-Jones | |
| 6,470,886 | B1 * | 10/2002 | Jestrabek-Hart | A61M 16/0633 128/207.11 |
| 6,532,959 | B1 | 3/2003 | Berthon-Jones | |
| 6,581,594 | B1 | 6/2003 | Drew et al. | |
| 7,225,811 | B2 | 6/2007 | Ruiz | |
| 7,866,944 | B2 | 1/2011 | Kenyon et al. | |
| 7,877,817 | B1 * | 2/2011 | Ho | A61M 16/0633 2/452 |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 9,981,104 | B1 * | 5/2018 | Groll | A61M 16/0694 |
| 10,369,319 | B2 | 8/2019 | Formica et al. | |
| 10,576,234 | B2 | 3/2020 | Brown | |
| 2004/0112377 | A1 * | 6/2004 | Amarasinghe | A61M 16/0666 128/207.11 |
| 2008/0190432 | A1 | 8/2008 | Blochlinger et al. | |
| 2009/0044808 | A1 | 2/2009 | Guney et al. | |
| 2009/0050156 | A1 | 2/2009 | Ng et al. | |
| 2010/0000534 | A1 | 1/2010 | Kooij et al. | |
| 2010/0258133 | A1 * | 10/2010 | Todd | A61M 16/0858 128/207.12 |
| 2012/0037161 | A1 | 2/2012 | Ging et al. | |
| 2012/0199131 | A1 | 8/2012 | Sofranko | |
| 2013/0324788 | A1 | 12/2013 | Holley | |
| 2014/0190486 | A1 * | 7/2014 | Dunn | A61M 16/0683 128/205.25 |
| 2014/0305439 | A1 | 10/2014 | Koninklijke et al. | |
| 2016/0038708 | A1 | 2/2016 | Amarasinghe | |
| 2016/0045700 | A1 * | 2/2016 | Amarasinghe | A61M 16/0683 128/205.25 |
| 2016/0067441 | A1 | 3/2016 | Bearne et al. | |
| 2016/0082214 | A1 * | 3/2016 | Barlow | A61M 16/0622 128/206.24 |
| 2016/0144144 | A1 | 5/2016 | Smith et al. | |
| 2016/0250426 | A1 | 9/2016 | Koninklijke | |
| 2016/0250436 | A1 | 9/2016 | Brown et al. | |
| 2016/0367780 | A1 | 12/2016 | Ging et al. | |
| 2017/0209661 | A1 | 7/2017 | Amarasinghe | |
| 2017/0259021 | A1 * | 9/2017 | Frater | A61M 16/0694 |
| 2017/0304576 | A1 | 10/2017 | Koninklijke et al. | |
| 2017/0304577 | A1 | 10/2017 | Bearne et al. | |
| 2018/0161535 | A1 | 6/2018 | Henry et al. | |
| 2018/0214655 | A1 | 8/2018 | Kooij et al. | |
| 2018/0243522 | A1 | 8/2018 | Ng et al. | |
| 2019/0105455 | A1 | 4/2019 | Ng et al. | |

FOREIGN PATENT DOCUMENTS

| | | | |
|---|---|---|---|
| CN | 105339031 | A | 2/2016 |
| CN | 108463264 | A | 8/2018 |
| WO | WO 98/004310 | A1 | 2/1998 |
| WO | WO 98/034665 | A1 | 8/1998 |
| WO | WO 2000/078381 | A1 | 12/2000 |
| WO | 2004/073777 | A1 | 9/2004 |
| WO | WO 2004/073778 | A1 | 9/2004 |
| WO | WO 2005/063328 | A1 | 7/2005 |
| WO | WO 2006/074513 | A1 | 7/2006 |
| WO | WO 2006/130903 | A1 | 12/2006 |
| WO | WO 2009/052560 | A1 | 4/2009 |
| WO | WO 2010/135785 | A1 | 12/2010 |
| WO | 2011/121466 | A1 | 10/2011 |
| WO | 2012/040791 | A1 | 4/2012 |
| WO | 2012/045127 | A1 | 4/2012 |
| WO | WO 2012/171072 | A1 | 12/2012 |
| WO | WO 2013/020167 | A1 | 2/2013 |
| WO | 2014/175753 | A1 | 10/2014 |
| WO | 2015/079396 | A1 | 6/2015 |
| WO | WO 2017/158476 | A2 | 9/2017 |
| WO | 2019/111135 | A1 | 6/2019 |

OTHER PUBLICATIONS

"*Respiratory Physiology*", by John B. West, Lippincott Williams & Wilkins, 9th edition published 2012 (8 pages).
International Search Report mailed Aug. 21, 2020 issued in International Application No. PCT/IB2020/055966 (9 pages).
Written Opinion mailed Aug. 21, 2020 issued in International Application No. PCT/IB2020/055966 (6 pages).
International Search Report mailed Sep. 4, 2020 issued in International Application No. PCT/IB2020/055965 (10 pages).
Written Opinion mailed Sep. 4, 2020 issued in International Application No. PCT/IB2020/055965 (6 pages).
Office Action dated Aug. 25, 2022 issued in U.S. Appl. No. 17/623,551 (24 pages).
Extended European Search Report dated Jun. 21, 2023 issued in European Application No. 20831235.5 (8 pages).
International Preliminary Report on Patentability dated Dec. 28, 2021 issued in PCT/IB2020/055966 (7 pages).
International Preliminary Report on Patentability dated Dec. 28, 2021 issued in PCT/IB2020/055965 (7 pages).

* cited by examiner

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2015 ResMed Limited

Copyright 2015 ResMed Limited

Copyright 2015 ResMed Limited

Right-hand helix
Right-hand positive

Copyright 2015 ResMed Limited

POSITIONING AND STABILISING STRUCTURE FOR A PATIENT INTERFACE

1 CROSS-REFERENCE TO RELATED APPLICATIONS

This application is the U.S. national phase of International Application No. PCT/IB2020/055965 filed Jun. 24, 2020 which designated the U.S. and claims priority to Australian Provisional Patent Application No. 2019902272 filed Jun. 28, 2019, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT' LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT' FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

2.2.3.4 Data Management

There may be clinical reasons to obtain data to determine whether the patient prescribed with respiratory therapy has been “compliant”, e.g. that the patient has used their RPT device according to one or more “compliance rules”. One example of a compliance rule for CPAP therapy is that a patient, in order to be deemed compliant, is required to use the RPT device for at least four hours a night for at least 21 of 30 consecutive days. In order to determine a patient’s compliance, a provider of the RPT device, such as a health care provider, may manually obtain data describing the patient’s therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient’s therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient’s teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient’s mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient’s SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient’s condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

An aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a positioning and stabilising structure for a full-face mask of a patient interface, the positioning and stabilising structure comprising:

- a superior strap portion;
- an inferior strap portion; and
- two anterior strap portions, each connected to or formed integrally with the superior strap portion and the inferior strap portion, each anterior strap portion connected or connectable to a connection portion which engages an interfacing portion of the patient interface; and wherein the superior strap portion and the inferior strap portion join the anterior strap portions anterior to the patient's ears, in use.

Another form of the present technology comprises a patient interface comprising a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilising structure for a full-face, the positioning and stabilising structure comprising:

a superior strap portion;

an inferior strap portion; and an anterior strap portions, each having a generally triangular surface with a first width and a second width being less than the first width and disposed more anterior while in use, the superior strap portion and the inferior strap portion each connected to or formed integrally with each anterior strap portion at a respective corner of the generally triangular surface, the anterior strap portion connected or connectable to a connection portion which engages the plenum chamber, the connection portion being releasably engageable from the plenum chamber; and wherein the superior strap portion and the inferior strap portion join the anterior strap portions anterior to the patient's ears, in use; and wherein the anterior strap portion forms a loop when connected with the connection portion, the loop is adjustable to adjust the direction and magnitude of a headgear vector.

In examples: a) the superior strap portion is configured to overlie the parietal bone of the patient's skull; and/or b) the inferior strap portion is configured to overlie or lie inferior to the occipital bone of the patient's skull.

Another form of the present technology comprises a positioning and stabilising structure for a patient interface, the positioning and stabilising structure comprising:

a superior strap portion;

an inferior strap portion;

at least one anterior strap portion connected to or formed integrally with the superior strap portion and the inferior strap portion;

the anterior strap portion comprising a strap receiving portion and a strap attachment portion which is releasably connectable to the strap receiving portion such that the anterior strap portion forms a loop, wherein in use the loop engages a connection portion which engages an interfacing portion of the patient interface;

wherein the strap receiving portion is configured to engage the strap attachment portion in a selected one of a plurality of possible positions, wherein the plurality of possible positions comprises a plurality of possible angular positions of the strap attachment portion relative to the strap receiving portion.

Another form of the present technology is a patient interface that comprises a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilising structure for a patient interface, the positioning and stabilising structure comprising:

a superior strap portion;

an inferior strap portion;

at least one anterior strap portion connected to or formed integrally with the superior strap portion and the inferior strap portion;

the anterior strap portion comprising a strap receiving portion and a strap attachment portion which is releasably connectable to the strap receiving portion such that the anterior strap portion forms a loop, wherein in use the loop engages a connection portion which engages the plenum chamber;

wherein the strap receiving portion is configured to engage the strap attachment portion in a selected one of a plurality of possible positions, wherein the plurality of possible positions comprises a plurality of possible angular positions of the strap attachment portion relative to the strap receiving portion, and wherein the strap attachment portion is connected completely within the boundary of the strap receiving portion in any one of the plurality of possible positions, and wherein the angle between the strap attachment portion and the strap receiving portion when connected is configured to cause pivotable movement in the plenum chamber and/or the seal forming structure.

In examples: a) the superior strap portion and the inferior strap portion join the anterior strap portion anterior to the patient's ear, in use; b) the connection portion is releasably engageable with the interfacing portion; c) the superior strap portion is configured to overlie the parietal bone of the patient's skull; and/or d) the inferior strap portion is configured to overlie or lie inferior to the occipital bone of the patient's skull.

Another form of the present technology comprises a positioning and stabilising structure for a patient interface, the positioning and stabilising structure comprising:

a superior strap portion;

an inferior strap portion;

at least one anterior strap portion connected to or formed integrally with the superior strap portion and the inferior strap portion;

the anterior strap portion comprising a strap receiving portion and a strap attachment portion which is releasably connectable to the strap receiving portion such that the anterior strap portion forms a loop, wherein in use the loop engages a connection portion which engages an interfacing portion of the patient interface;

wherein the strap receiving portion is configured to engage the strap attachment portion in a selected one of a plurality of possible positions to adjust the direction and magnitude of the headgear vector.

Another form of the present technology is a patient interface that comprises a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilising structure for a patient interface, the positioning and stabilising structure comprising:

a superior strap portion;

an inferior strap portion;

at least one anterior strap portion connected to or formed integrally with the superior strap portion and the inferior strap portion;

the anterior strap portion comprising a strap receiving portion and a strap attachment portion which is releasably engageable from the strap receiving portion such that the anterior strap portion forms a loop, wherein in use the loop engages a connection portion which engages the plenum chamber;

wherein the strap receiving portion is configured to engage the strap attachment portion in a selected one of a plurality of possible positions to adjust the direction and magnitude of the headgear vector, and wherein the headgear vector is configured to cause pivotable movement in the plenum chamber and/or seal forming structure.

In examples: a) the superior strap portion and the inferior strap portion join the anterior strap portion anterior to the patient's ear, in use; b) the superior strap portion is configured to overlie the parietal bone of the patient's skull; c) the inferior strap portion is configured to overlie or lie inferior to the occipital bone of the patient's skull; d) the width of the strap receiving portion decreases from a posterior end to an anterior end thereof, and wherein the width of the strap receiving portion is not narrower than the strap attachment portion between the posterior end and the anterior end; e) the strap attachment portion comprises a hook material; f) the strap receiving portion comprises a patient facing surface and an opposite non-patient facing surface, wherein the non-patient facing surface is provided with an unbroken loop material to engage the hook material of the strap attachment portion; g) the connection portion is releasably connectable to the interfacing portion; h) the anterior strap portion passes through a slot of the connection portion; i) the connection portion attaches to a frame which connects to a cushion module of the plenum chamber; j) the connection portion attaches to a cushion module; k) at least a part of the anterior strap portion is configured to overlie the cheek area of the patient's face; l) the superior strap portion, inferior strap portion and anterior strap portions are integrally formed from a single piece of material; m) the superior strap portion bifurcates into a first strap portion which overlies a superior surface of the patient's parietal bone and a second strap portion which overlies a posterior surface of the patient's parietal bone; n) the superior strap portion is joined to the inferior strap portion by posterior connecting strap portions; and/or o) the superior strap portion and the posterior connecting strap portions form a substantially loop shape; p) a maximum width of the strap receiving portion is approximately two to approximately two to approximately four times wider than the maximum width of the strap attachment portion; q) an angle between the strap attachment portion and the strap receiving portion when connected is configured to cause movement in a cushion module coupled to the connection portion; r) a superior portion of the cushion module is configured to move in the posterior direction when the strap attachment portion is substantially parallel to the inferior strap portion; s) a superior portion of the cushion module is configured to move in the anterior direction when the strap attachment portion is aligned with the superior strap portion; and/or t) the anterior strap portion has a generally triangular surface with a first width and a second width being less than the first width and disposed more anterior than the first width while in use, the superior strap portion and the inferior strap portion each connected to or formed integrally with the anterior strap portion at a respective corner of the generally triangular surface.

Another form of the present technology comprises a connection member for a patient interface, the connection member configured to removably connect one side of a positioning and stabilising structure to a side of an interfacing portion of the patient interface, wherein the connection member is configured to engage at least two strap portions of the stabilising structure.

Another form of the present technology is a patient interface that comprises a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use;

a positioning and stabilizing structure to provide a force to hold a seal-forming structure in a therapeutically effective position on a patient's head, the positioning and stabilizing structure including a first strap portion and a second strap portion; and an interface connection portion having a first component configured to removably engage with an interfacing portion of the patient interface;

a first strap connection portion configured to engage with a first strap portion; and a second strap connection portion configured to engage with a second strap portion;

wherein the interface connection portion is configured to engage the interfacing portion with a magnetic coupling, and wherein the first strap connection portion and the second strap connection portion are movable relative to the interface connection portion.

In examples: a) the first strap connection portion is a superior strap connection portion for connection, in use, to a superior strap portion of the positioning and stabilising structure; b) the second strap connection portion is an inferior strap connection portion for connection, in use, to an inferior strap portion of the positioning and stabilising structure; c) the connection member comprises a single superior strap connection portion and a single inferior strap connection portion; d) the superior strap connection portion comprises a first hook configured to receive an end of the superior strap portion; e) the inferior strap connection portion comprises a second hook configured to receive an end of the inferior strap portion; f) the superior strap connection portion comprises a first loop configured to receive an end of the superior strap portion; g) the inferior strap comprises a second loop configured to receive an end of the inferior strap portion; h) the interface connection portion and the interfacing portion are configured to prevent or limit rotation of the interface connection portion relative to the interfacing portion when the patient interface is in use; i) the interface connection portion includes a first bearing formation configured to engage a second bearing formation of the interfacing portion; j) the interface connection portion and the interfacing portion are configured to prevent or limit rotation about a horizontal axis of the interface connection portion relative to the interfacing portion when the patient interface is in use; k) the interface connection portion is configured to connect to the plenum chamber; l) the interface connection portion is configured to connect to a frame of the patient interface; m) a single magnetic catch connects the interface connection portion and the interfacing portion wherein the first component is a first component of the magnetic catch and a second component of the magnetic catch is part of the interfacing portion; n) the first component is a protrusion configured to be received in a slot of the interfacing portion; o) the second component is bonded to the a plenum chamber; p) the second component is over-moulded to the plenum chamber; q) the interface connection portion comprises a curved edge which is adapted to be gripped by the user when disconnecting the interface connection portion from the interfacing portion; r) the curved edge is provided to the anterior side of the interface connection portion; s) the connecting member is formed using an additive manufacturing process to produce a customised design specific to the anthropometric data of the patient; t) the connecting member is formed from a metal; u) the metal retains a new shape after being heated and deformed into the new shape; v) the superior strap connection portion is connected to the interface connection portion by a ball and socket mechanism; w) the inferior strap connection portion is connected to the interface connection portion by a ball and socket mechanism; x) the superior strap connection portion is movable via the first ball and socket mechanism independently of the inferior strap connection portion; and/or y) the inferior strap connection portion is movable via the second ball and socket mechanism independently of the superior strap connection portion.

Another form of the present technology comprises a patient interface assembly, the patient interface assembly comprising:

an interfacing portion;

a positioning and stabilising structure comprising a superior strap portion and an inferior strap portion; and two connection members, each configured to receive a respective end of the superior strap portion and a respective end of the inferior strap portion, wherein each connection member is configured to be removably attachable to a respective left or right hand side of interfacing portion.

In examples: a) the connection members are connected to the interfacing portion in a fixed orientation; b) the connection members are connected to the shell in a fixed orientation; c) increasing the tension the superior strap connection portions moves a superior portion of the cushion in a posterior direction; and/or d) increasing the tension of the inferior strap connection portions moves an inferior portion of the plenum chamber a posterior direction.

Another form of the present technology comprises a patient interface system, the patient interface system comprising:

an interfacing portion;

a first headgear configured to removably connect to the interfacing portion; and a second headgear configured to removably connect to the interfacing portion;

wherein the location or presence of at least one strap portion of the second headgear is different to that of the first headgear;

wherein at any one time only one of the first or second headgear is connected to the interfacing portion.

Another form of the present technology comprises a patient interface system, the patient interface system comprising:

an interfacing portion;

a first connection member configured to be removably coupled to the interfacing portion;

a second connection member configured to be removably coupled to the interfacing portion;

a first headgear configured to removably connect to the interfacing portion via the first connection member; and a second headgear configured to removably connect to the interfacing portion via the second connection member;

wherein straps of the first headgear are different from straps of the second headgear;

wherein the first connection member and the second connection member are each configured to engage the interfacing portion at a connection point, at least one strap portion of the first headgear and at least one strap of the second headgear are configured to extend generally toward the connection point; and wherein at any one time only one of the first or second headgear is connected to the interfacing portion.

In examples: a) the first headgear comprises a two-point connection; b) the second headgear comprises a four-point connection; c) the second headgear comprises a two-point connection; d) the first headgear comprises a positioning and stabilising structure as described above; e) the connection portion connected to the first headgear and the connection member connected to the second headgear are configured to removably connect to the interfacing portion at the same position; f) a single magnet catch connects the connection portion and the connection member to the interfacing portion, wherein a first component of the magnetic catch is part of the connection portion or the connection member and a second component of the magnetic catch is part of the interfacing portion; g) the first connection member and the second connection member are each configured to magnetically couple to the interfacing portion; h) a headgear vector supplied by the first headgear or the second headgear is configured to cause pivotable movement in the interfacing structure; i) the interfacing structure is configured to pivot about the connection point; and/or j) the first connection member includes one loop configured to receive a strap of the first headgear, and the second connection member includes two loops each configured to receive a strap of the second headgear.

Another form of the present technology comprises a patient interface comprising

- a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;
- a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and
- a positioning and stabilising structure for a full-face.

Another form of the present technology comprises a positioning and stabilising structure for a full-face mask, the positioning and stabilising structure comprising:

- a superior strap portion;
- an inferior strap portion; and
- an anterior strap portion, each connected to or formed integrally with the superior strap portion and the inferior strap portion, the anterior strap portion connected or connectable to a connection portion which engages the plenum chamber, the connection portion being releasably engageable from the plenum chamber; and
- wherein the superior strap portion and the inferior strap portion join the anterior strap portions anterior to the patient's ears, in use; and
- wherein the anterior strap portion forms a loop when connected with the connection portion, the loop is adjustable to adjust the direction and magnitude of a headgear vector.

Another form of the present technology comprises a positioning and stabilising structure for a patient interface, the positioning and stabilising structure comprising:

- a superior strap portion;
- an inferior strap portion;
- at least one anterior strap portion connected to or formed integrally with the superior strap portion and the inferior strap portion;
- wherein the anterior strap portion comprises:
  - a strap receiving portion; and
  - a strap attachment portion which is releasably connectable to the strap receiving portion such that the anterior strap portion forms a loop, wherein in use the loop engages a connection portion which engages the plenum chamber;
- wherein the strap receiving portion is configured to engage the strap attachment portion in a selected one of a plurality of possible positions,
- wherein the plurality of possible positions comprises a plurality of possible angular positions of the strap attachment portion relative to the strap receiving portion, and
- wherein the angle between the strap attachment portion and the strap receiving portion when connected is configured to cause pivotable movement in the plenum chamber and/or seal forming structure.

Another form of the present technology comprises a positioning and stabilising structure for a patient interface, the positioning and stabilising structure comprising:

- a superior strap portion;
- an inferior strap portion;
- at least one anterior strap portion connected to or formed integrally with the superior strap portion and the inferior strap portion;
- wherein the anterior strap portion comprises:
  - a strap receiving portion; and
  - a strap attachment portion which is releasably connectable to the strap receiving portion such that the anterior strap portion forms a loop, wherein in use the loop engages a connection portion which engages the plenum chamber;
- wherein the strap receiving portion is configured to engage the strap attachment portion in a selected one of a plurality of possible positions to adjust the direction and magnitude of a headgear vector, and
- wherein the headgear vector is configured to cause pivotable movement in the plenum chamber and/or seal forming structure.

Another form of the present technology comprises a connection member for connecting the positioning and stabilizing structure to the plenum chamber, the connection member comprising:

- an interface connection portion having a first component configured to removably engage with an interfacing portion of the patient interface;
- a first strap connection portion configured to engage with the first strap portion; and
- a second strap connection portion configured to engage with the second strap portion;
- wherein the interface connection portion is configured to engage the interfacing portion with a magnetic coupling, and
- wherein the first strap connection portion and the second strap connection portion are each movably connected to the interface connection portion.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
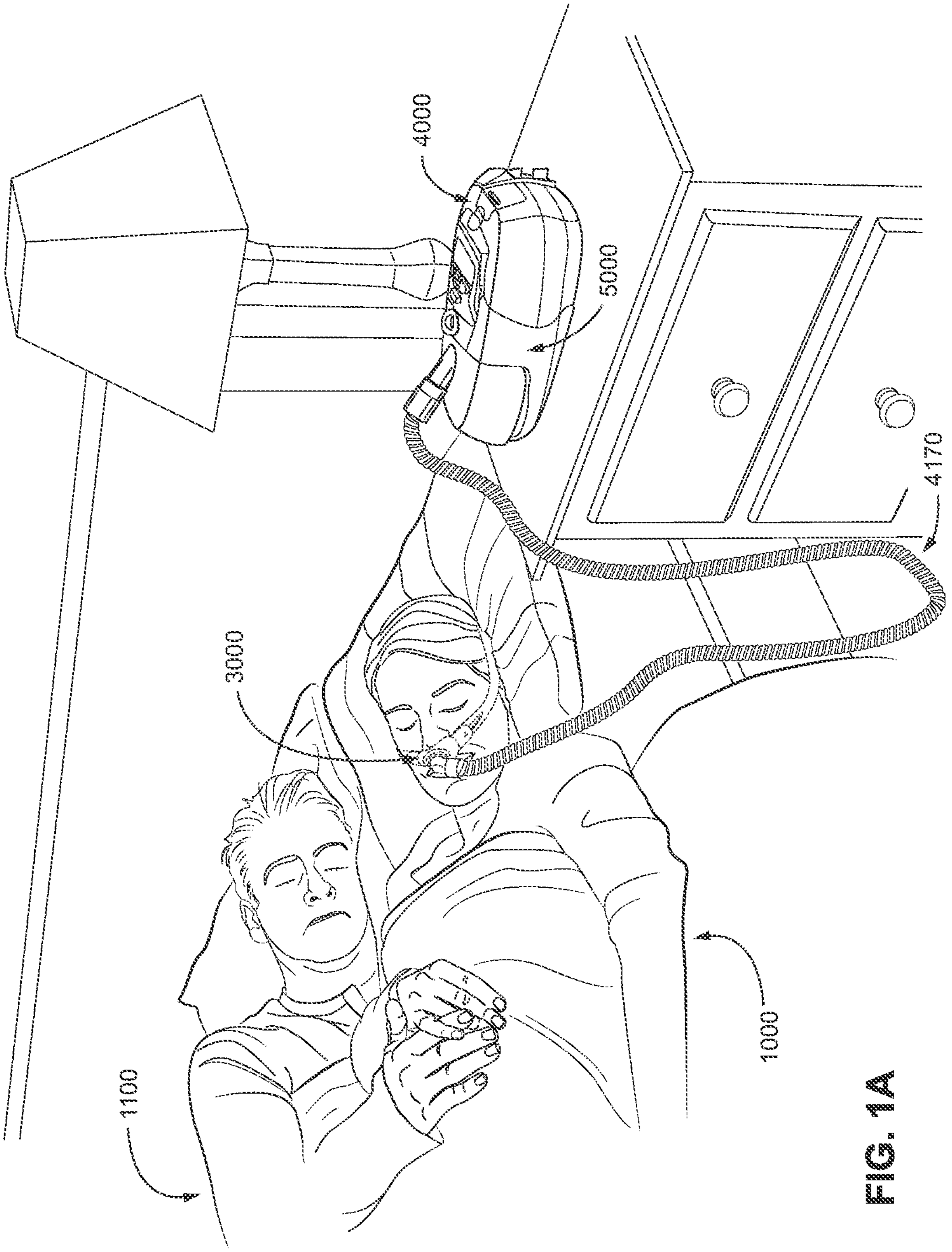
Figure 1B:
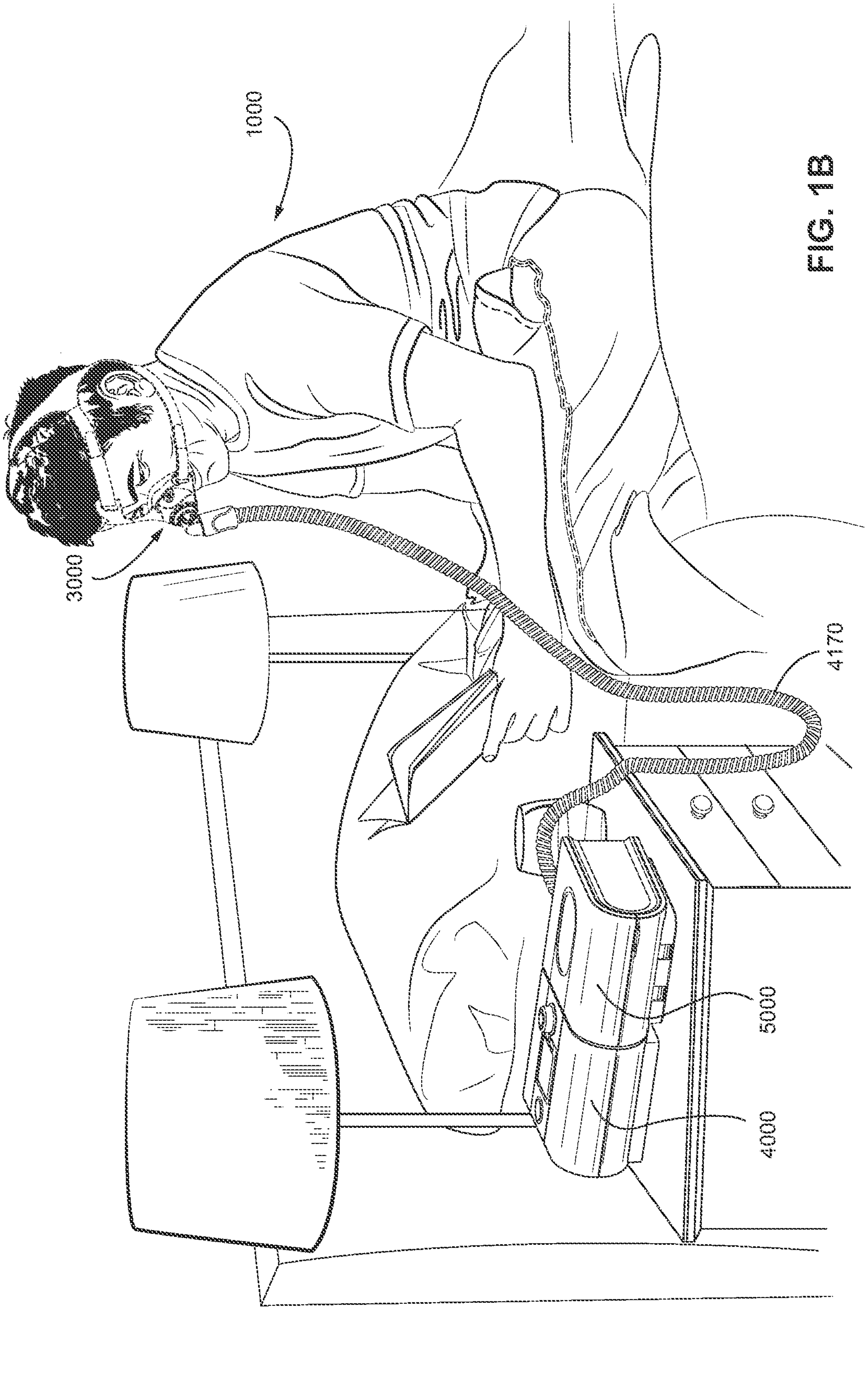
Figure 1C:
Figure 2A:
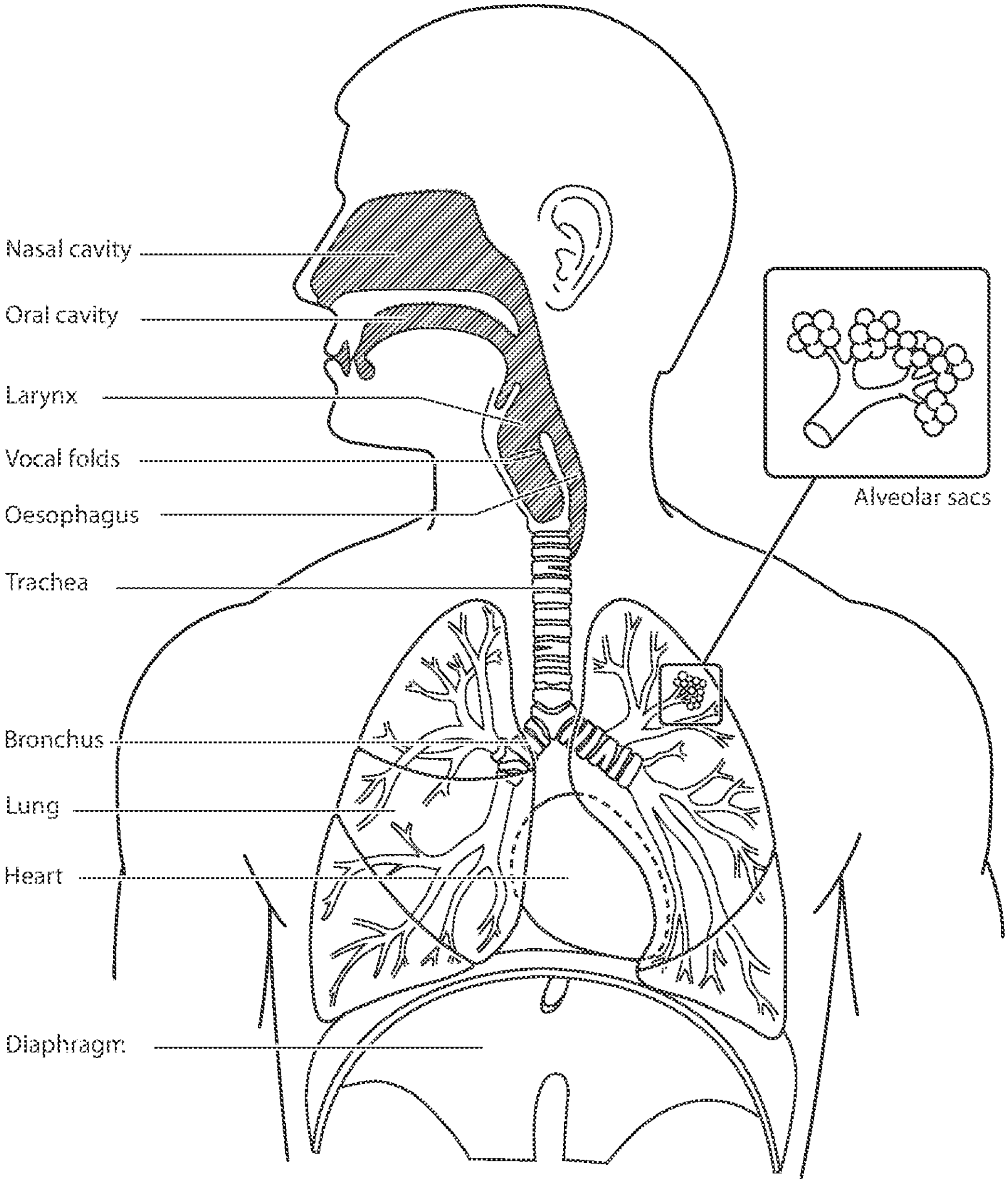
FIG. 2A shows an overview of a human respiratory system including the nasal and oral cavities, the larynx, vocal folds, oesophagus, trachea, bronchus, lung, alveolar sacs, heart and diaphragm.
Figure 2B:
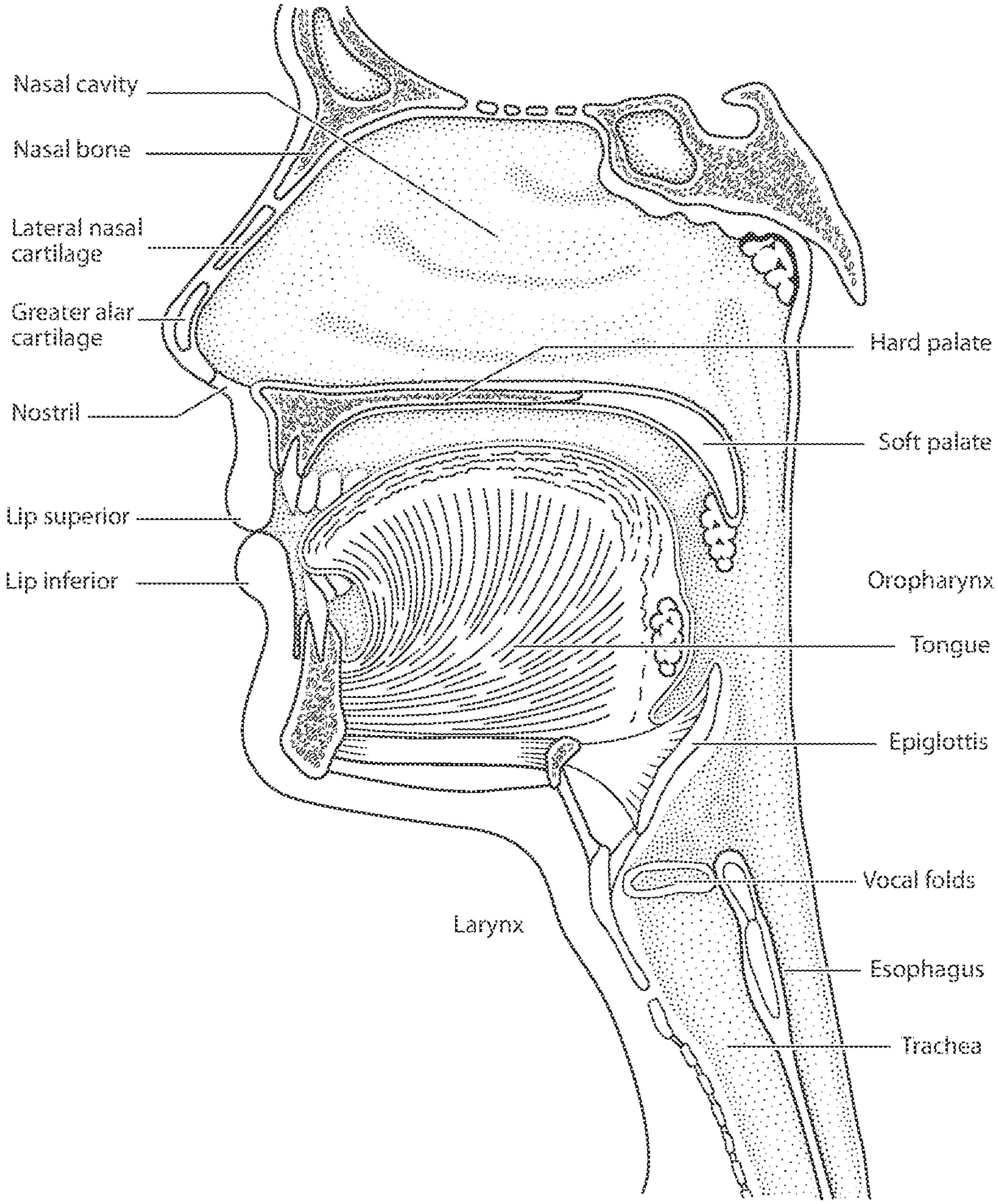
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
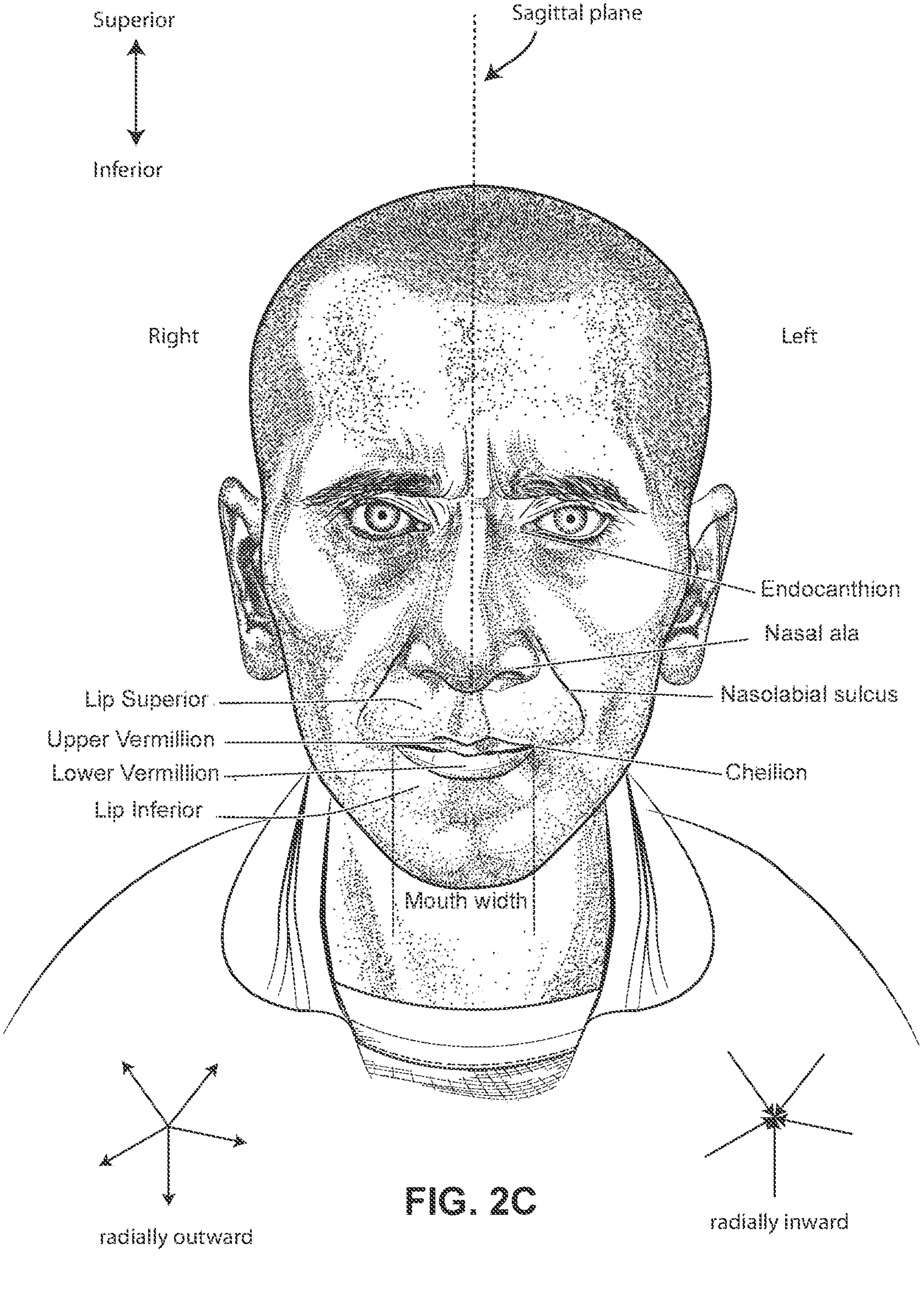
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
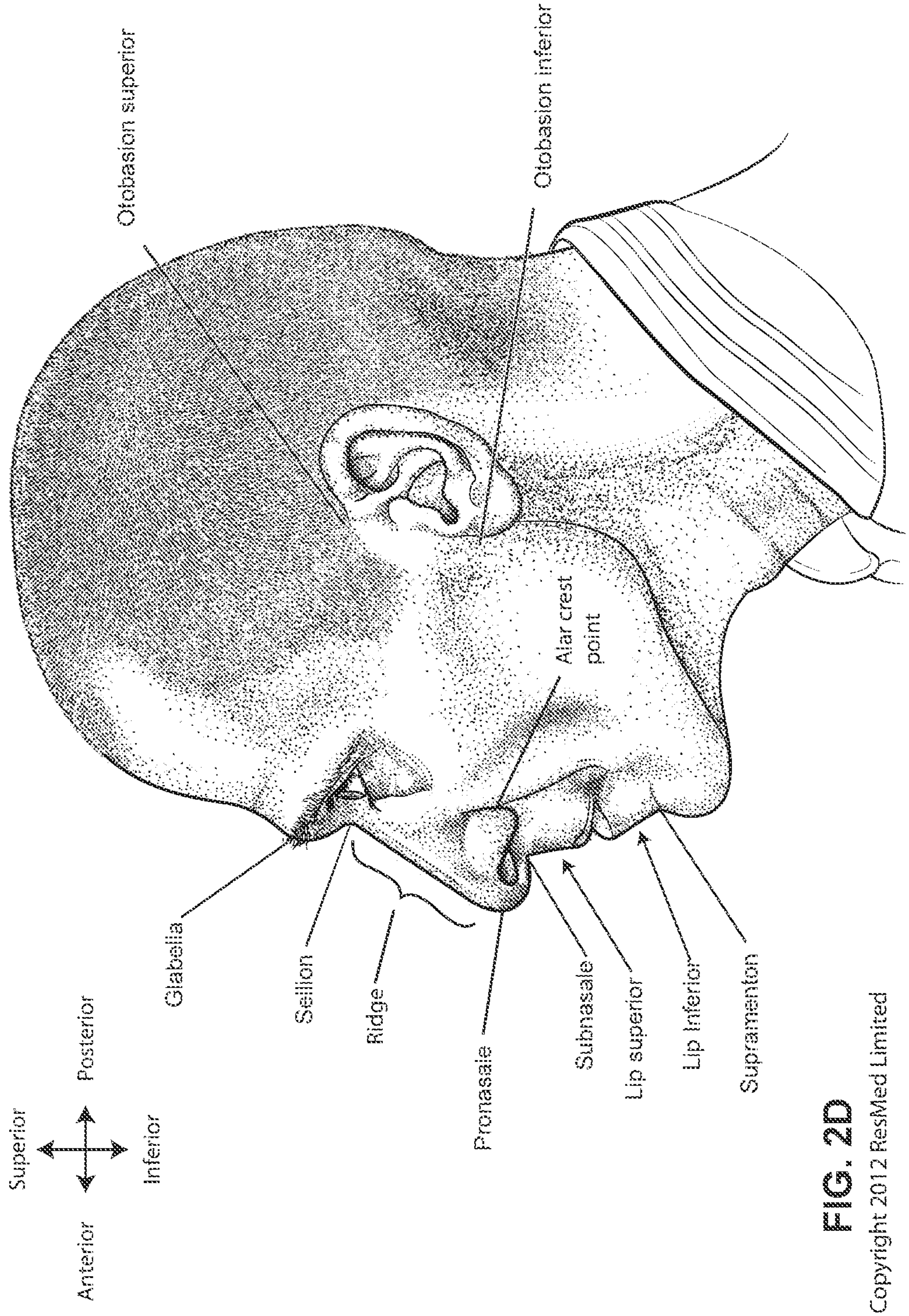
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
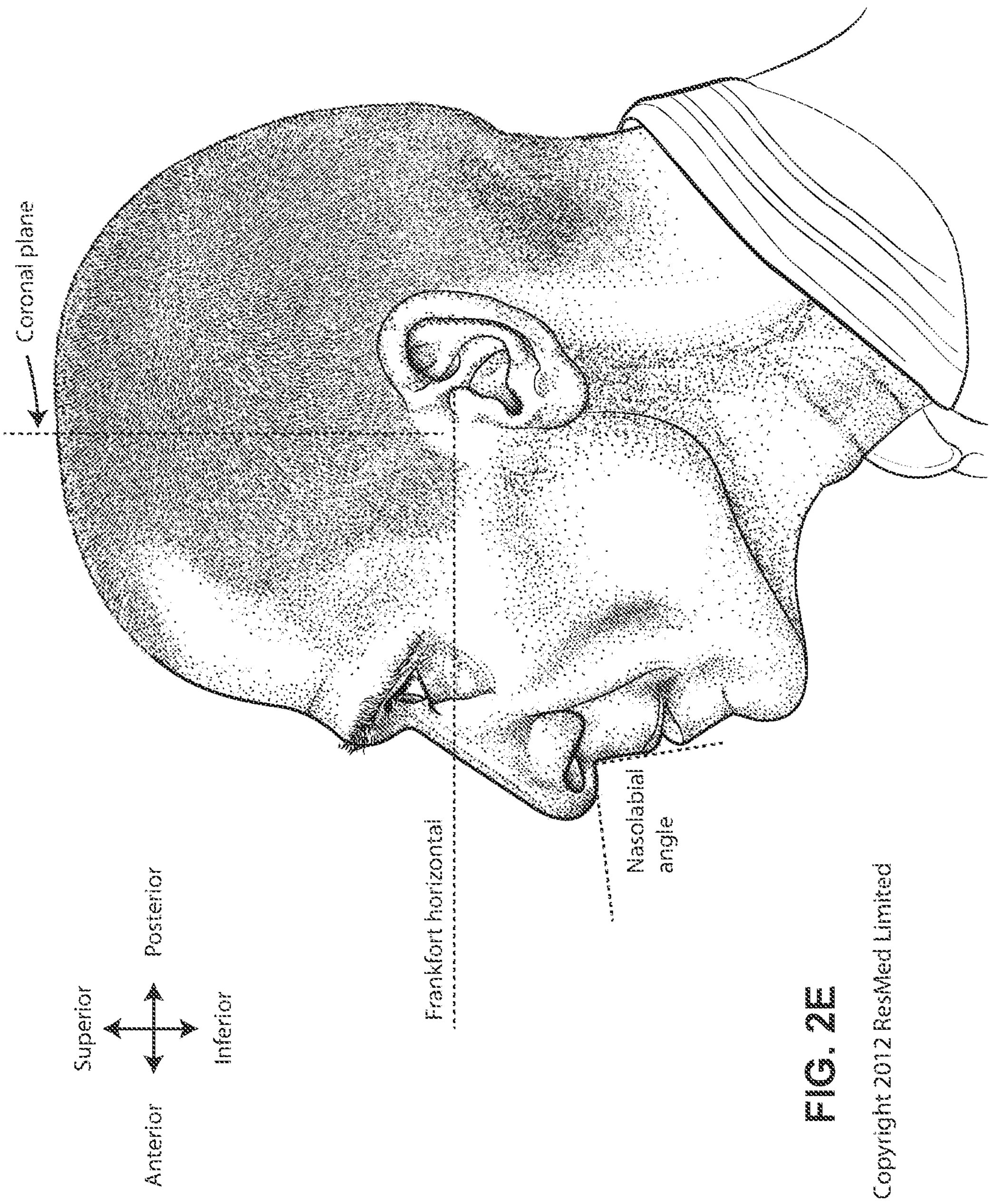

FIG. 2E is a further side view of a head. The approximate locations of the Frankfort horizontal and nasolabial angle are indicated. The coronal plane is also indicated.

Figure 2F:
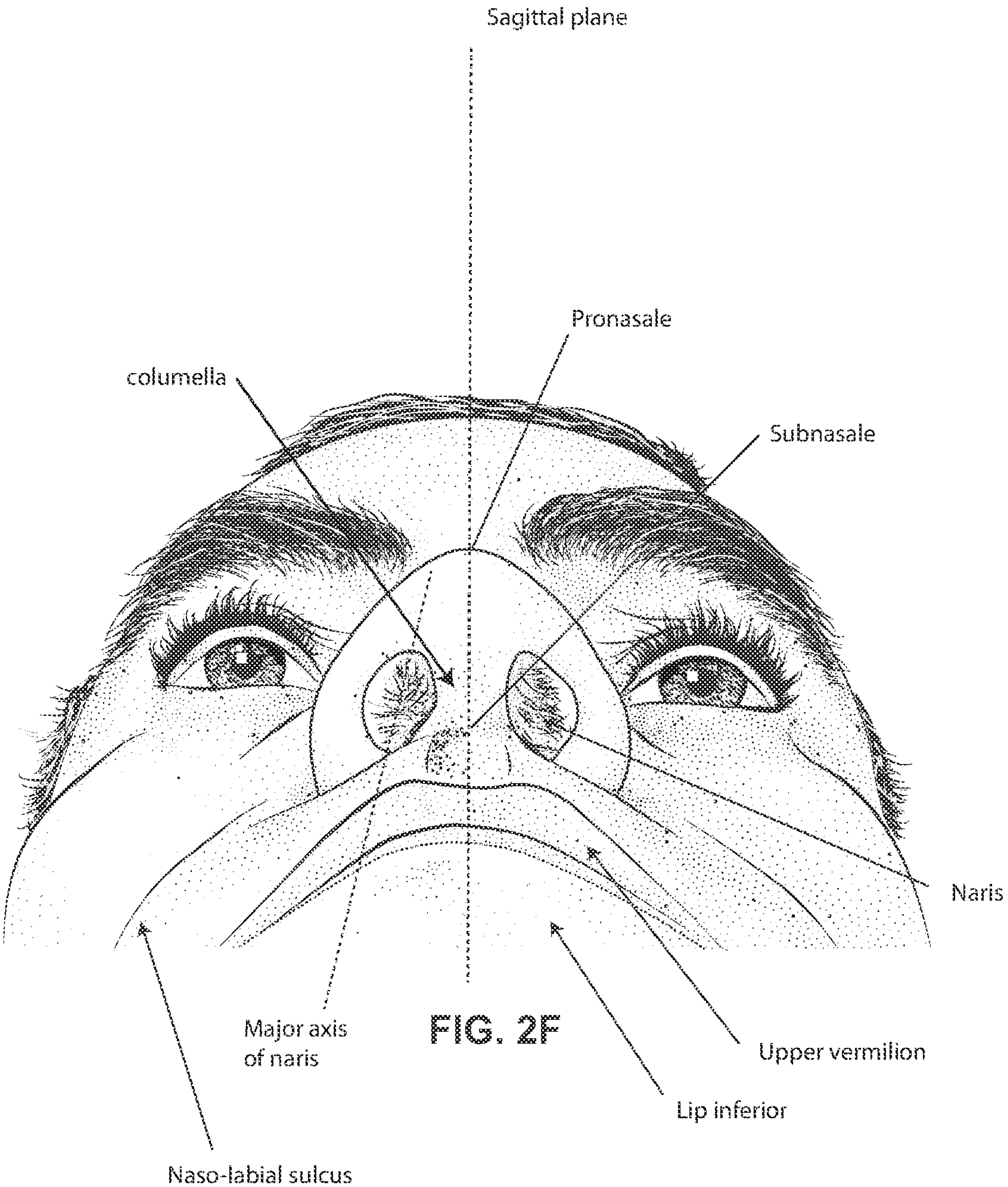

FIG. 2F shows a base view of a nose with several features identified including naso-labial sulcus, lip inferior, upper Vermilion, naris, subnasale, columella, pronasale, the major axis of a naris and the midsagittal plane.

Figure 2G:
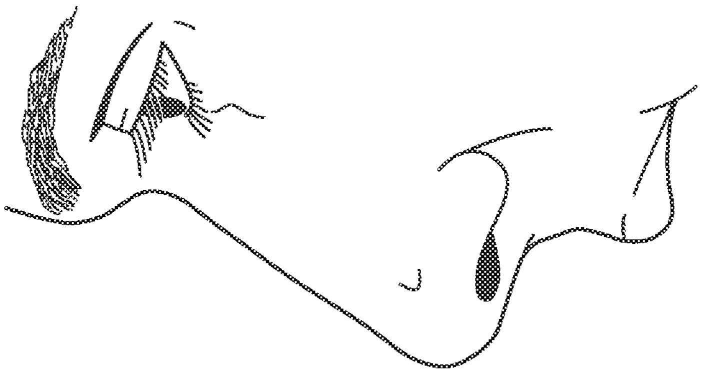

FIG. 2G shows a side view of the superficial features of a nose.

Figure 2H:
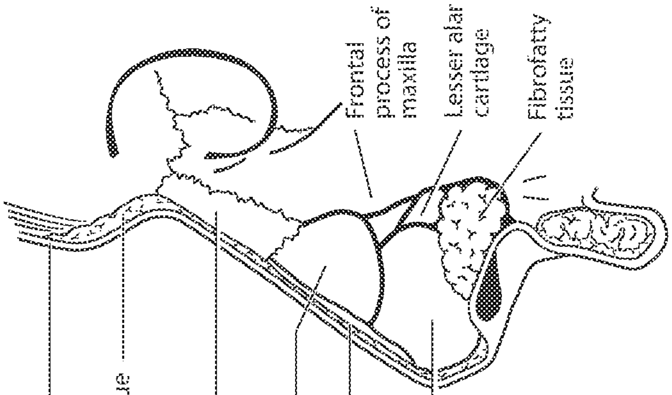

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

Figure 2I:
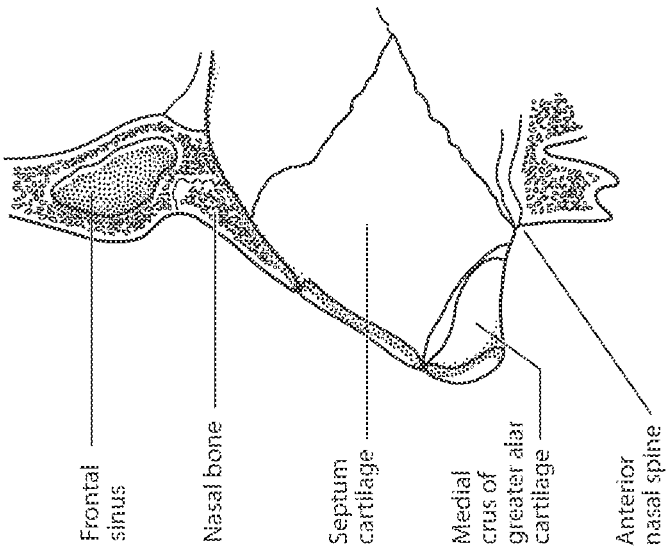

FIG. 2I shows a medial dissection of a nose, approximately several millimeters from the midsagittal plane, amongst other things showing the septum cartilage and medial crus of greater alar cartilage.

Figures 2J, 2K:
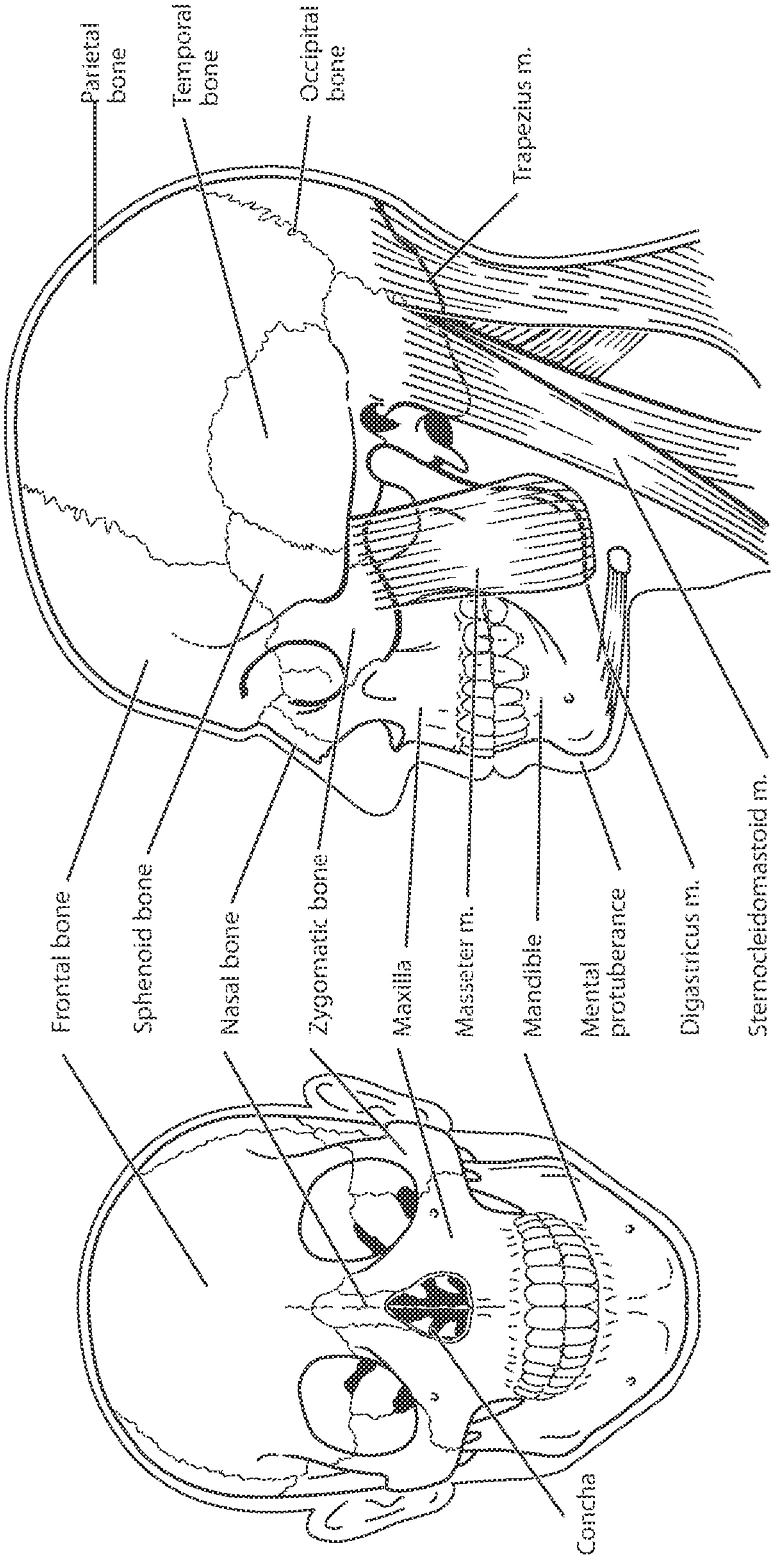

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
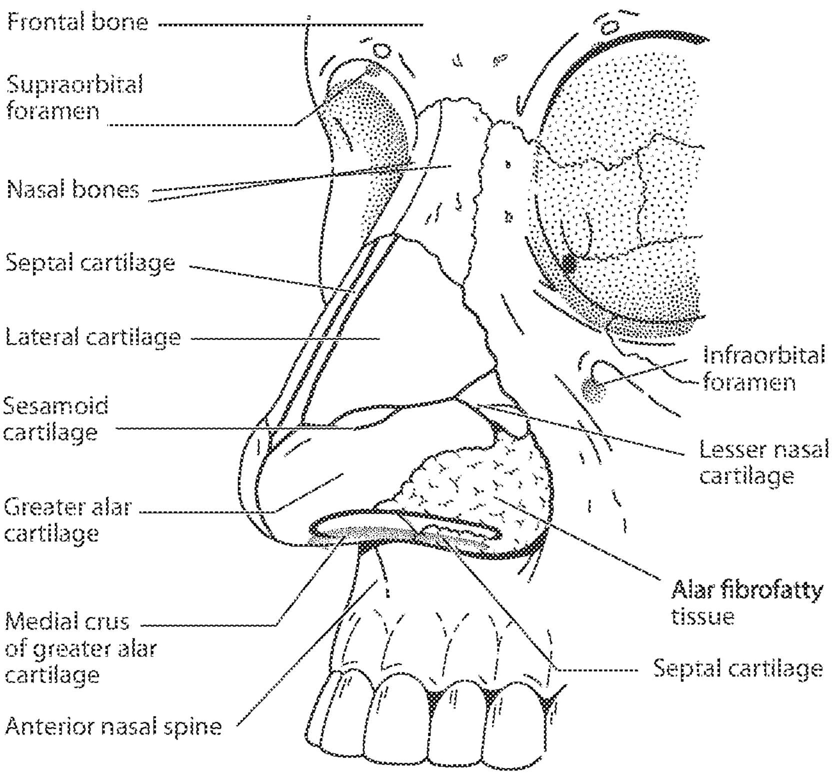

FIG. 2L shows an anterolateral view of a nose.

4.3 Patient Interface

Figure 3A:
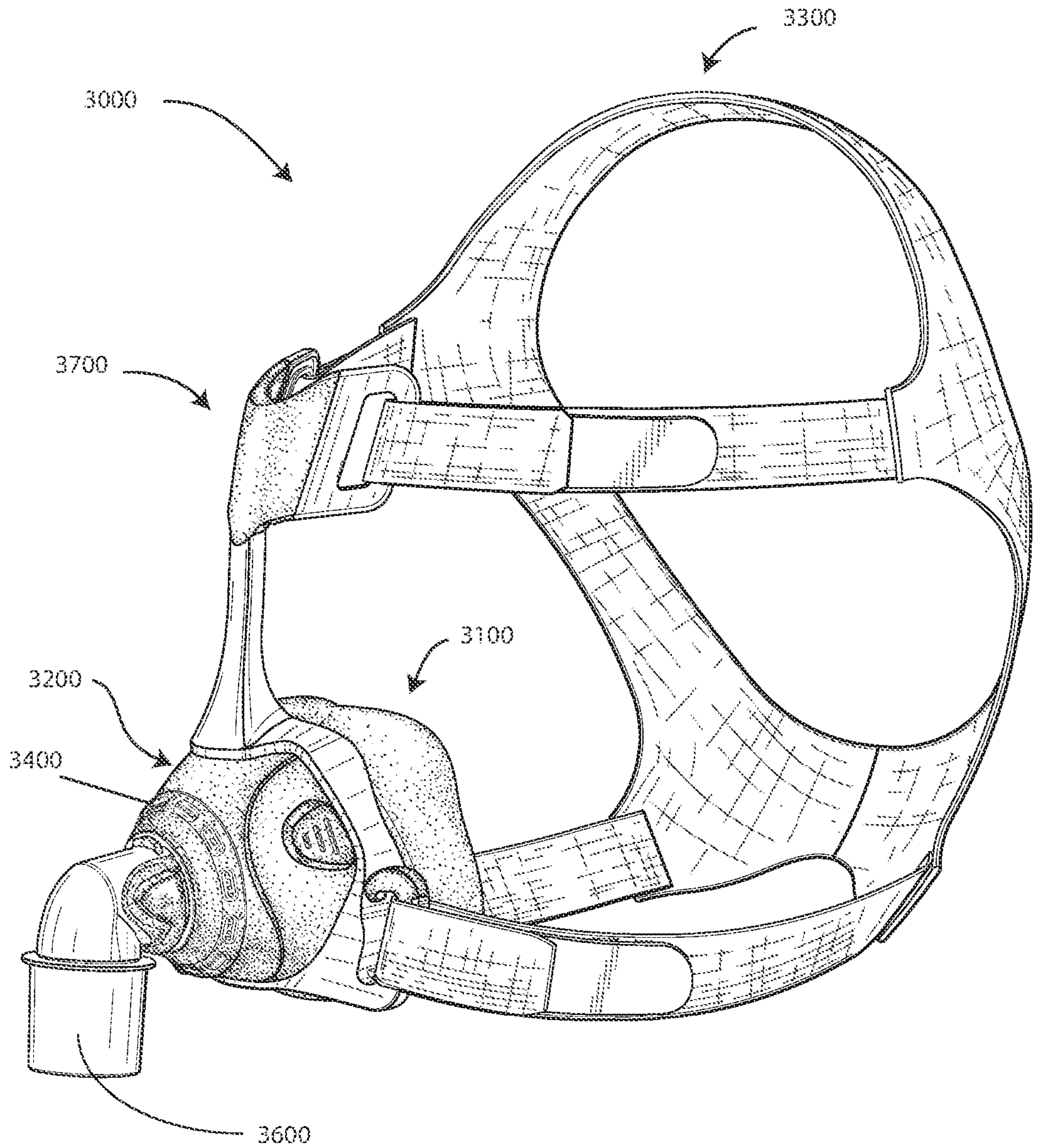

FIG. 3A shows a patient interface in the form of a nasal mask in accordance with one form of the present technology.

Figure 3B:
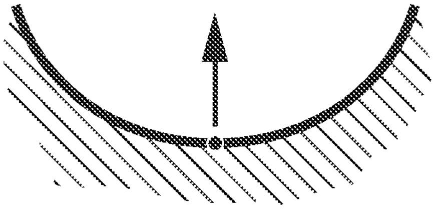

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
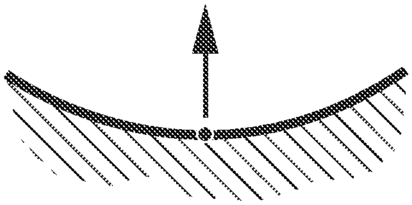

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
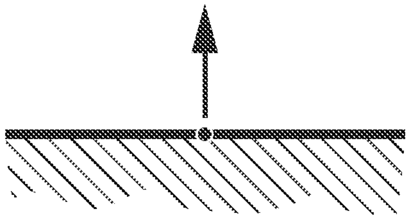

FIG. 3D shows a schematic of a cross-section through a structure at a point. An outward normal at the point is indicated. The curvature at the point has a value of zero.

Figure 3E:
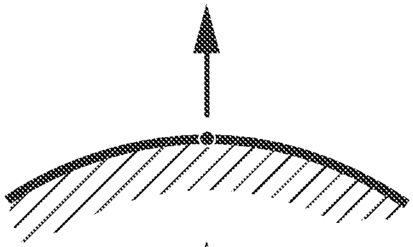

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
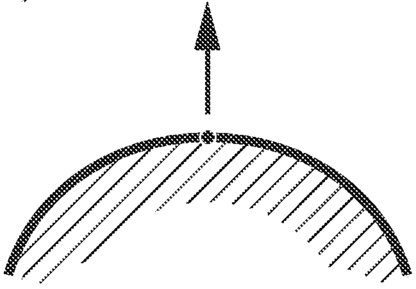

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
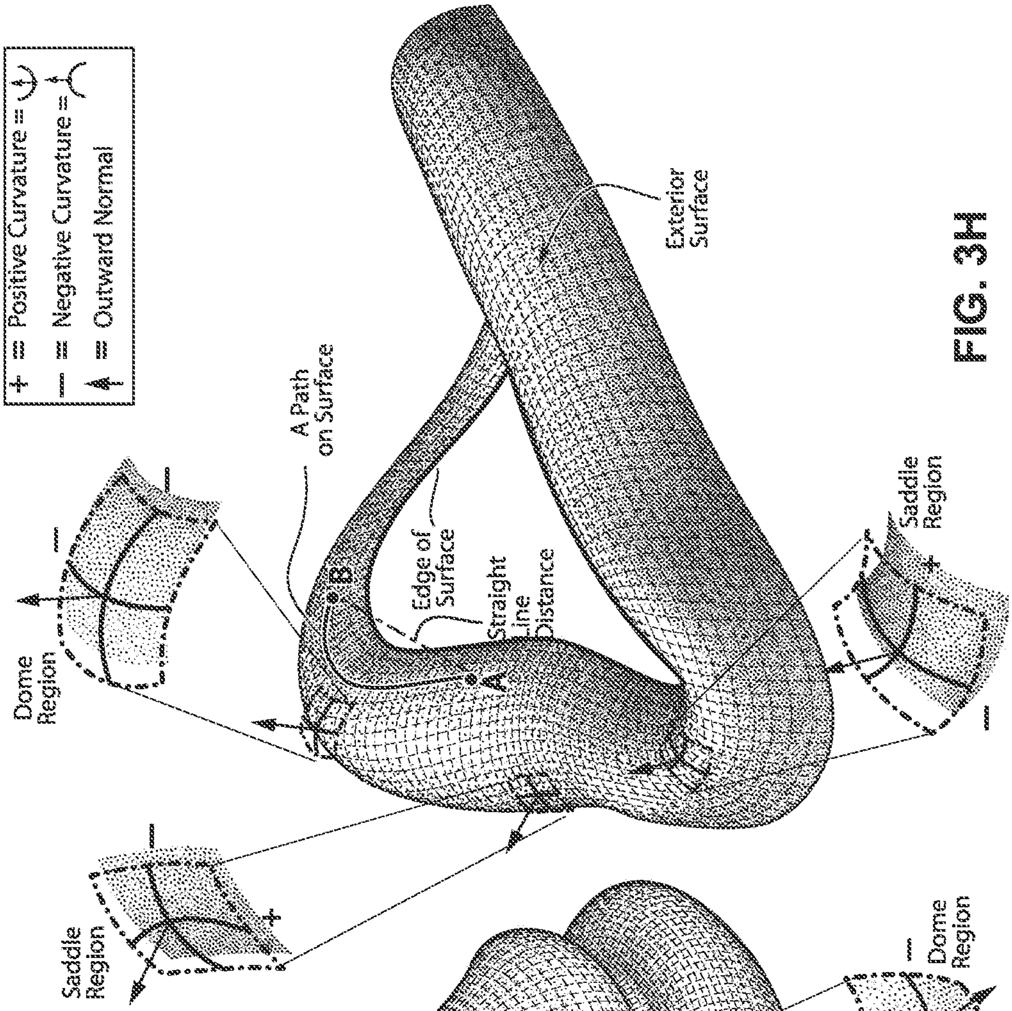
Figure 3G:
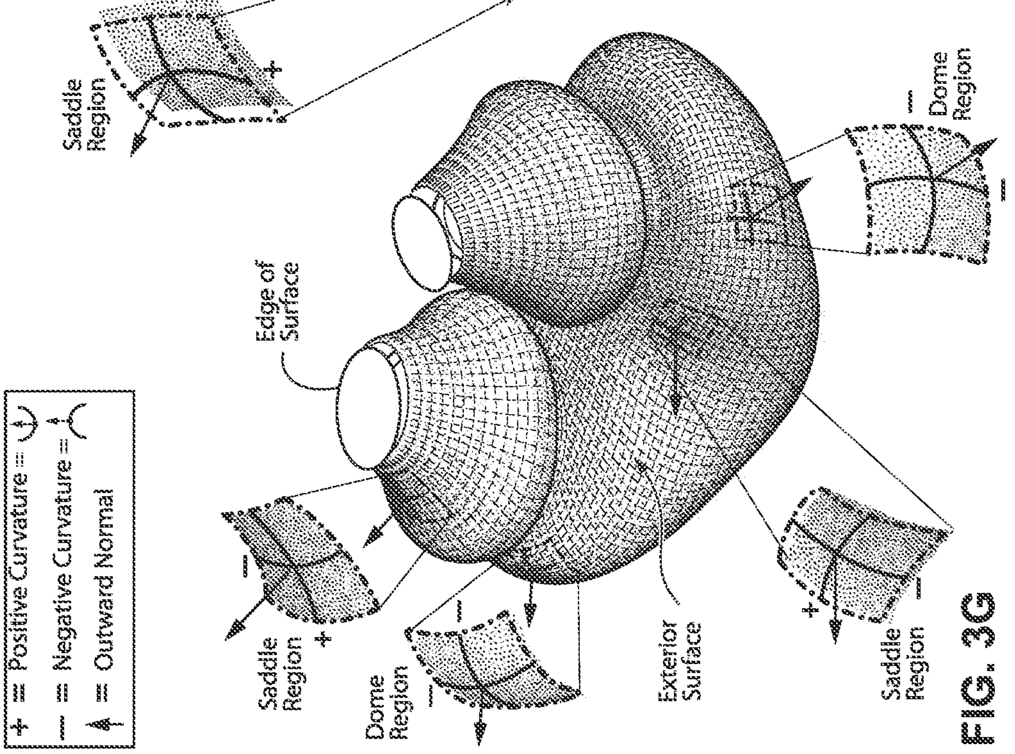

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
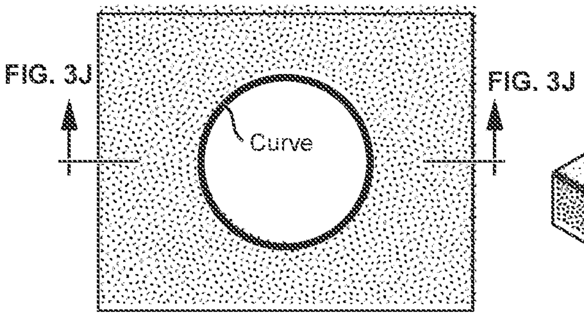

FIG. 3I shows the surface of a structure, with a one dimensional hole in the surface. The illustrated plane curve forms the boundary of a one dimensional hole.

Figure 3K:
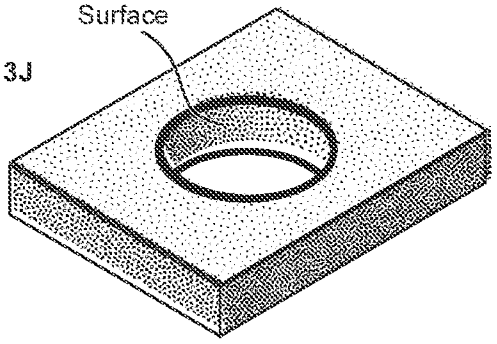
Figure 3J:
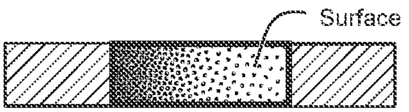

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
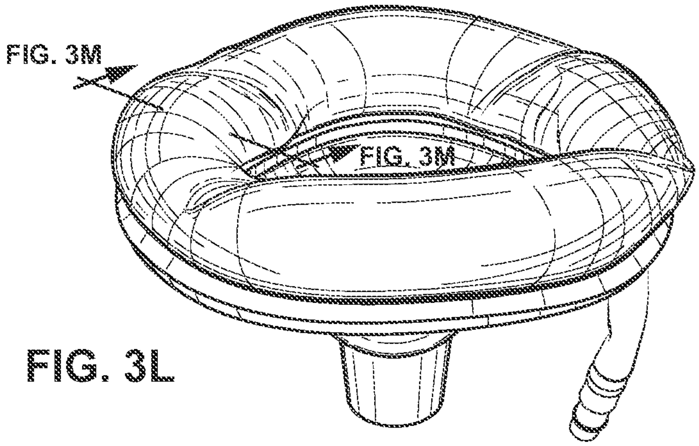

FIG. 3L shows a mask having an inflatable bladder as a cushion.

Figure 3M:
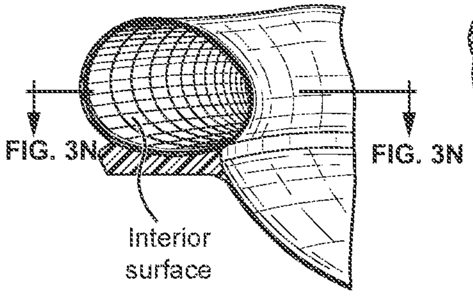

FIG. 3M shows a cross-section through the mask of FIG. 3L, and shows the interior surface of the bladder. The interior surface bounds the two dimensional hole in the mask.

Figure 3N:
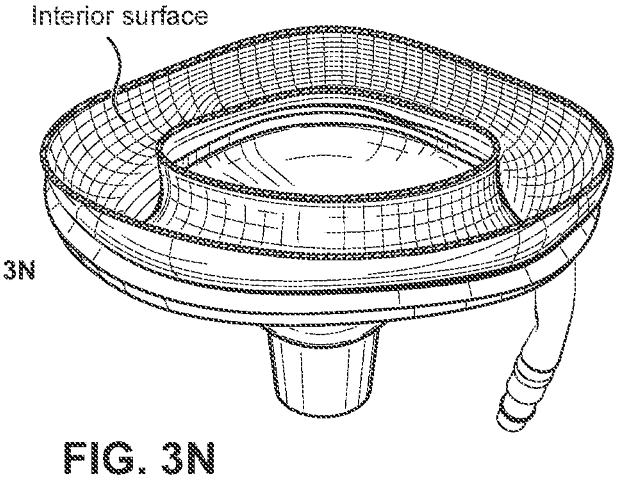

FIG. 3N shows a further cross-section through the mask of FIG. 3L. The interior surface is also indicated.

Figure 3O:
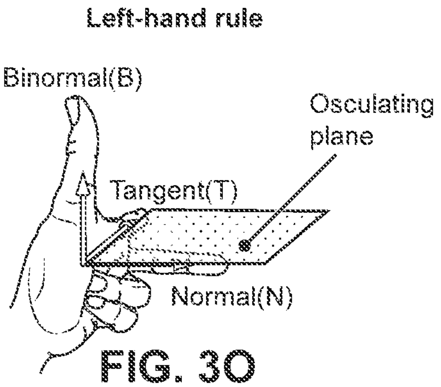

FIG. 3O illustrates a left-hand rule.

Figure 3P:
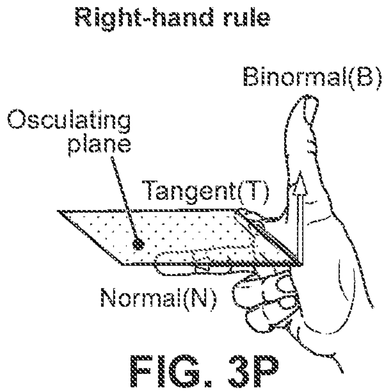

FIG. 3P illustrates a right-hand rule.

Figure 3Q:
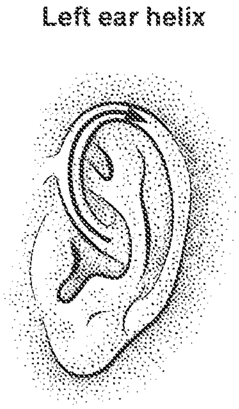

FIG. 3Q shows a left ear, including the left ear helix.

Figure 3S:
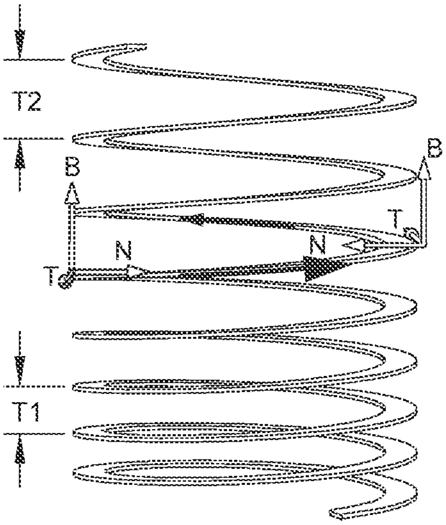
Figure 3R:
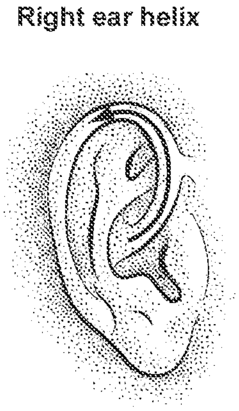

FIG. 3R shows a right ear, including the right ear helix.

FIG. 3S shows a right-hand helix.

Figure 3T:
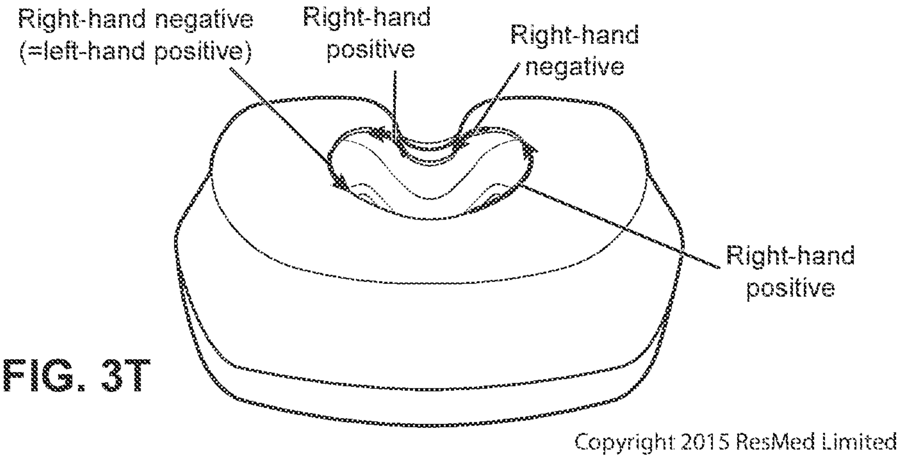

FIG. 3T shows a view of a mask, including the sign of the torsion of the space curve defined by the edge of the sealing membrane in different regions of the mask.

Figure 3U:
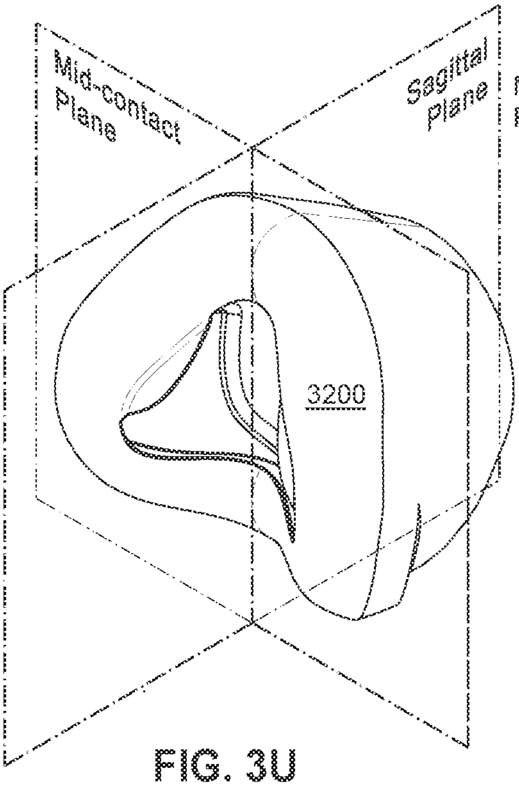

FIG. 3U shows a view of a plenum chamber 3200 showing a sagittal plane and a mid-contact plane.

Figure 3V:
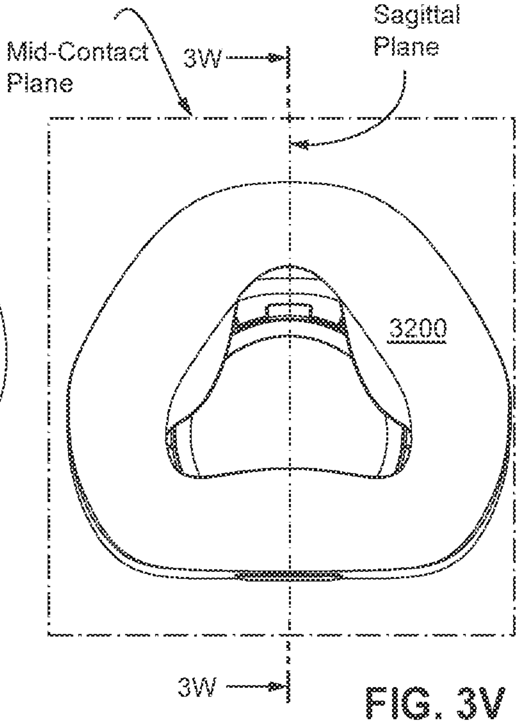

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
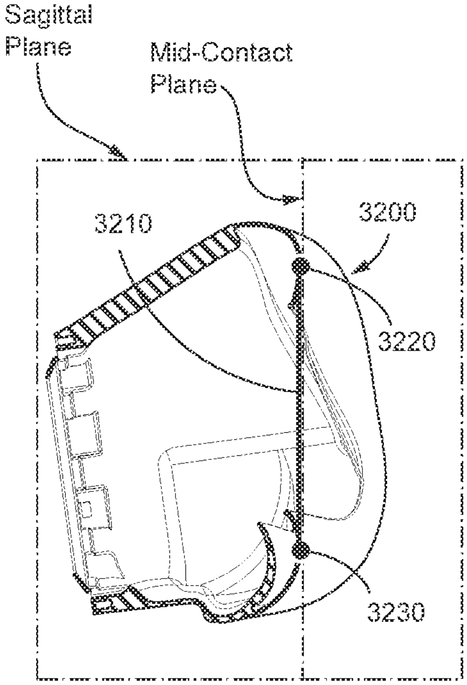

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
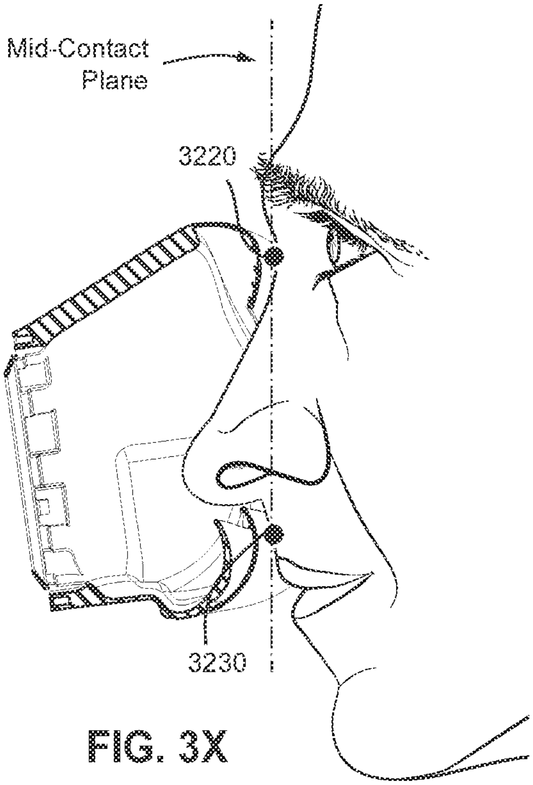

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
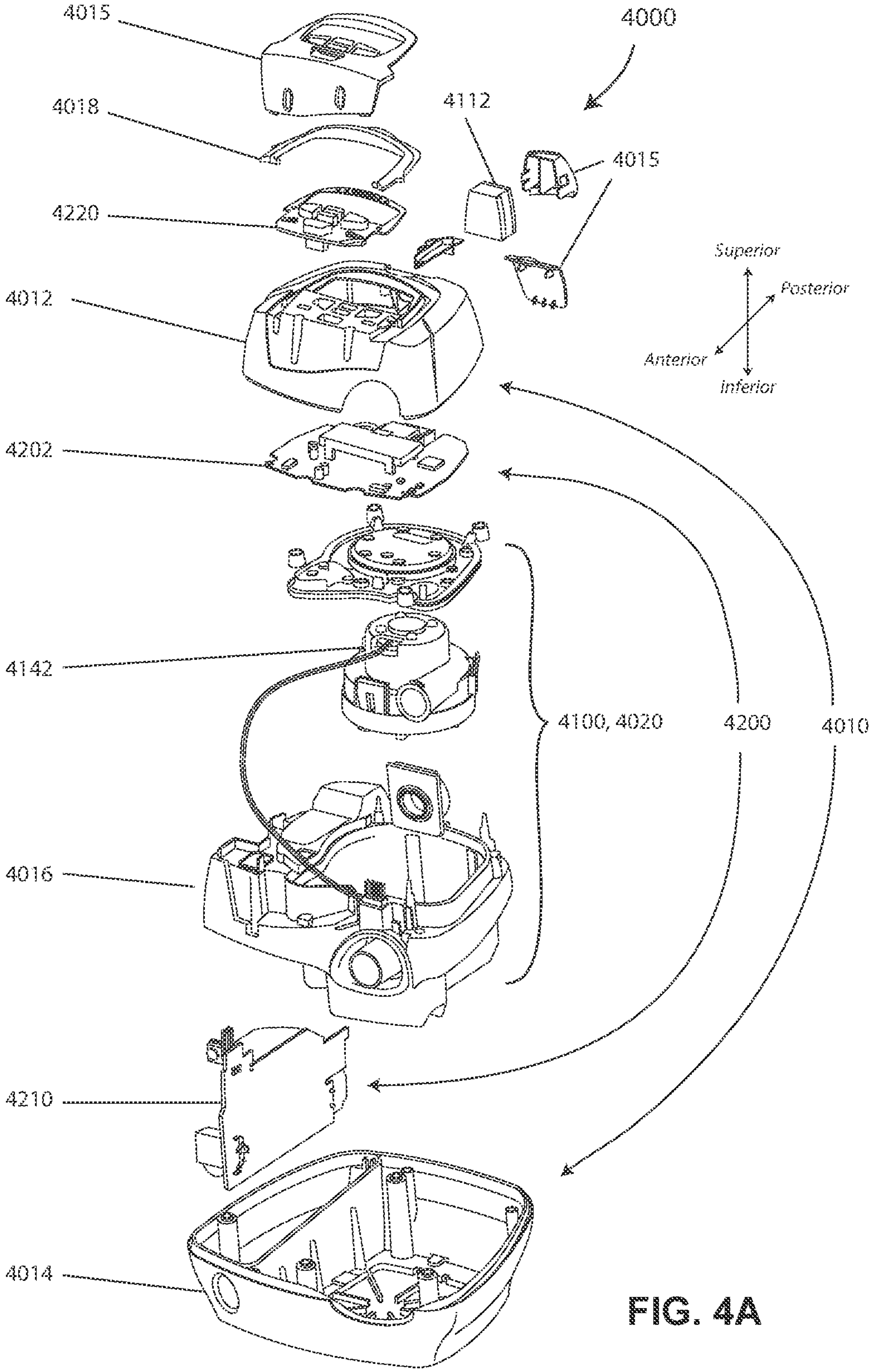

FIG. 4A shows an RPT device in accordance with one form of the present technology.

Figure 4B:
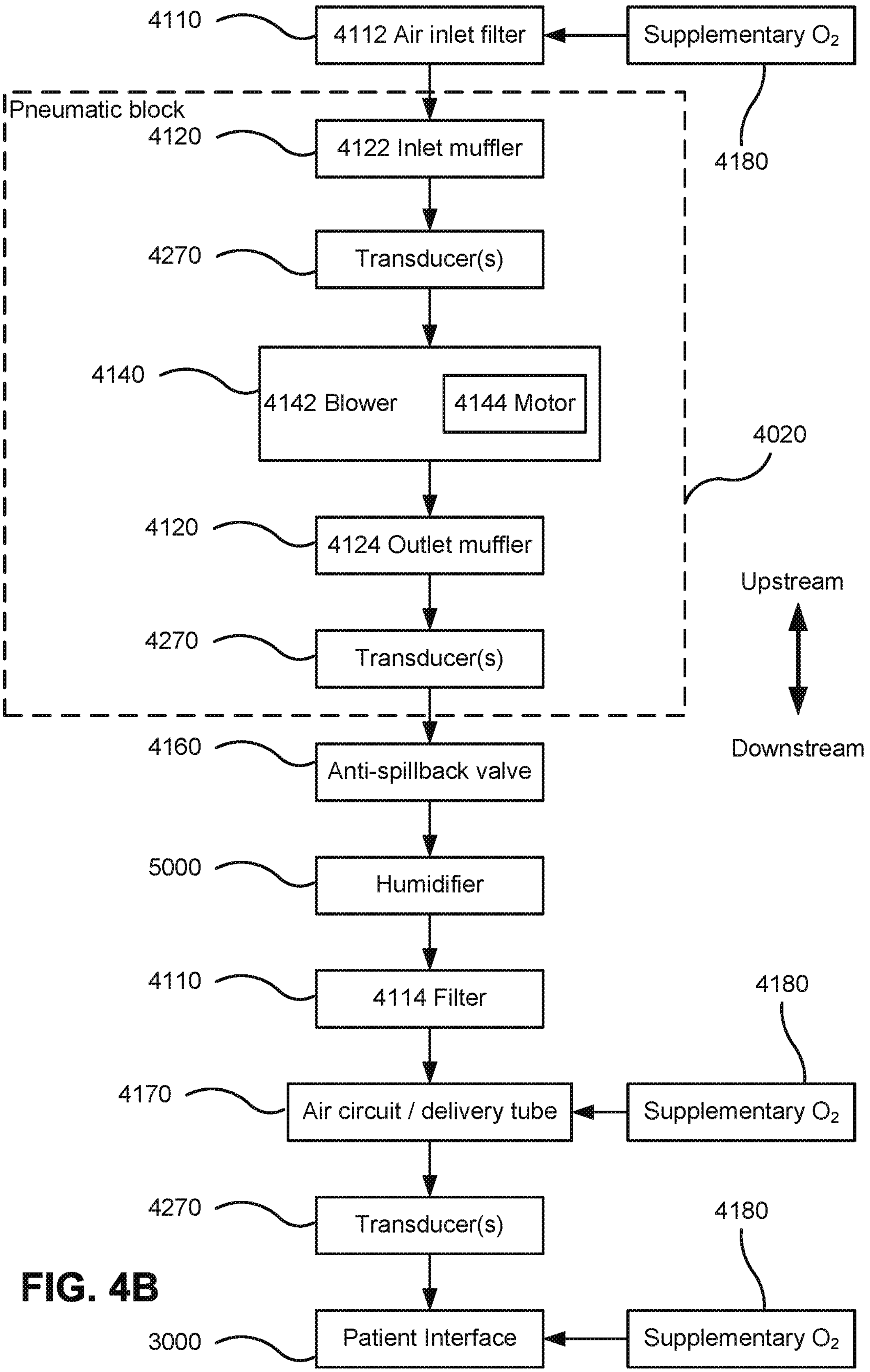

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
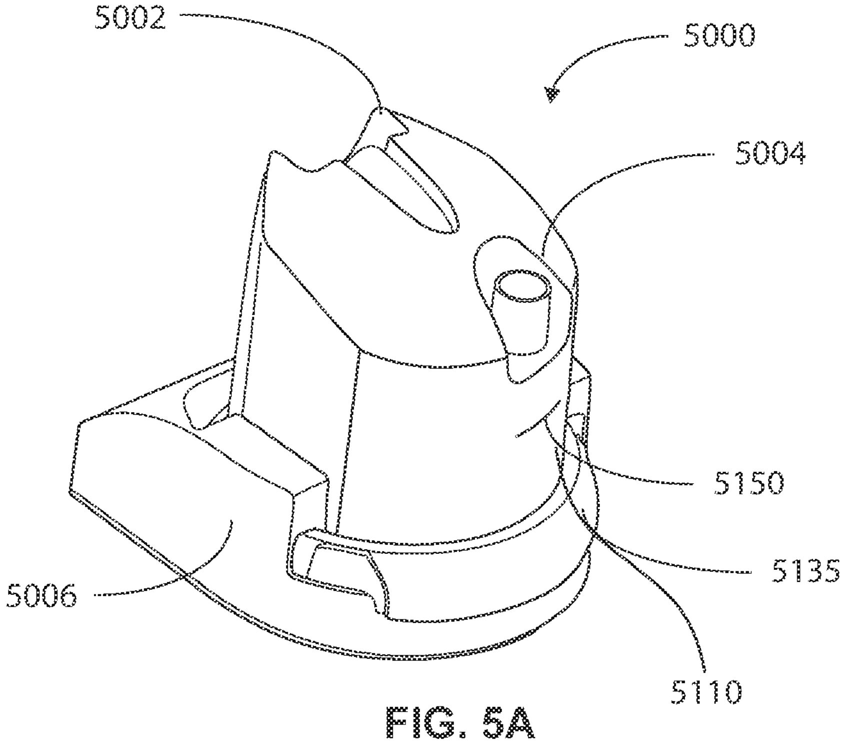

FIG. 5A shows an isometric view of a humidifier in accordance with one form of the present technology.

Figure 5B:
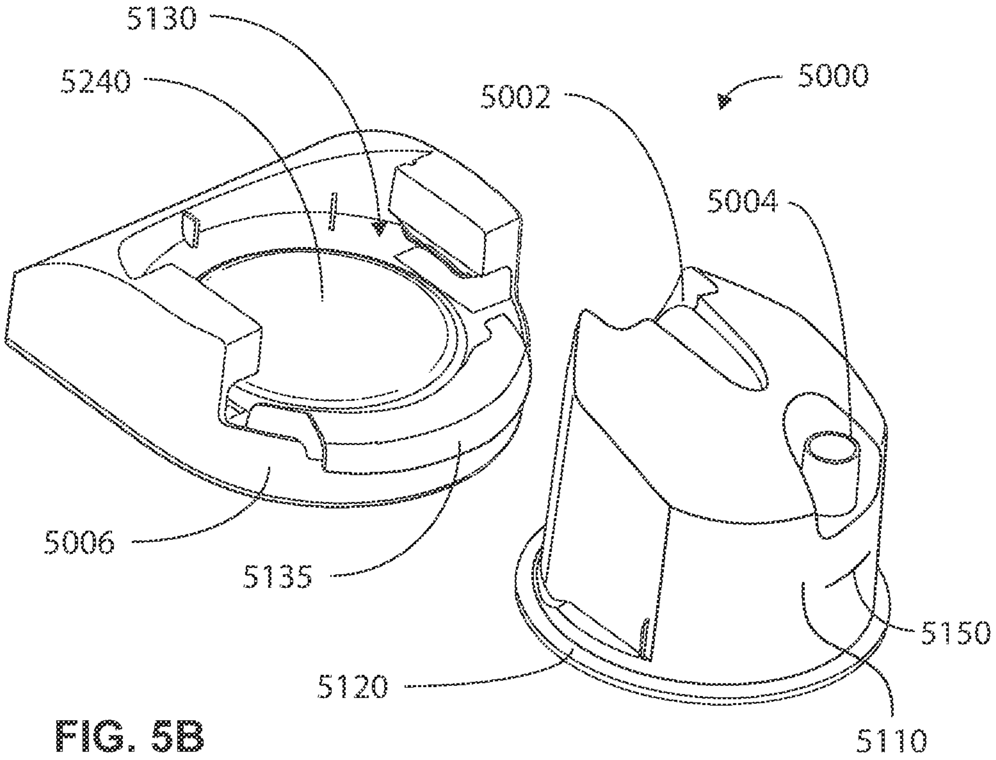

FIG. 5B shows an isometric view of a humidifier in accordance with one form of the present technology, showing a humidifier reservoir 5110 removed from the humidifier reservoir dock 5130.

4.6 Breathing Waveforms

Figure 6:
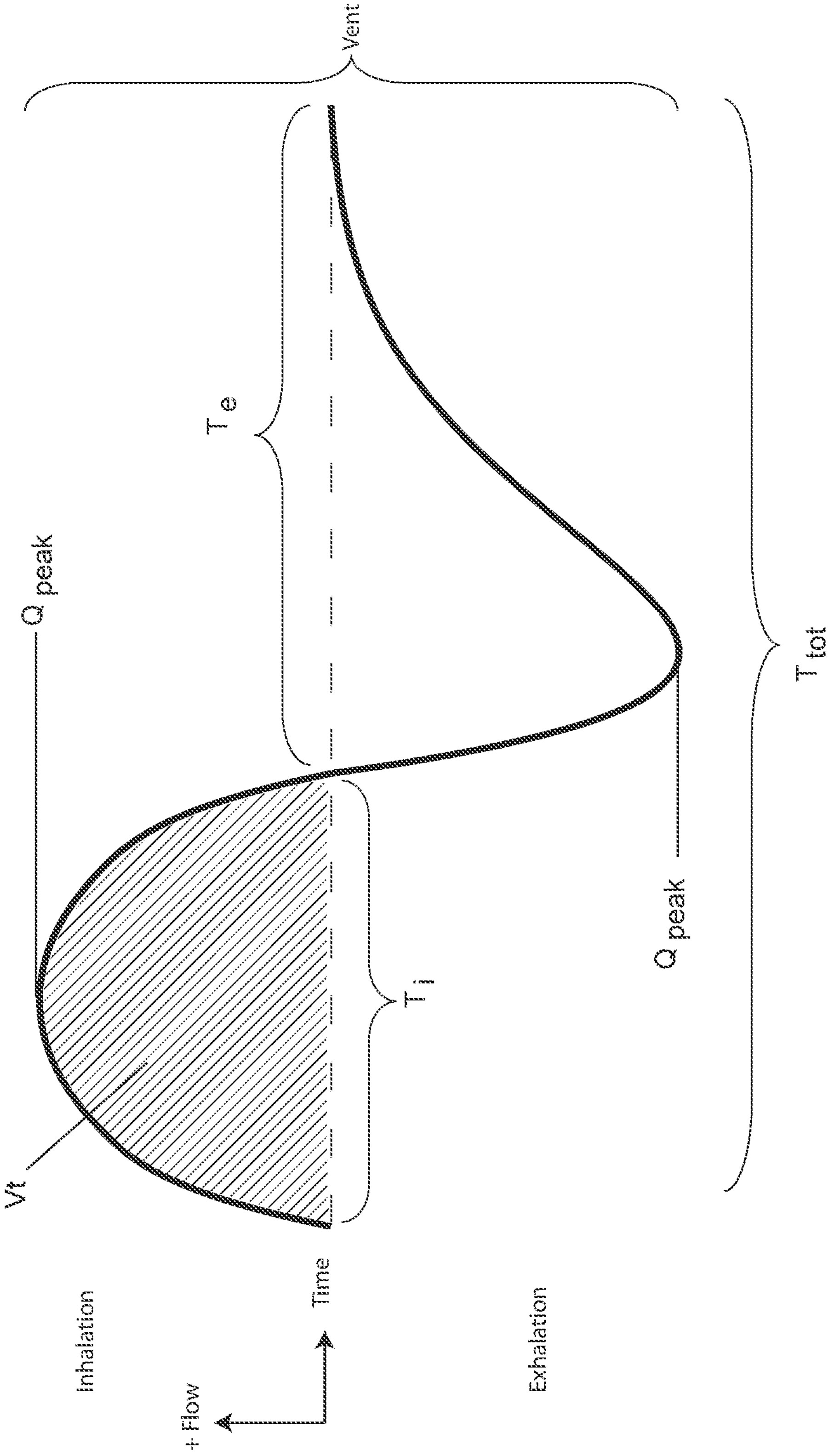

FIG. 6 shows a model typical breath waveform of a person while sleeping.

4.7 Particular Examples of the Present Technology

Figure 7:
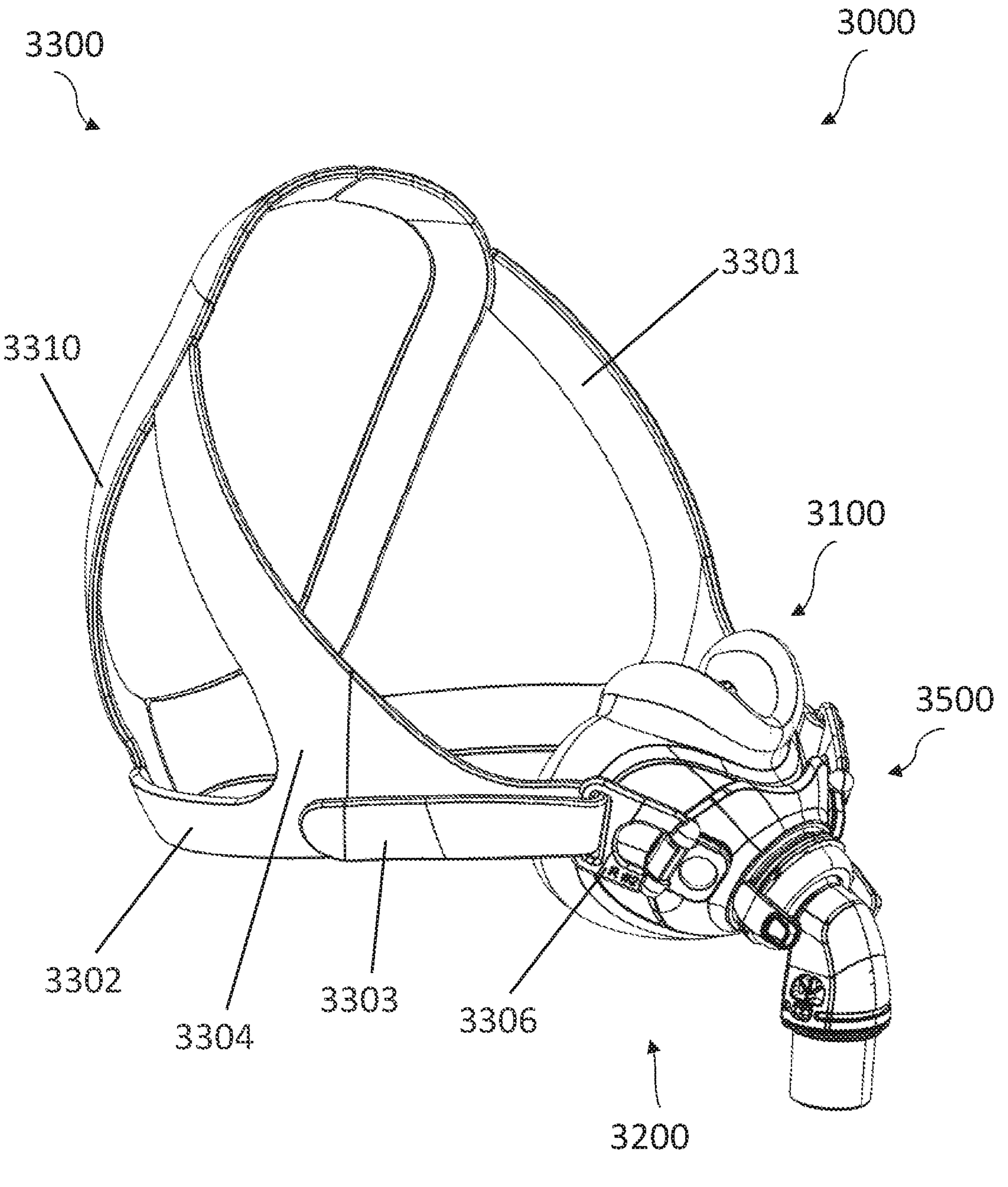

FIG. 7 shows a front perspective view of a patient interface according to one example of the present technology.

Figures 1, 7:
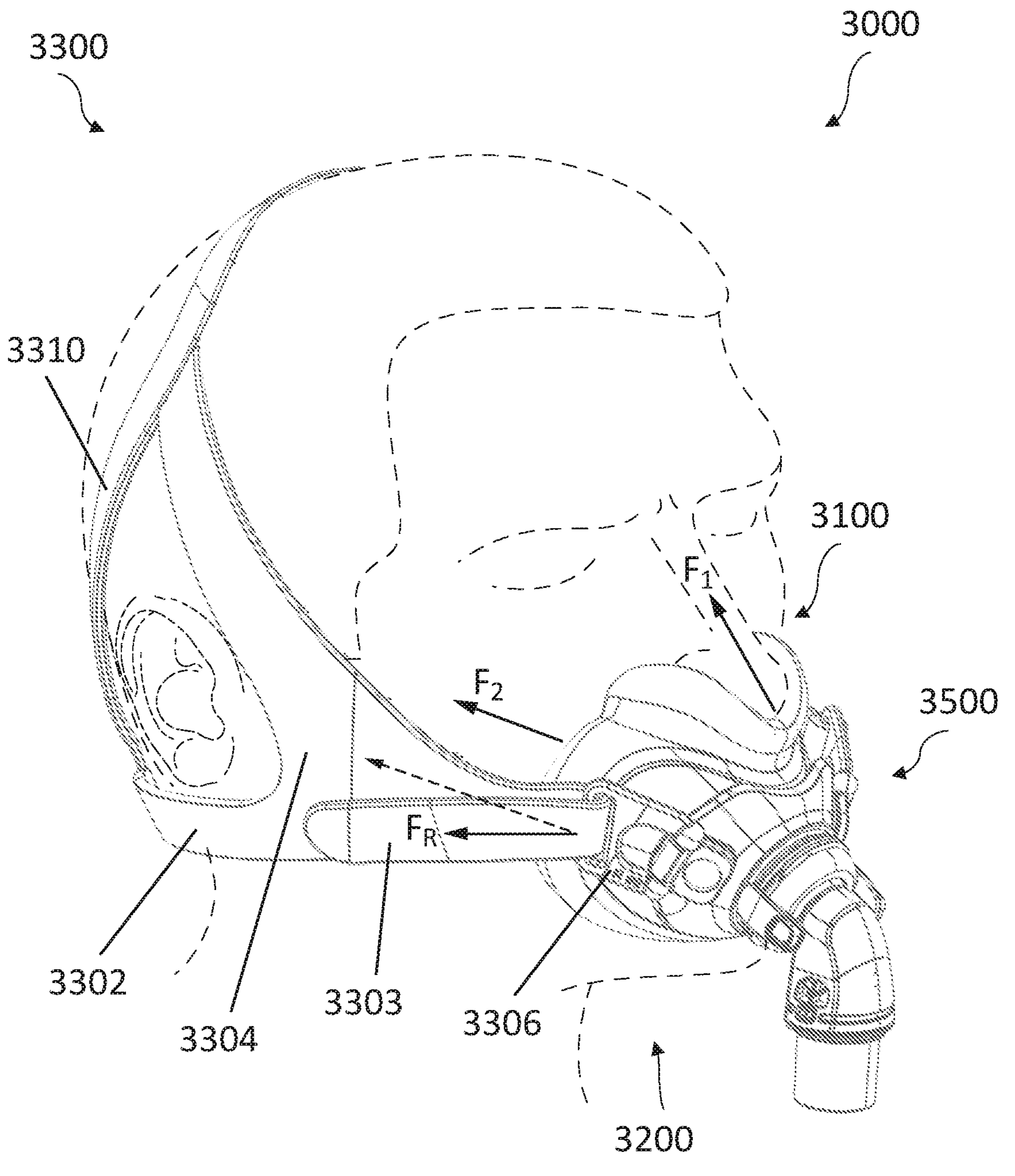

FIG. 7-1 shows a front perspective view of the patient interface of FIG. 7, while worn by a patient.

Figure 8:
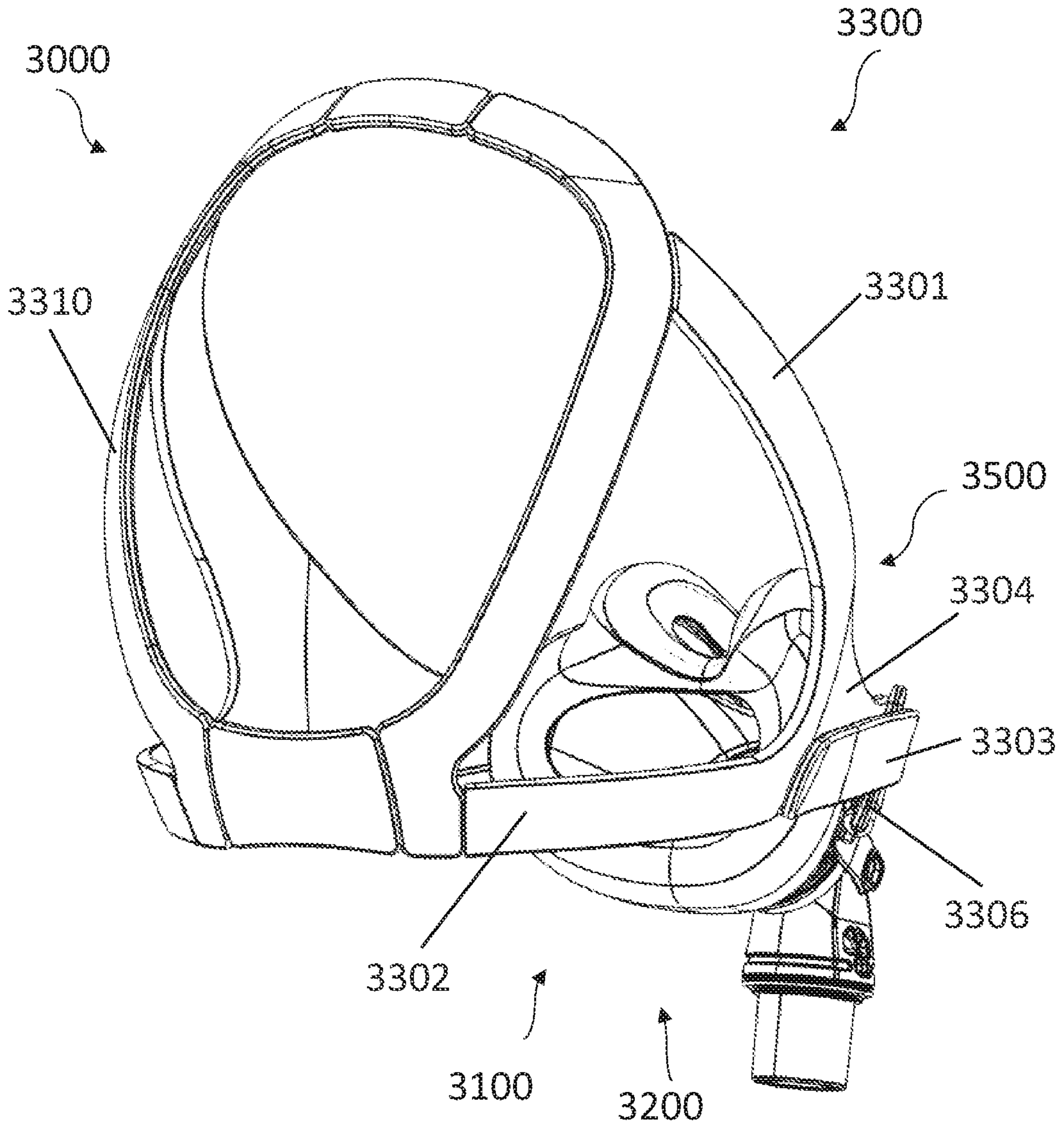

FIG. 8 shows a back perspective view of the patient interface of FIG. 7.

Figure 9:
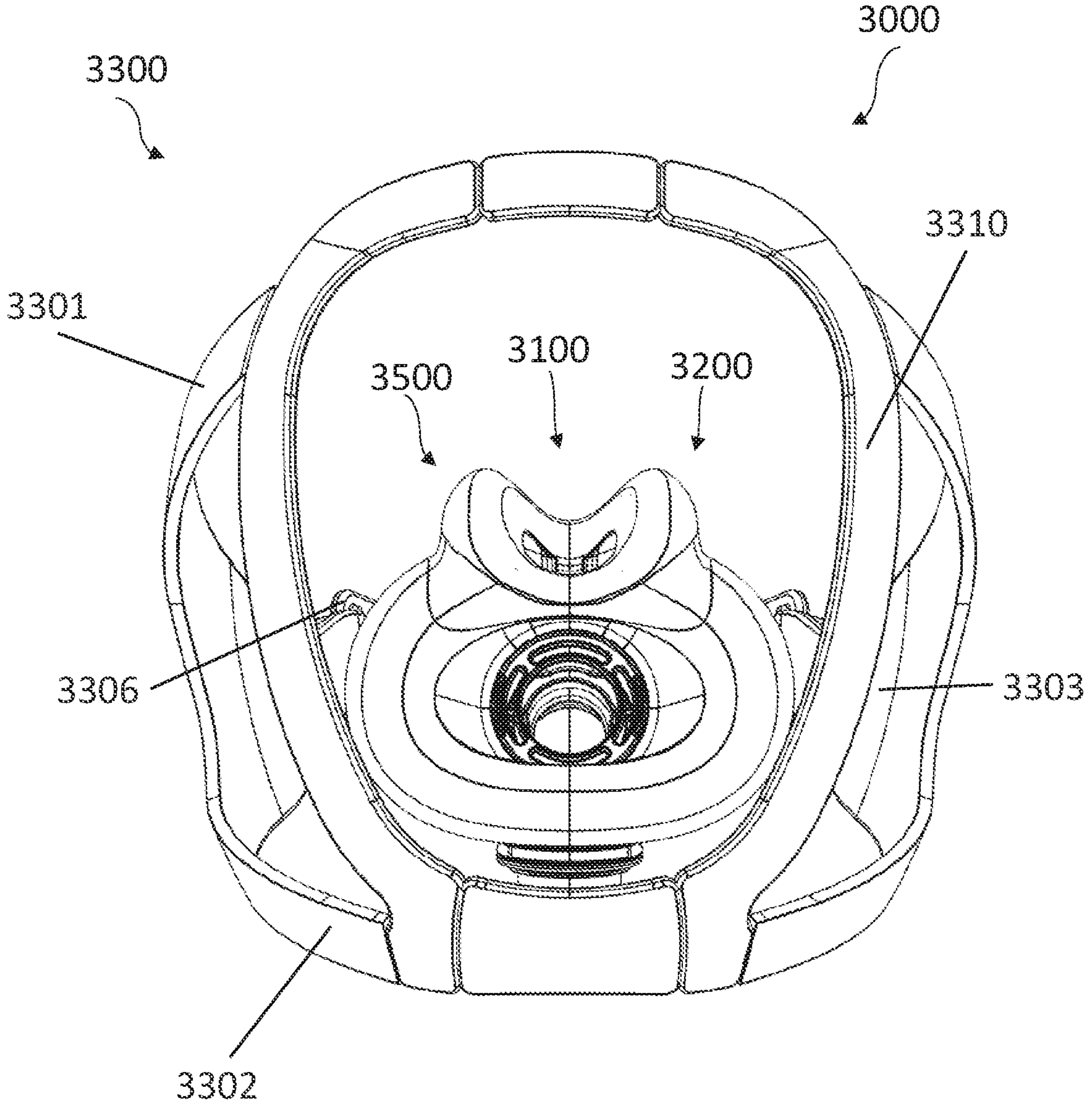

FIG. 9 shows a back view of the patient interface of FIG. 7.

Figure 10:
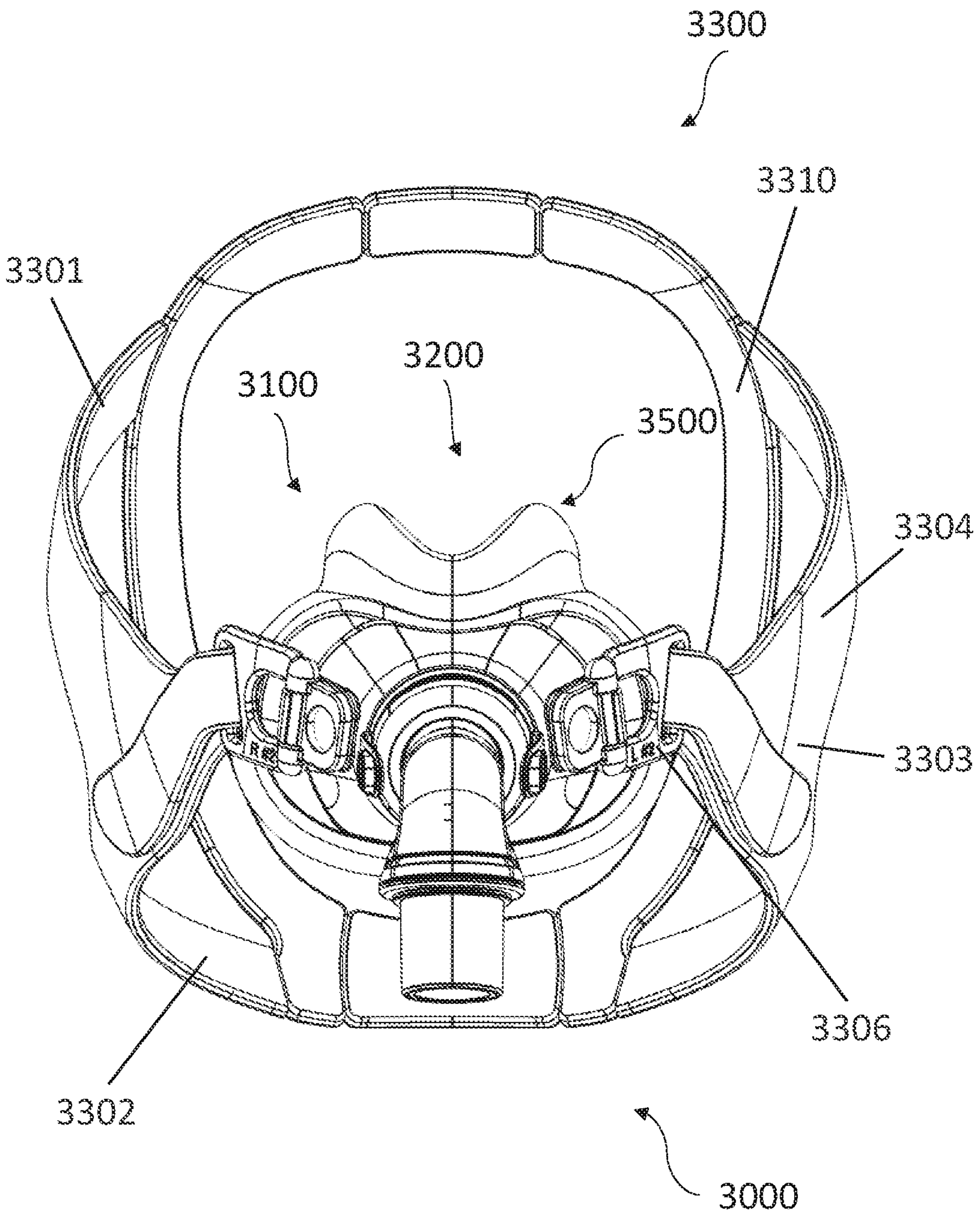

FIG. 10 shows a front view of the patient interface of FIG. 7.

Figure 11:
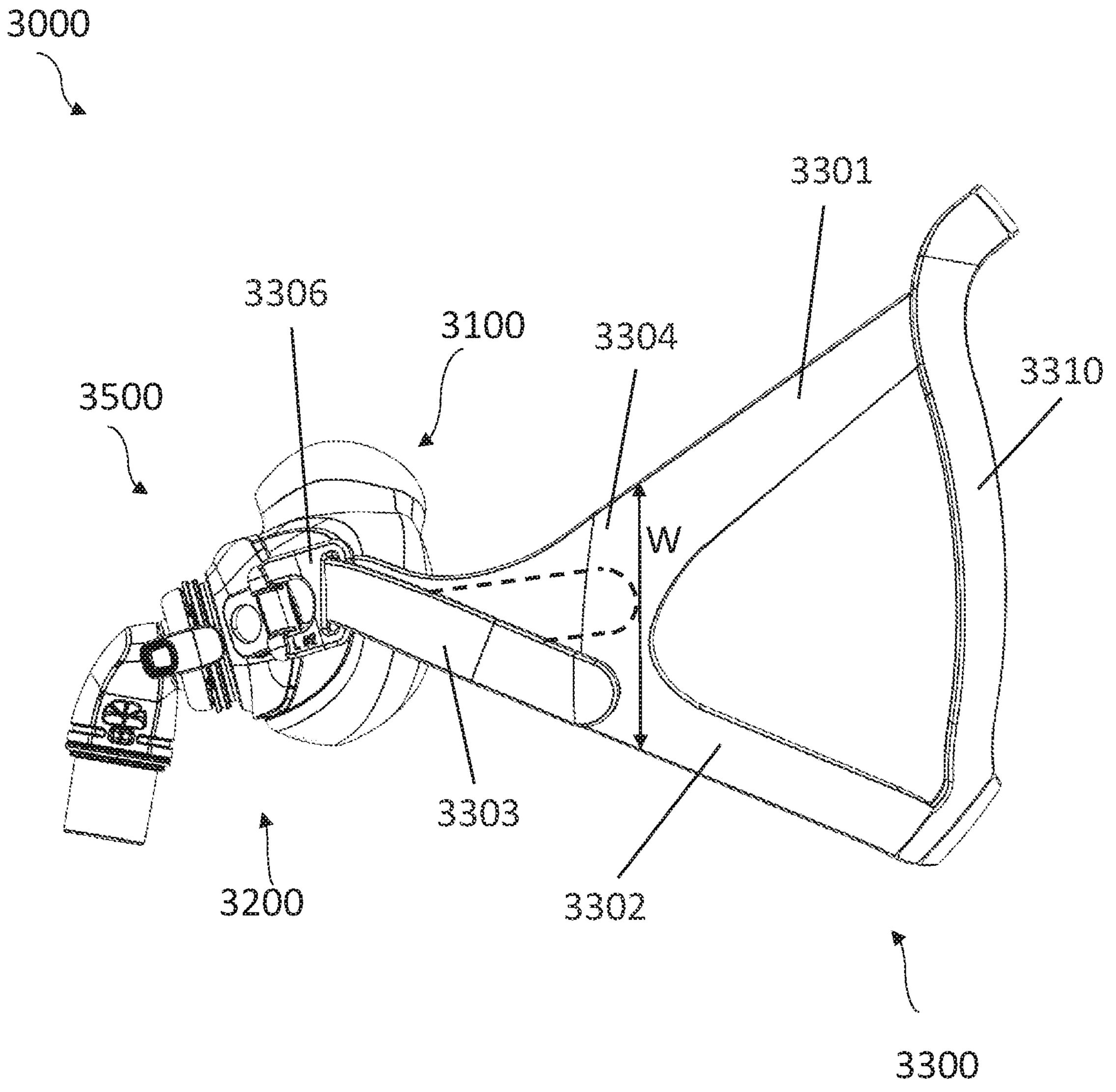

FIG. 11 shows a left side view of the patient interface of FIG. 7.

Figure 12:
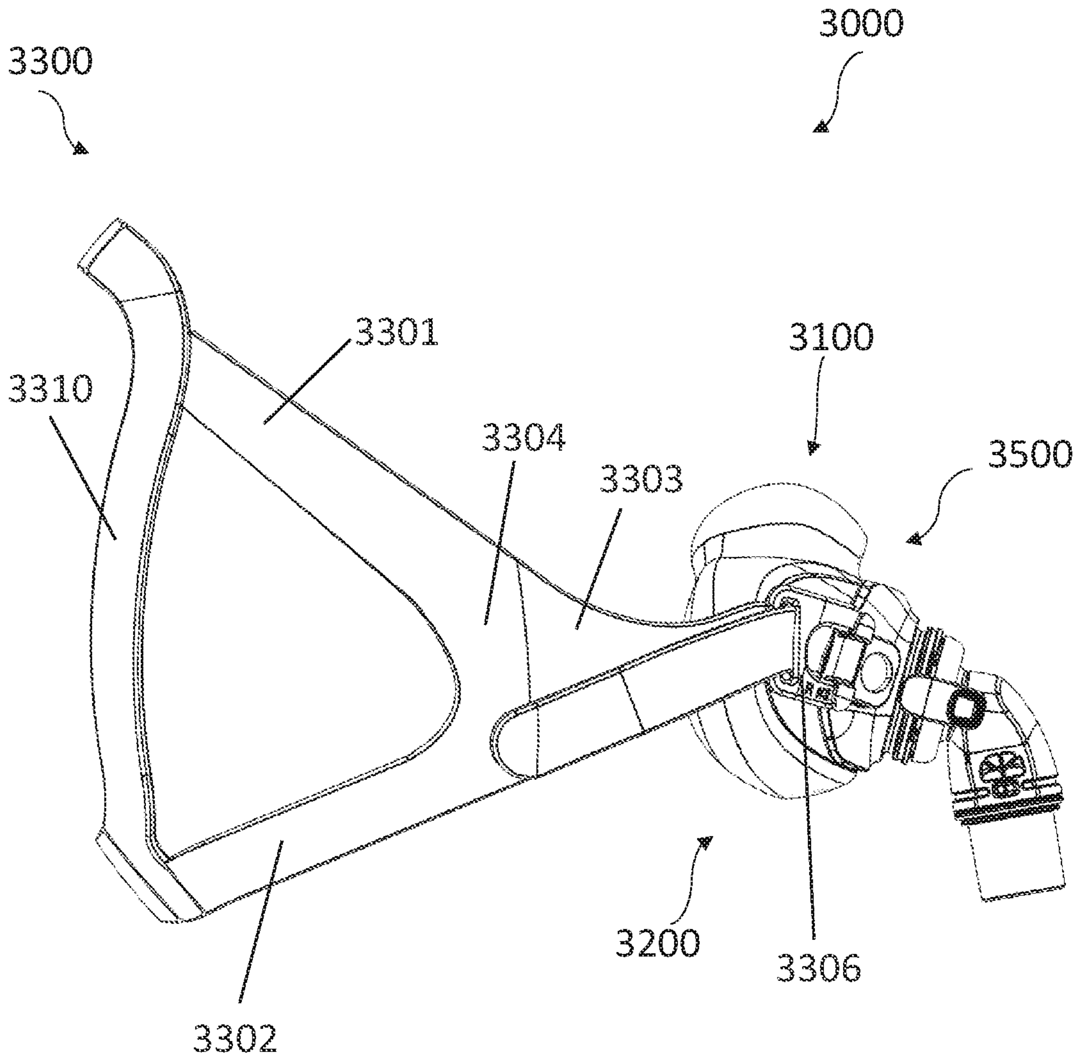

FIG. 12 shows a right-side view of the patient interface of FIG. 7.

Figure 13:
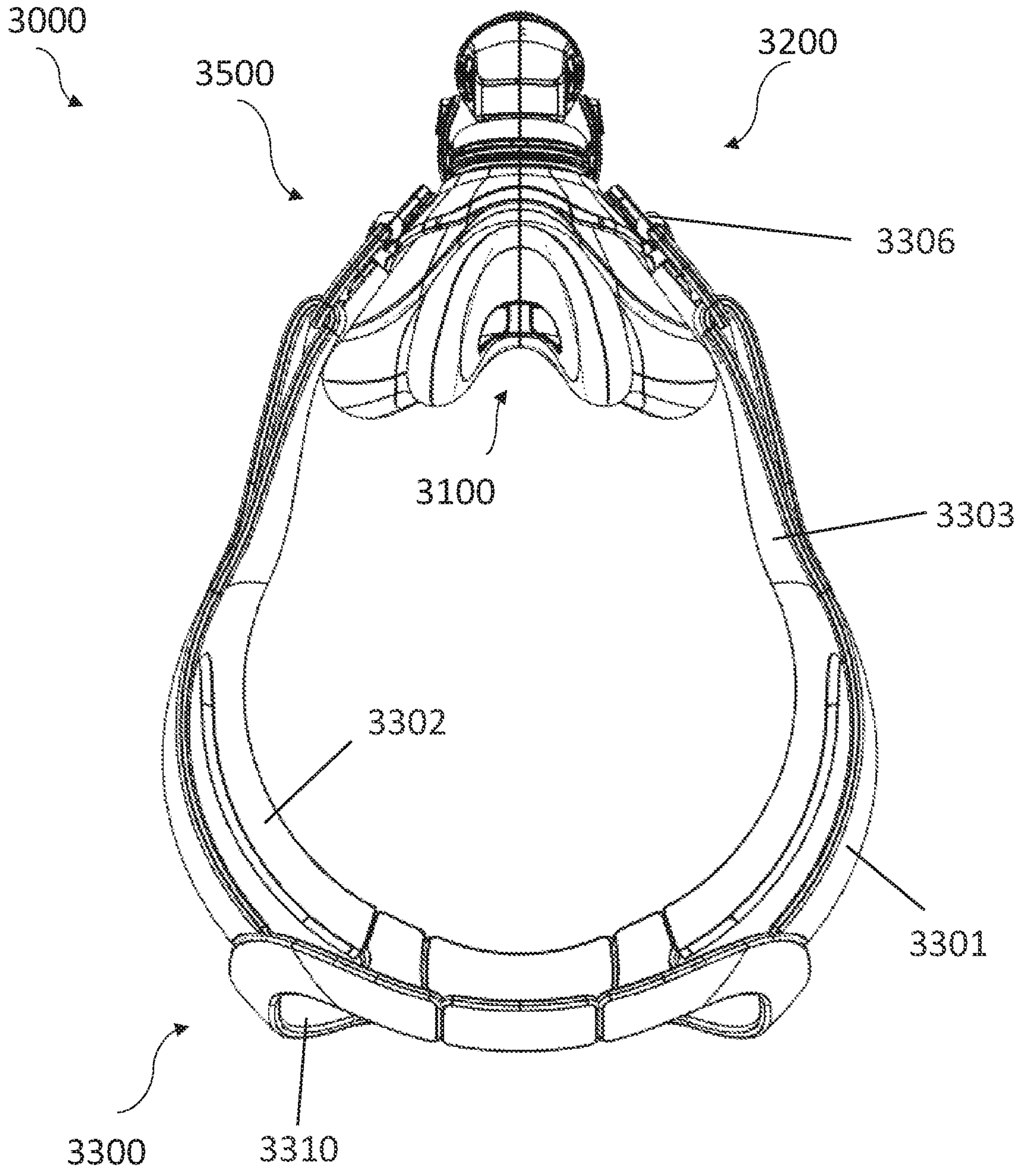

FIG. 13 shows a top view of the patient interface of FIG. 7.

Figure 14:
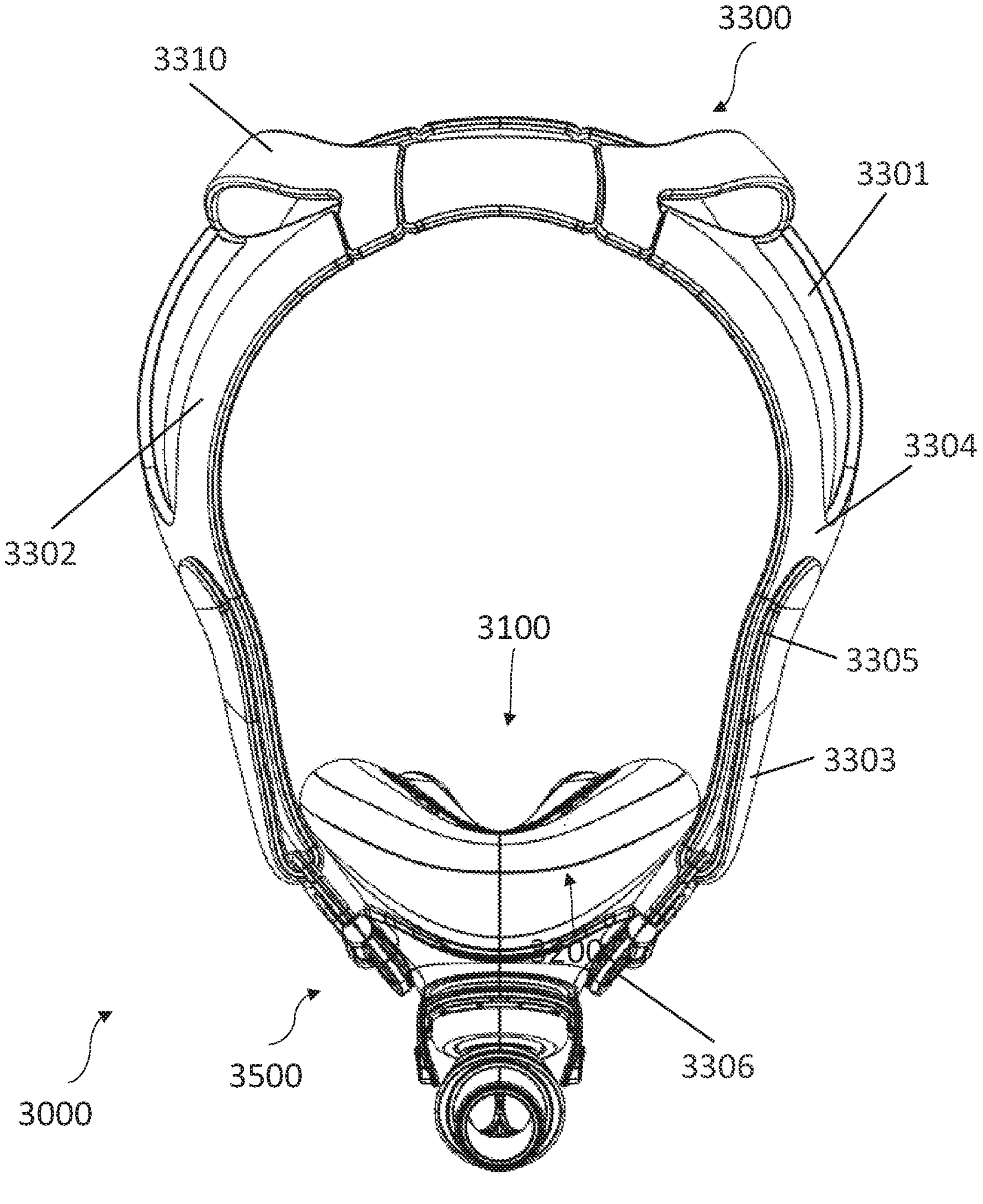

FIG. 14 shows a bottom view of the patient interface of FIG. 7.

Figure 15:
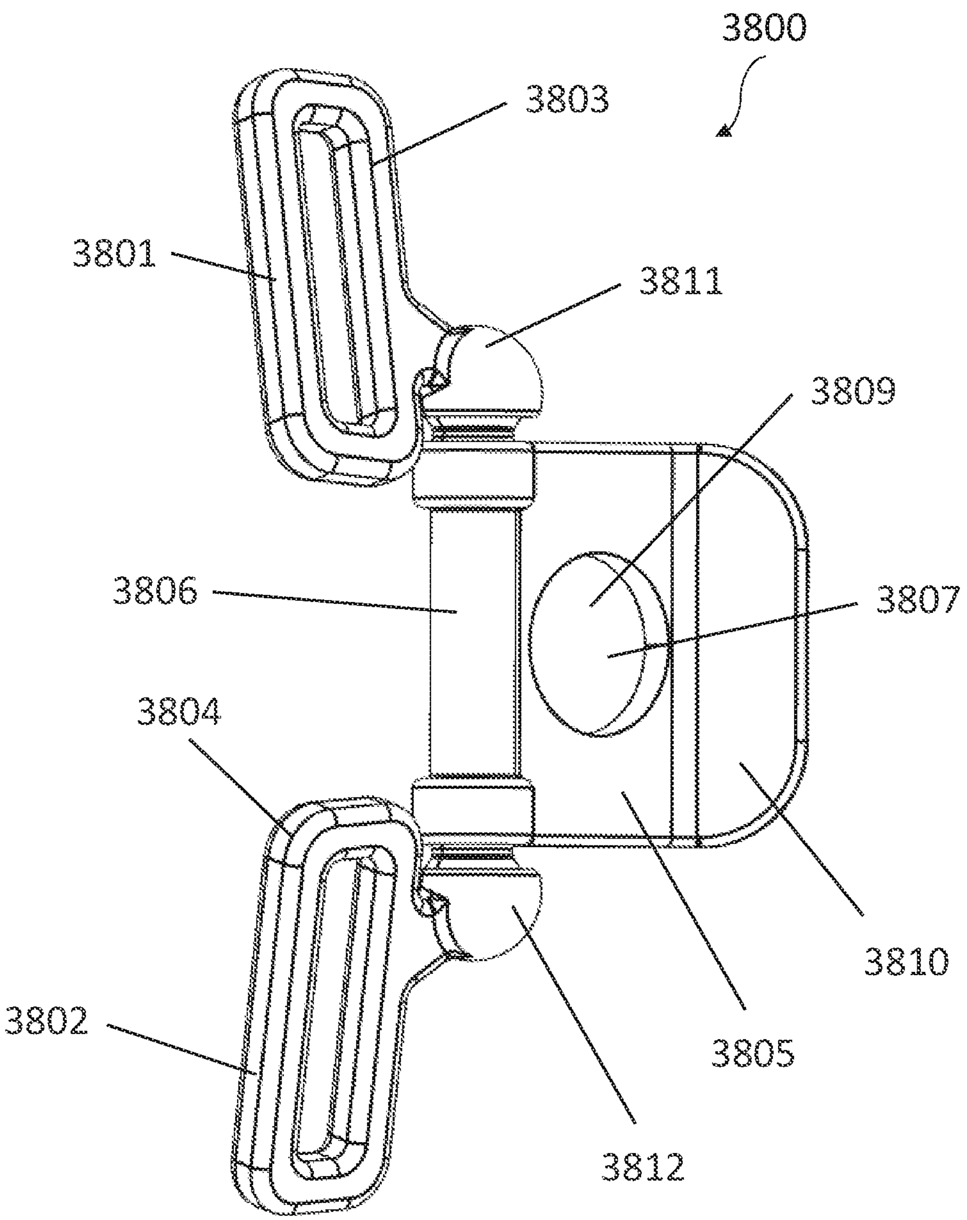

FIG. 15 shows a front perspective view of a connection member according to one example of the present technology.

Figure 16:
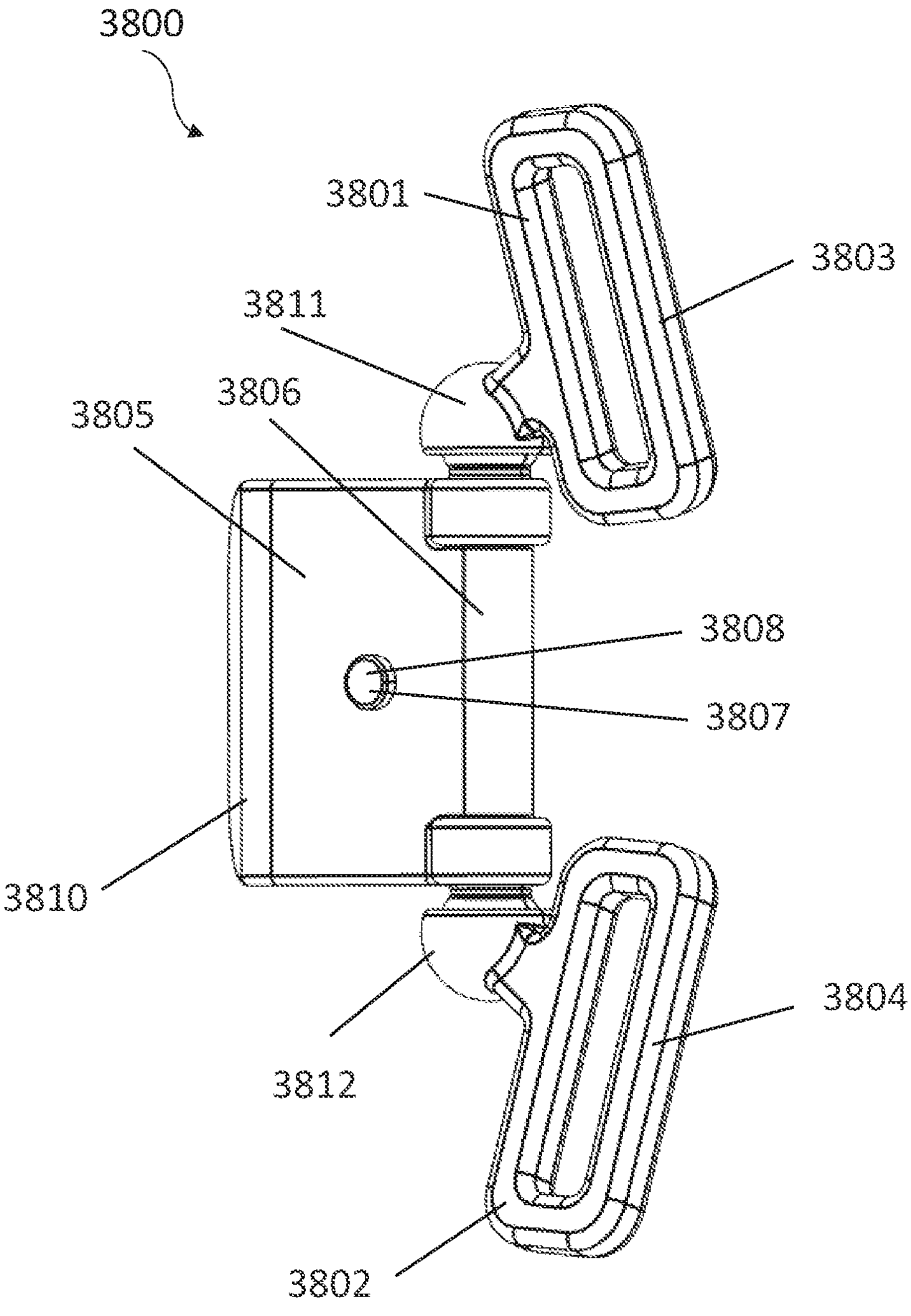

FIG. 16 shows a back perspective view of the connection member of FIG. 15.

Figure 17:
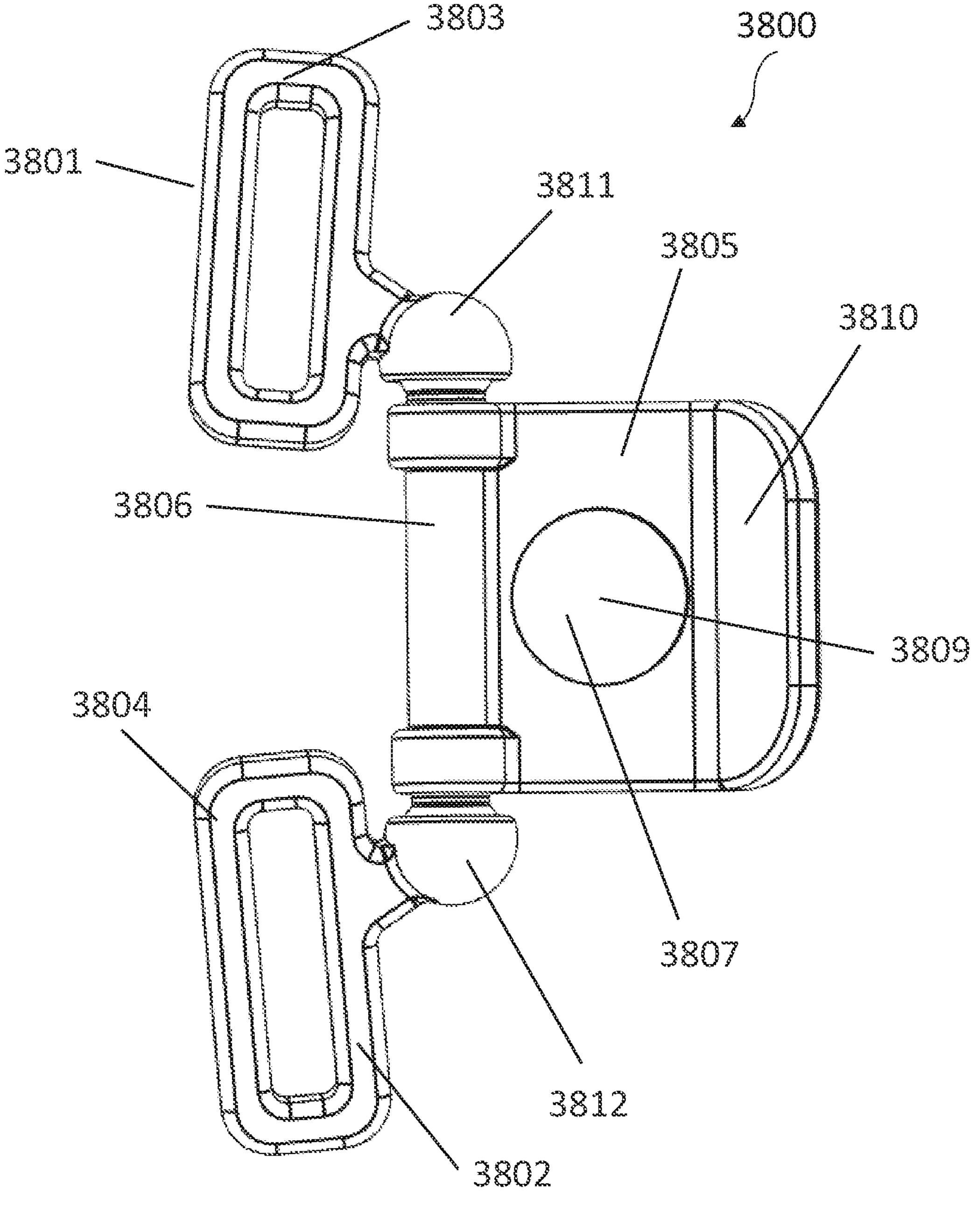

FIG. 17 shows a front view of the connection member of FIG. 15.

Figure 18:
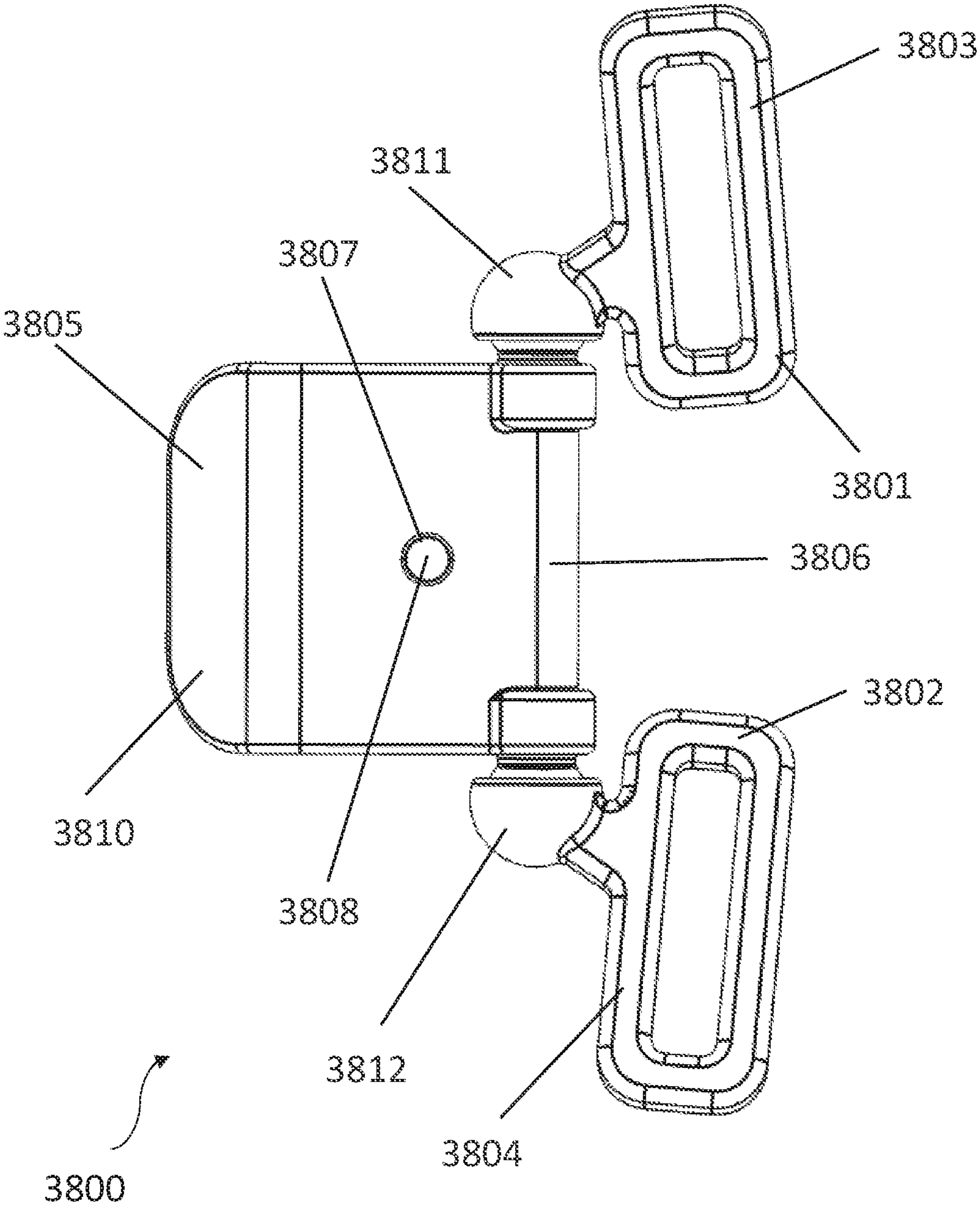

FIG. 18 shows a back view of the connection member of FIG. 15.

Figure 19:
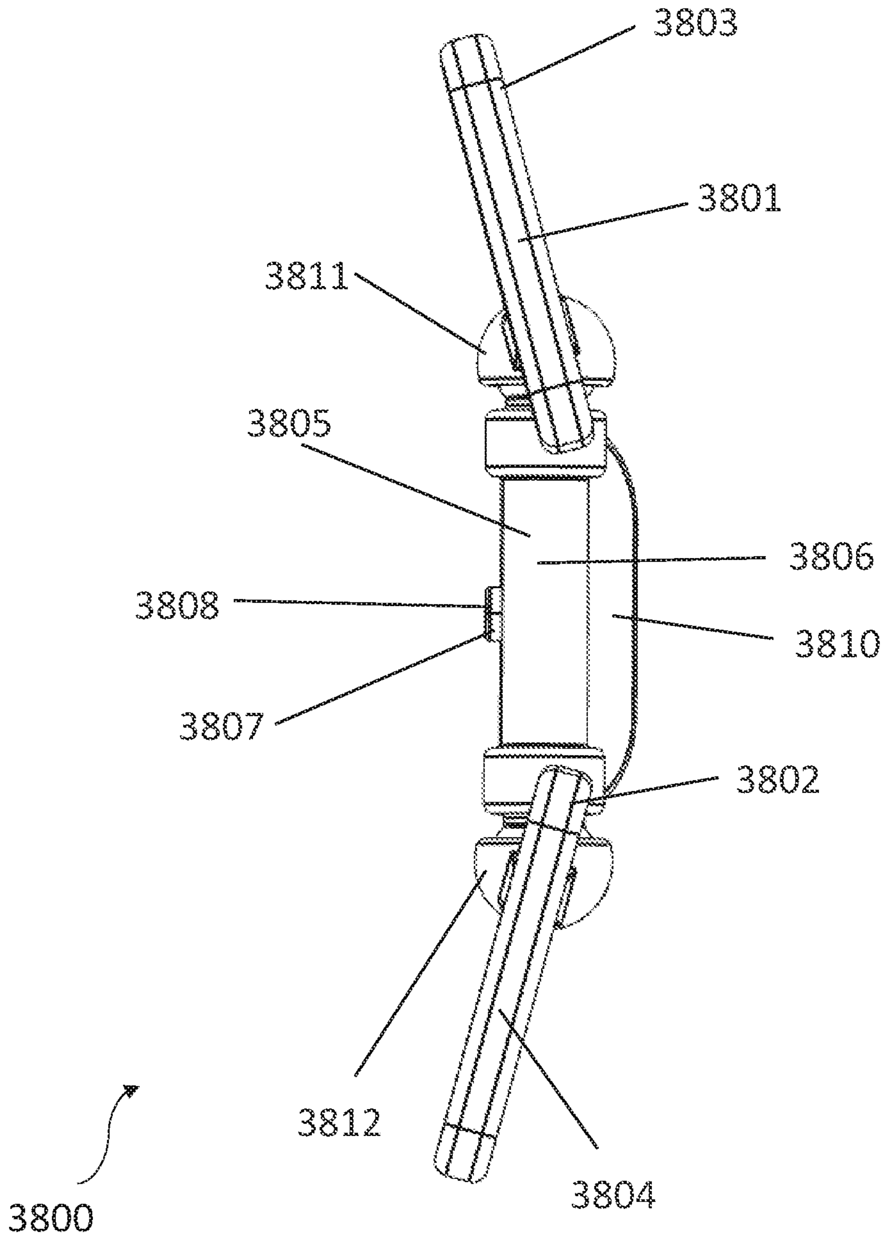

FIG. 19 shows a left side view of the connection member of FIG. 15.

Figure 20:
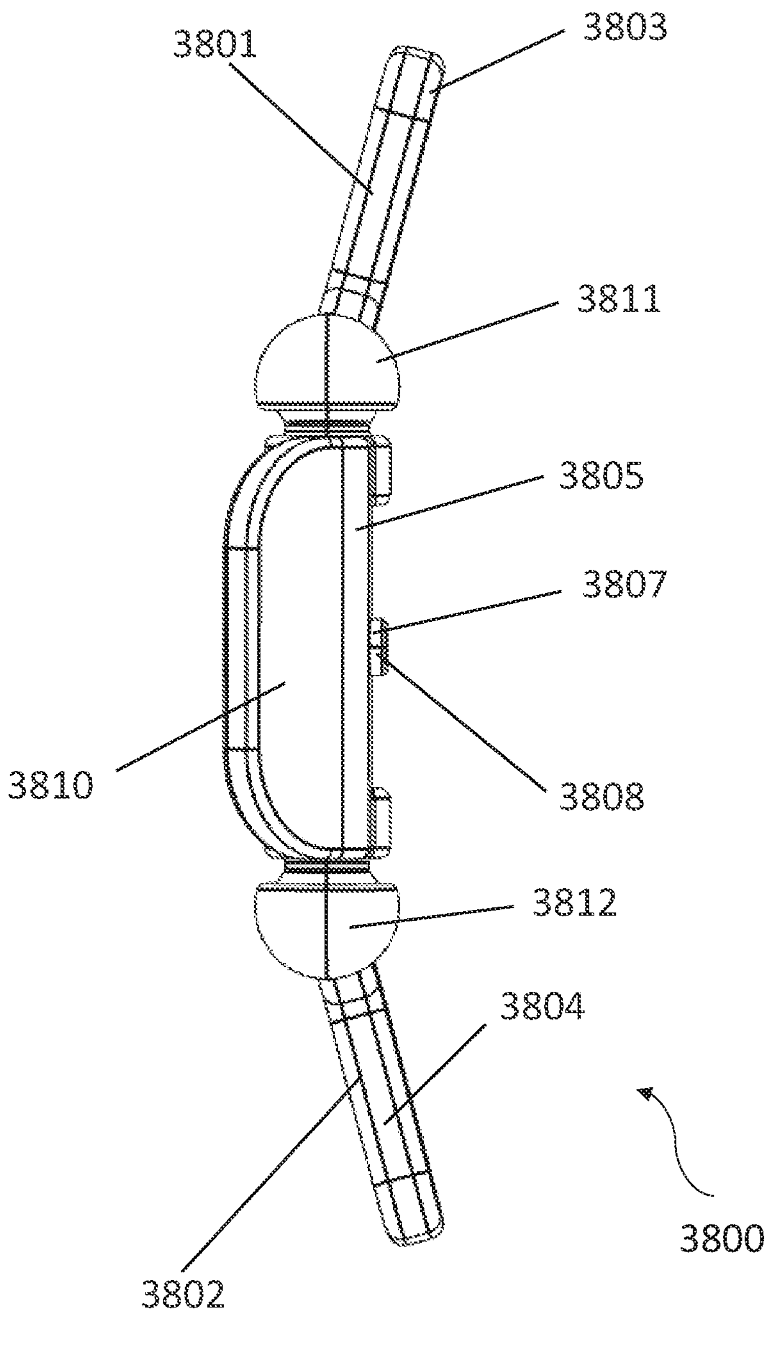

FIG. 20 shows a right side view of the connection member of FIG. 15.

Figure 21:
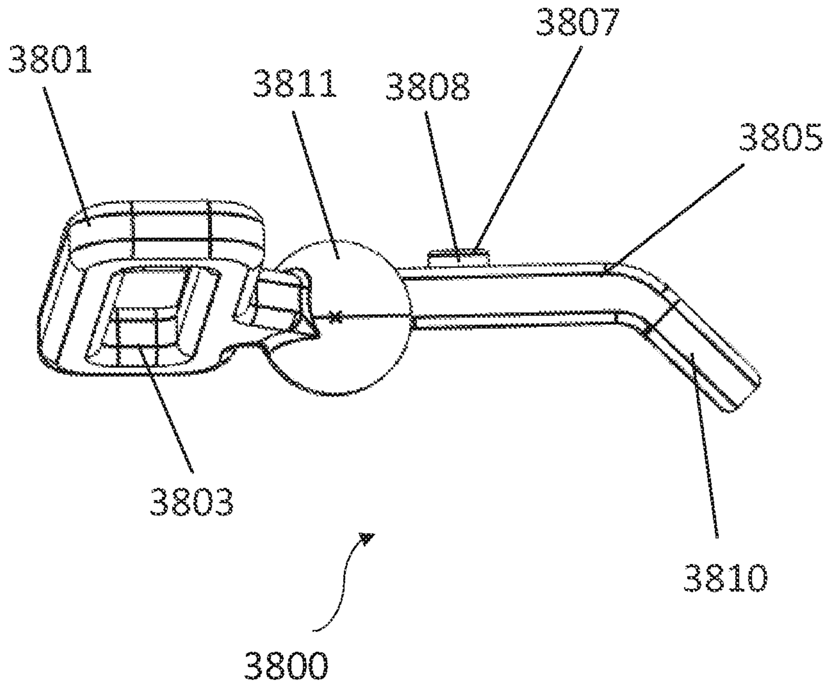

FIG. 21 shows a top view of the connection member of FIG. 15.

Figure 22:
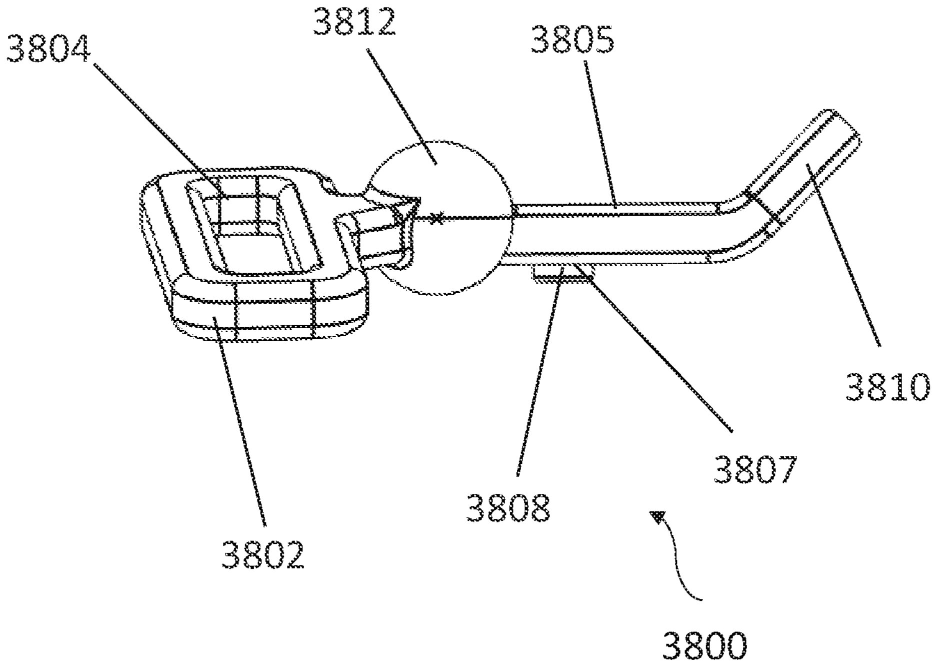

FIG. 22 shows a bottom view of the connection member of FIG. 15.

Figure 23:
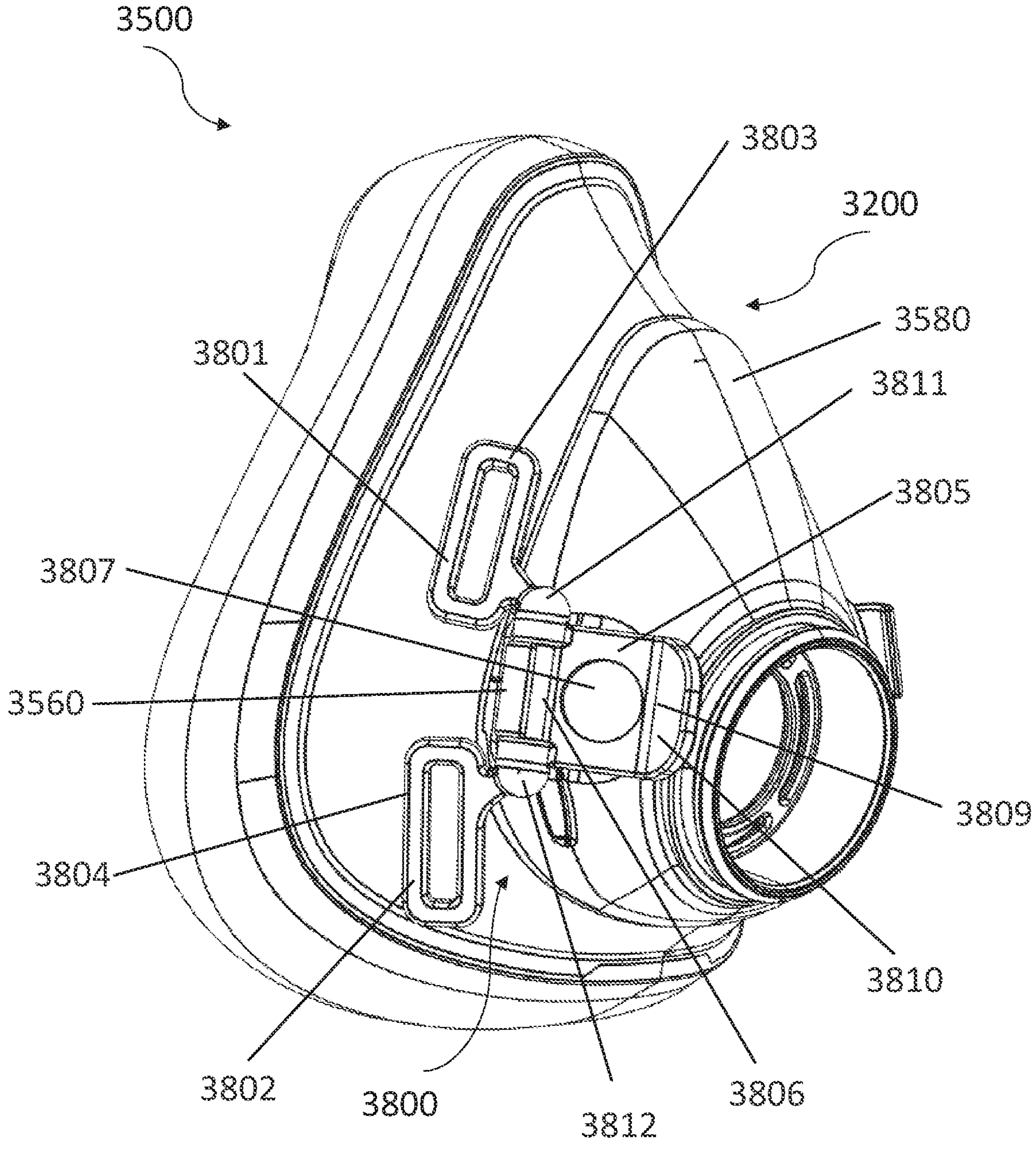
Figures 1, 23:
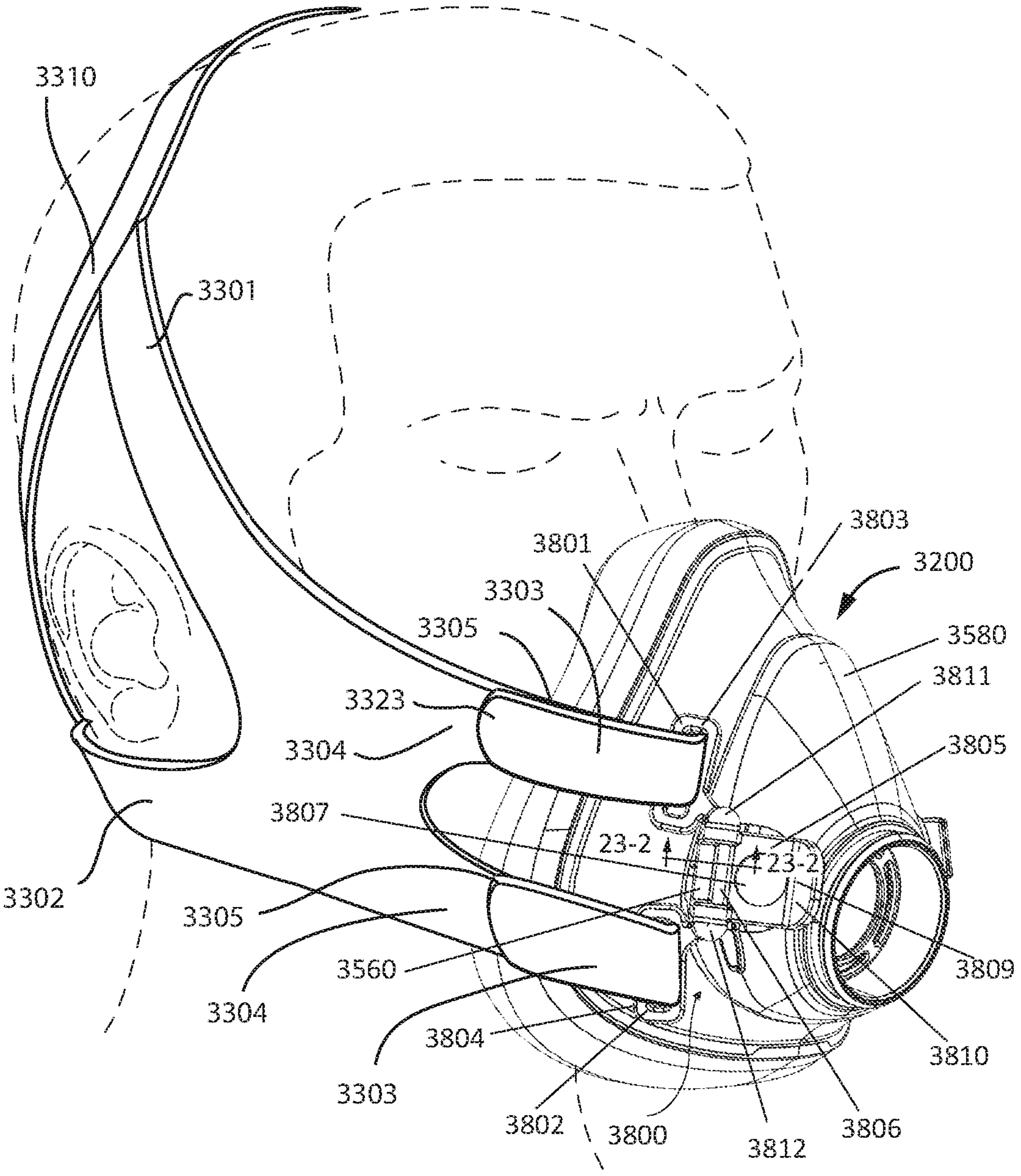

FIG. 23 shows a front perspective view of the connection member of FIG. 15 connected to the right side of a full-face mask.

FIG. 23-1 shows a front perspective view of a patient wearing the full-face mask of FIG. 23.

Figures 2, 23:
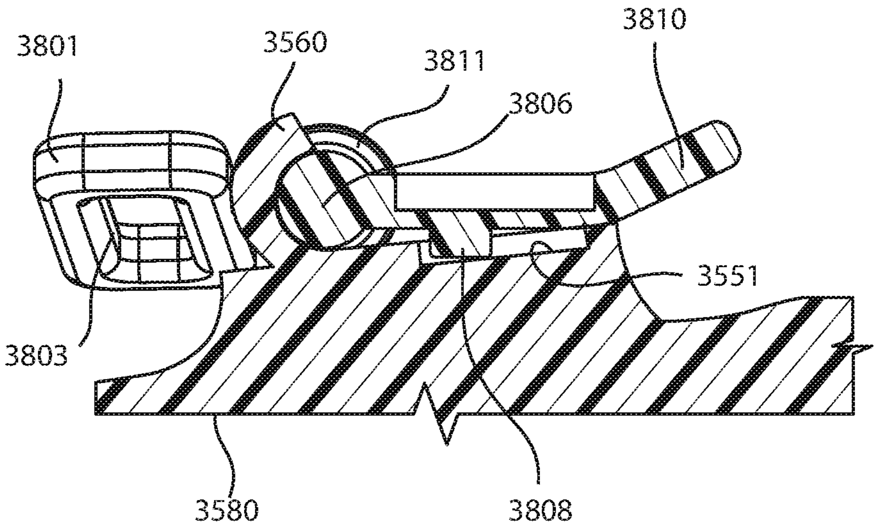

FIG. 23-2 shows a cross-sectional view of the full-face mask of FIG. 23 viewed along line 23-2-23-2, and illustrating a connection between the connection member and the full-face mask.

Figure 24:
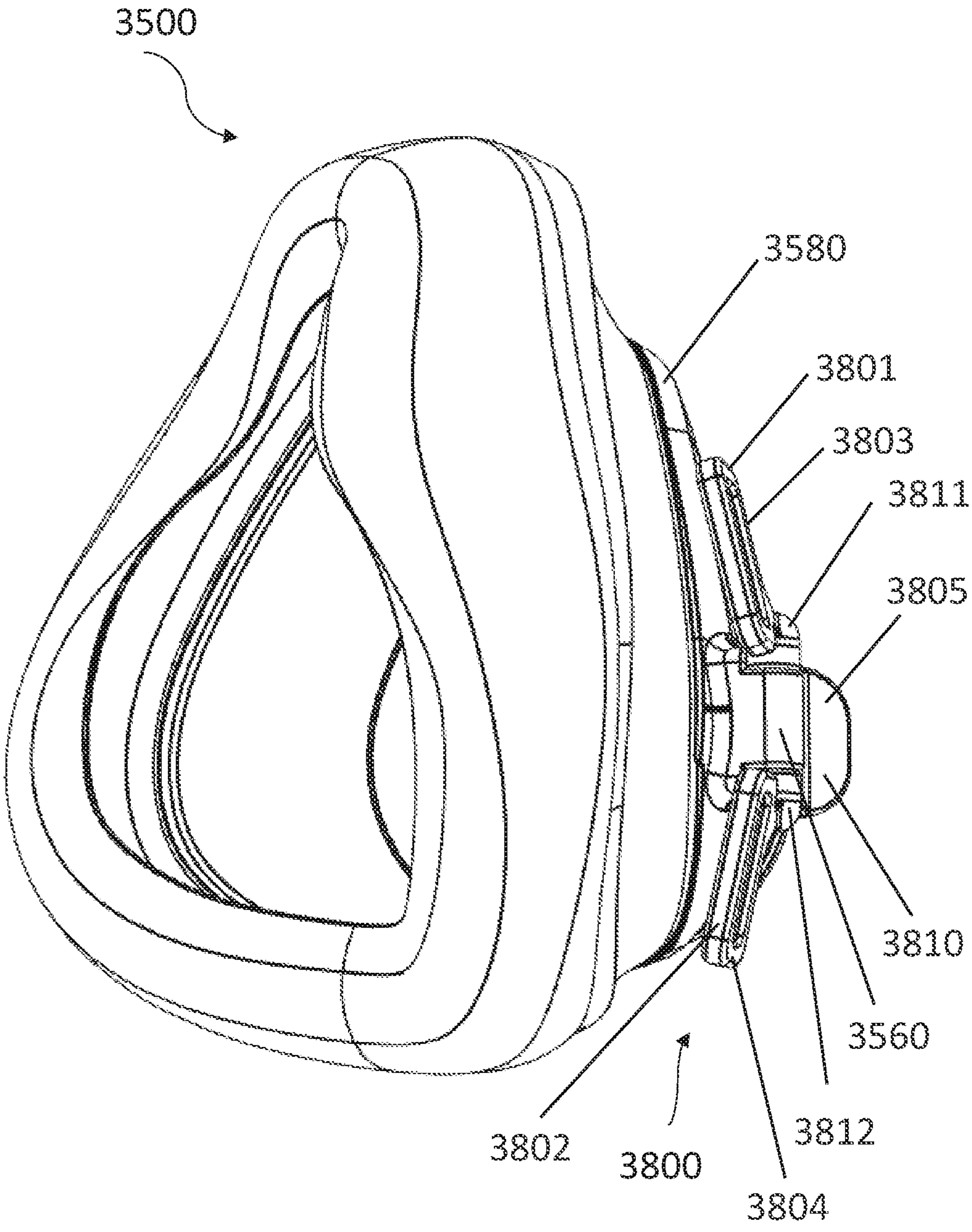

FIG. 24 shows a back perspective view of the connection member of FIG. 15 connected to the right side of the full-face mask of FIG. 23.

Figure 25:
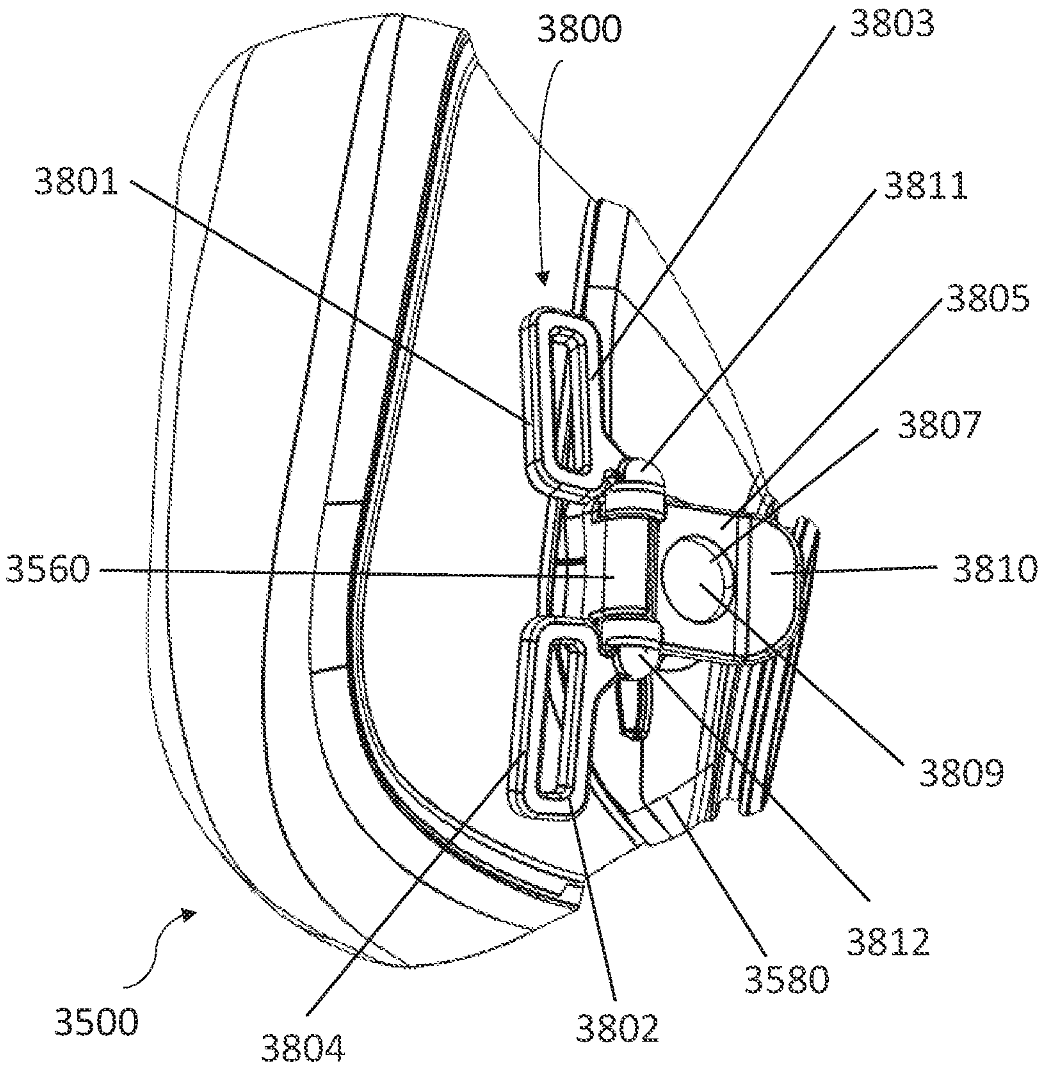

FIG. 25 shows a right side view of the connection member of FIG. 15 connected to the right side of the full-face mask of FIG. 23.

Figure 26:
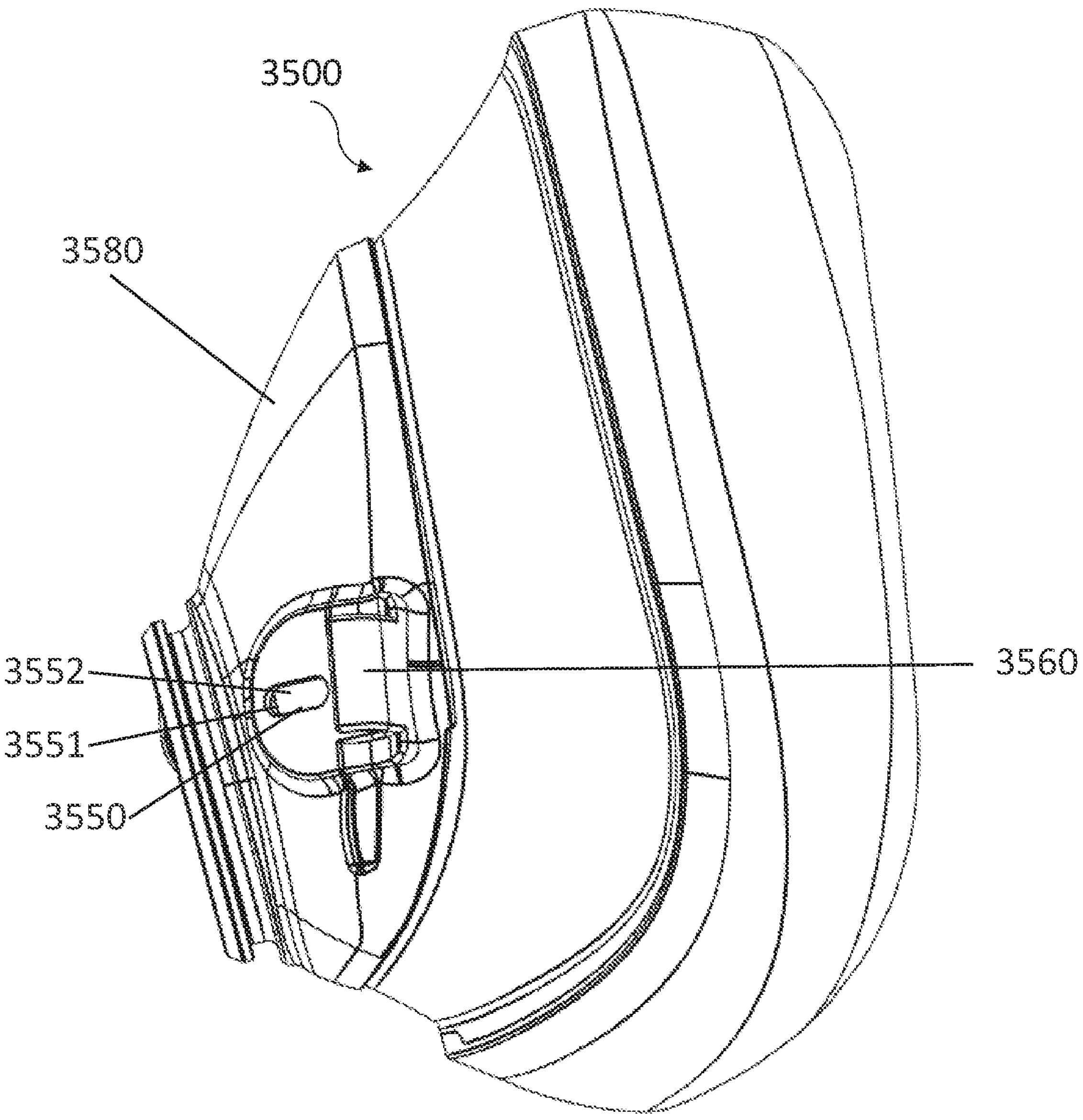

FIG. 26 shows a left side view of the full-face mask of FIG. 23.

Figure 27:
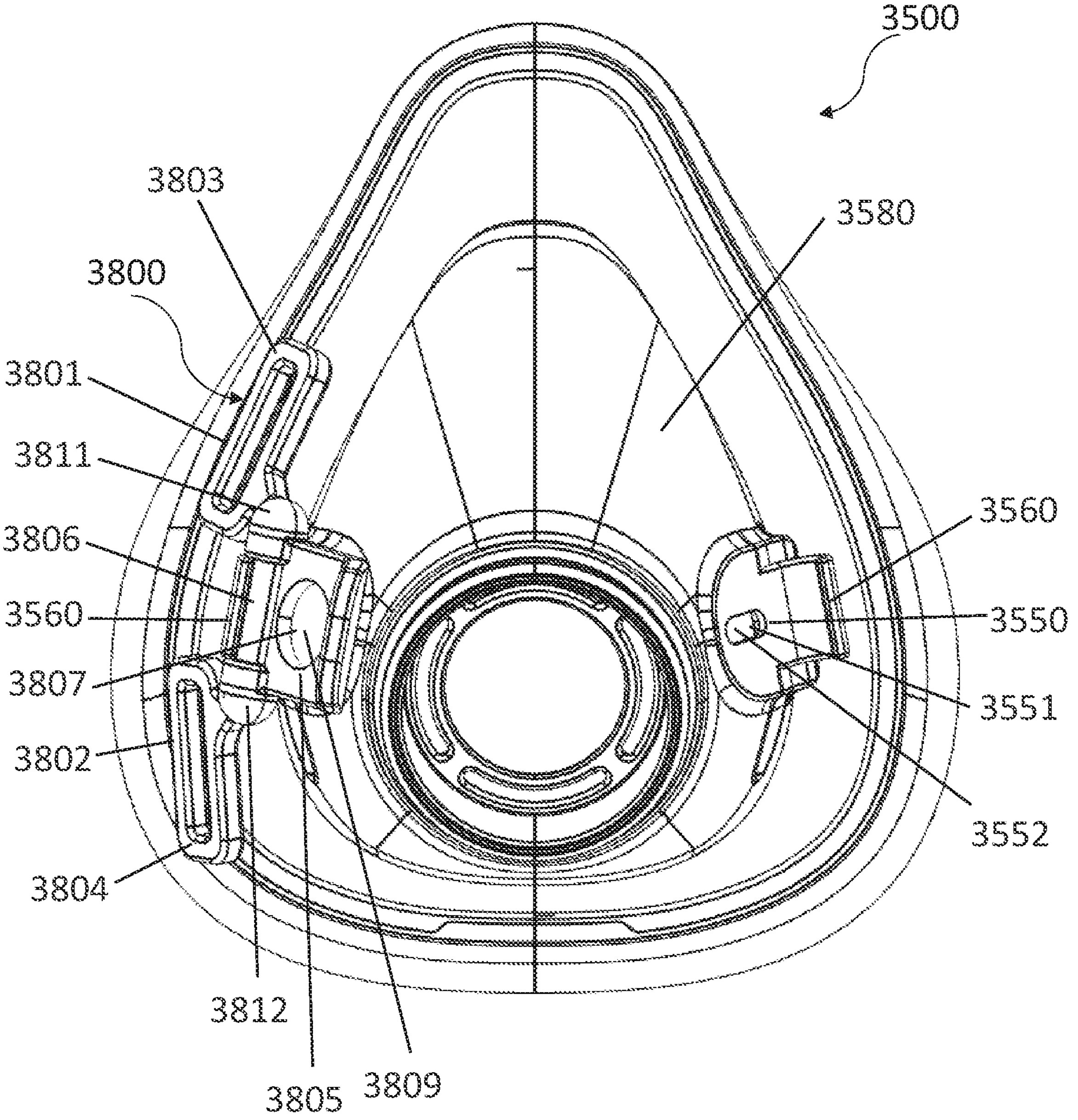

FIG. 27 shows a front view of the full-face mask of FIG. 23 with the connection member of FIG. 15 connected to the right side of the mask.

Figure 28:
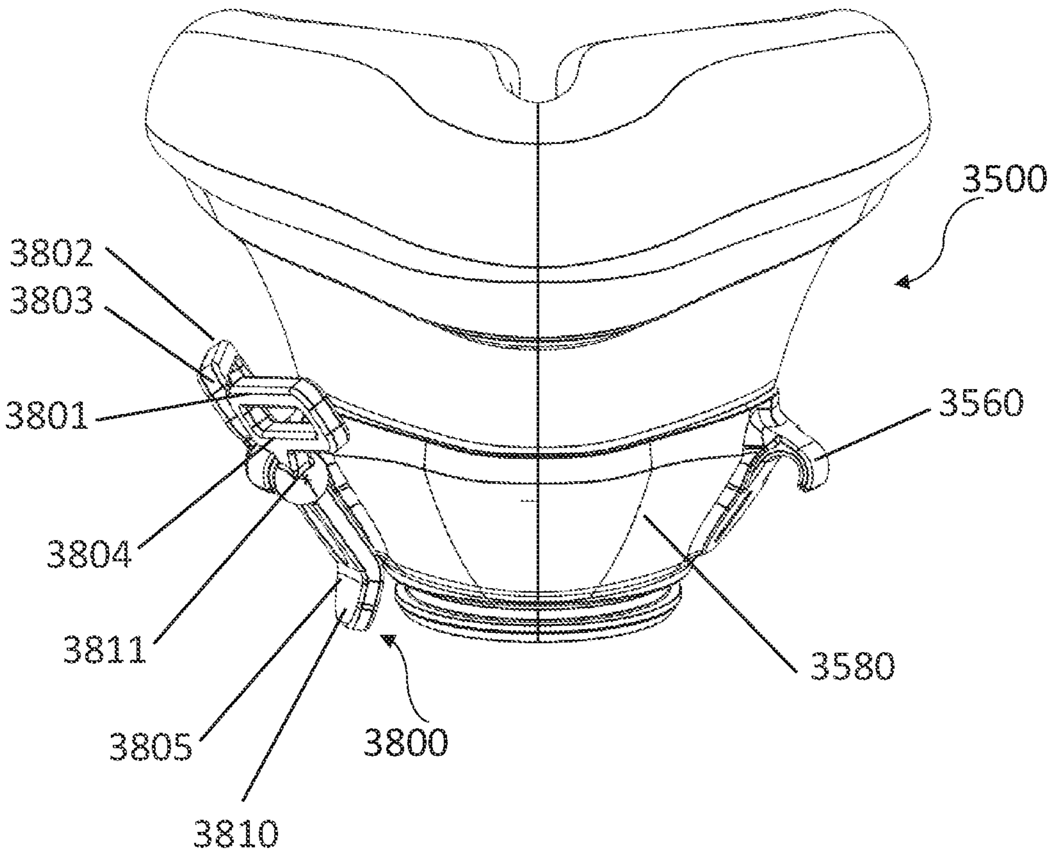

FIG. 28 shows a top view of the full-face mask of FIG. 23.

Figure 29:
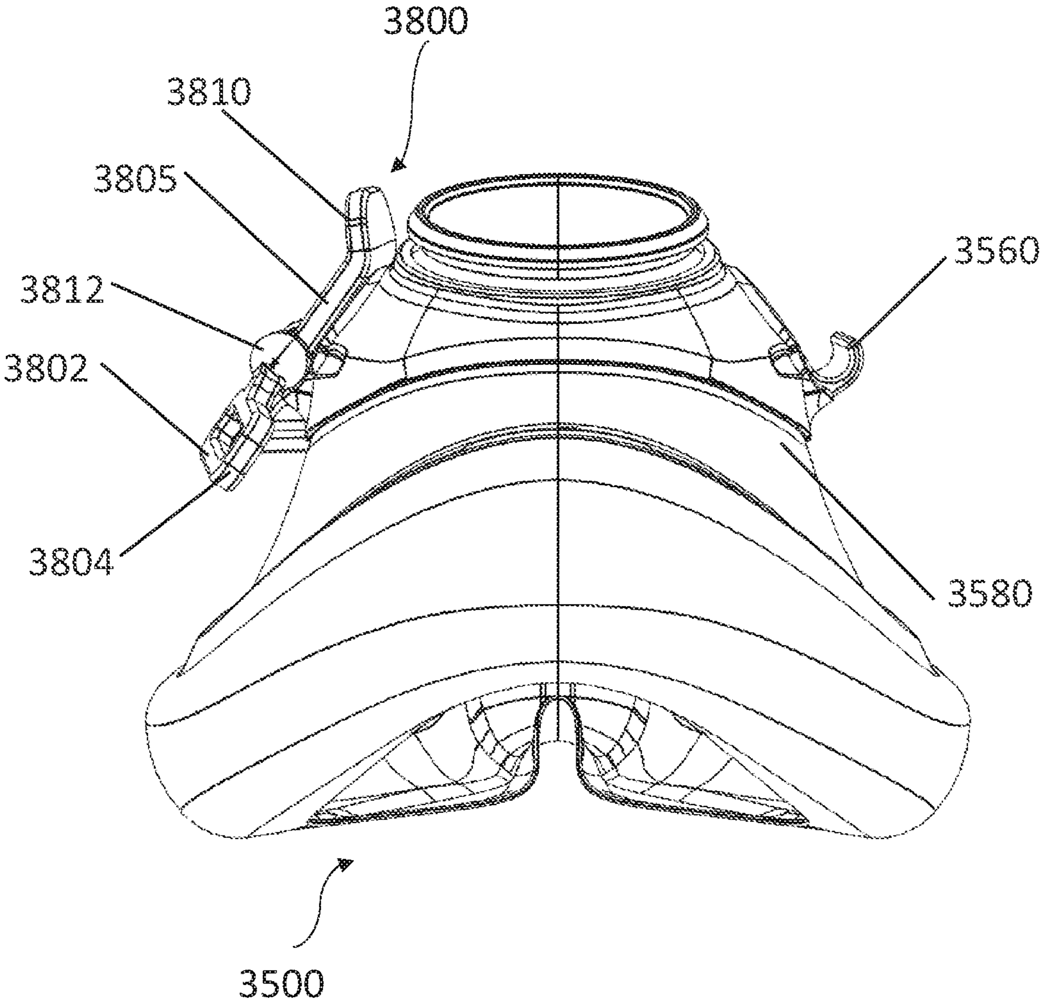

FIG. 29 shows a bottom view of the full-face mask of FIG. 23.

Figure 30:
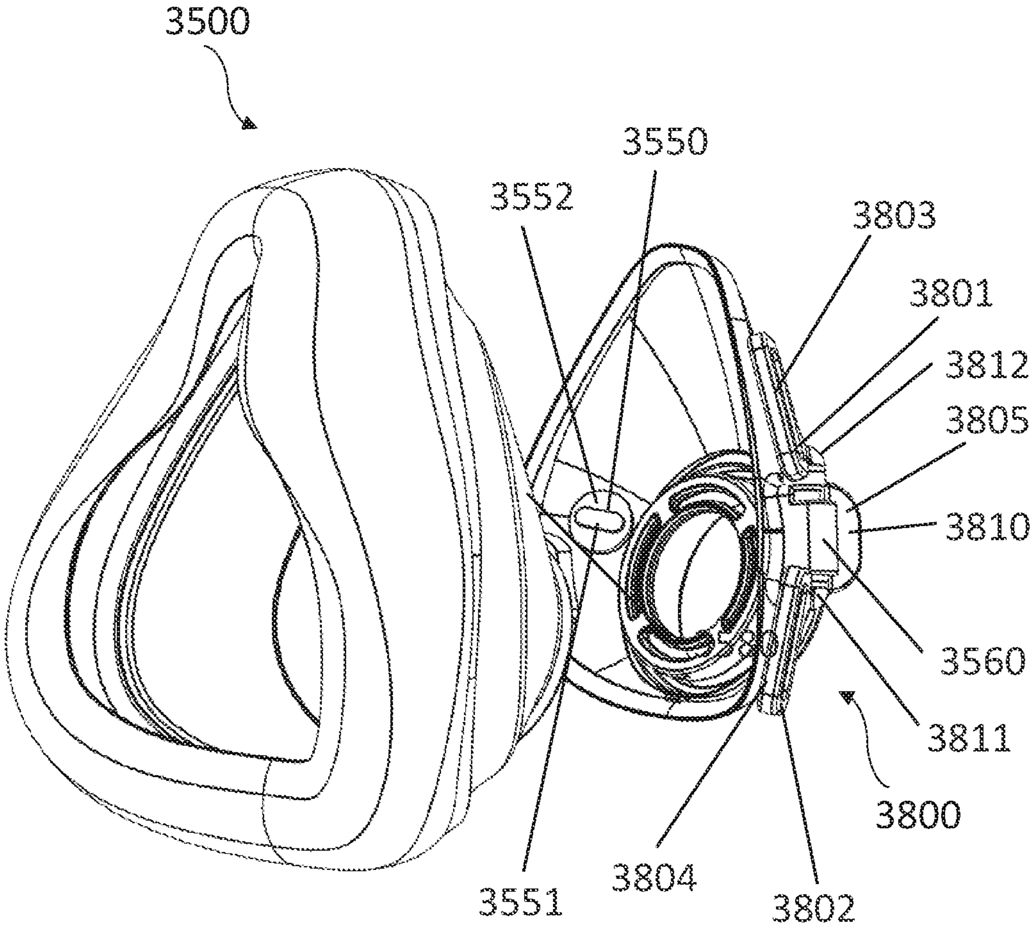

FIG. 30 shows an exploded view of mask and connection member of FIG. 27.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. A flow of pressurized air can flow into the plenum chamber 3200 in order to pressurize it to a therapeutic pressure (e.g., 6 cmH2O above ambient air pressure). In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material. The seal-forming structure 3100 can create a seal with the patient's face in order to maintain the therapeutic pressure within the plenum chamber 3200, and limit leaks of the pressurized air to the ambient.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

In certain forms of the present technology, the plenum chamber 3200 comprises a cushion module. The cushion module comprising a shell. In some examples of the technology the cushion module is directly connectable to a headgear connection member or connection portion as described herein. The headgear connection member or connection portion may comprise a magnetic catch component. The headgear connection member or connection portion may connect directly to the shell of the cushion module by the magnetic catch mechanism. The magnetic catch mechanism comprises a first component which is part of the connecting portion or connecting member, as discussed herein, and a second component which is part of the cushion module. The first component and second component comprise magnet(s) and/or one of the components comprises a magnetically attractive material, for instance steel. In some examples the second component is integrated into the rigid or flexible shell of the cushion module. The magnet or magnetically attractive material may be moulded into the shell. Alternatively, the magnet or magnetically attractive material may be bonded to the shell. The magnetic catch may also include other mechanical features to enhance engagement and complement the magnetic attraction. An advantage of having the headgear connection integrated directly into the cushion module is a reduction in parts, as a separate frame component to connect the headgear with the plenum chamber is no longer necessary. This may make the patient interface easier to use, easier to clean and/or less costly to manufacture.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion. The material used to construct the positioning and stabilizing structure 3300 may have stretch capabilities in order to adjust to different patient's head sizes. This is described in AU 2019902270, which is incorporated by reference herein in its entirety.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap.

In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.3.1 Two-Point Connection Headgear

In one example of the present technology, the positioning and stabilising structure 3300 comprises a headgear formed of multiple headgear strap portions. FIGS. 7 to 14 show the headgear according to one example of the present technology. The headgear comprises a superior strap portion 3301. The superior strap portion 3301 may be configured to overlie the parietal bone of the patient's skull. The headgear further comprises an inferior strap portion 3302. The inferior strap portion 3302 may be configured to overlie the occipital bone of the patient's skull. The superior strap portion 3301 and the inferior strap portion 3302 are connected to at least one anterior strap portion 3303. The superior strap portion 3301 and the inferior strap portion 3302 join the anterior strap portion 3303 anterior to the patient's ear, in use. In the embodiment shown the headgear comprises two anterior strap portions 3303, one on each of the left and right side of the patient's skull. The two anterior strap portions 3303 are each formed integrally with one end of the superior strap portion 3301 and one end of the inferior strap portion 3302.

Each anterior strap portion 3303 is connected or connectable to a connection portion 3306 which engages an interfacing portion 3500 of the patient interface 3000. In the embodiment shown in FIGS. 7 to 14 the interfacing portion 3500 comprises an ultra-compact full-face mask, which is configured to seal with the mouth and the nose of the patient. The ultra-compact full-face mask seals under the nose to the nares of the patient. In other embodiments the interfacing portion 3500 may comprise a full-face mask or other mask configured to create a seal with the patient's airways and provide a flow of air. The seal-forming structure of the full-face mask forms a seal with the nasal bridge of the patient.

In the embodiment shown the anterior strap portion 3303 comprises a strap receiving portion 3304 and a strap attachment portion 3305 (as can be seen in FIG. 14). The strap attachment portion 3305 is releasably connectable to the strap receiving portion 3304 such that the anterior strap portion 3303 forms a loop. The loop engages the connection portion 3306 which engages the interfacing portion 3500. In some forms of the technology the connection portion 3306 forms part of the interfacing portion 3500. The strap receiving portion 3304 is configured to engage the strap attachment portion 3305 in a selected one of a plurality of possible positions. Each one of the plurality of possible positions is entirely on the strap receiving portion. In other words, the strap attachment portion 3305 is entirely within a boundary of the strap receiving portion 3304 while engaged to the strap attachment portion 3305. The strap attachment portion 3305 is sufficiently wide to allow for a wide range of adjustments, and also limit contact between the strap attachment portion 3305 and the patient's skin (e.g., the patient's cheek). The strap attachment portion 3305 may have a rough and/or abrasive surface and the width of the strap receiving portion may allow for multiple adjustment positions without the strap attachment portion 3305 extending outside of the boundary of the strap receiving portion 3304. The plurality of possible positions comprises a plurality of possible angular positions of the strap attachment portion 3305 relative to the strap receiving portion 3304. Engaging the strap attachment portion 3305 in one of the plurality of angular positions forms an angle between a first and second part of a bottom edge of the anterior strap portion loop. For example, a bottom edge of the strap attachment portion 3305 may be displaced from a bottom edge of the strap receiving portion 3304 so that the two bottom edges are not collinear. In any of the plurality of angular positions, bottom edge of the strap attachment portion 3305 remains more superior than the bottom edge of the strap receiving portion 3304. The possible positions can vary from each other in both the superior-inferior and the anterior-posterior directions.

By varying which of the plurality of possible positions on the strap receiving portion 3304 to engage the strap attachment portion 3305 with, the patient can adjust the direction and/or magnitude of the headgear vector. The phrase "headgear vector" is used herein to denote the magnitude and direction of the force applied by the headgear to the interfacing portion 3500. In the embodiment shown in FIGS. 7 to 14 the headgear vector is applied by the anterior strap portion loops to the connection portions 3306. In general, adjusting the position of the strap attachment portion 3305 in the superior-inferior direction will adjust the direction of the headgear vector. Adjusting the position of the strap attachment portion 3305 in the anterior-posterior direction will adjust the magnitude of the headgear vector by increasing or decreasing the size of the anterior strap portion loop. Increasing the size of the anterior strap portion loop increases the magnitude of the force applied by the headgear. Similarly, decreasing the size of the anterior strap portion loop decreases the magnitude of the force applied by the headgear.

The width W of the strap receiving portion 3304 (see arrow W of FIG. 11), decreases from a posterior end to an anterior end thereof. The widest portion of the strap receiving portion 3304 is substantially wider than the width of the strap attachment portion 3305 (e.g., two, three, or four times wider). The superior and inferior strap portions 3301, 3302 join the strap receiving portion 3304 adjacent the wider posterior end of the strap receiving portion 3304. In other words, the superior and inferior strap portions 3301, 3302 join the strap receiving portion 3304 posterior to the widest width W. The superior and inferior strap portions 3301, 3302 may continue to increase in width more posterior to the widest width W (e.g., the widest width W of the strap receiving portion 3304 may not be the widest portion of the positioning and stabilizing structure 3300). In the embodiment shown in FIGS. 7 to 14 the posterior end of the strap receiving portion 3304 has a generally triangular surface. One side of the triangular surface is the widest width W, and the triangular surface narrows in the anterior direction toward the strap attachment portion 3305. The superior and inferior strap portions 3301, 3302 are connected to respective superior and inferior corners of the triangular posterior end of the strap receiving portion 3304. The anterior end of the strap receiving portion 3304 has a generally rectangular surface adjacent to the remaining corner of the triangular posterior end of the strap receiving portion 3304. The anterior end of the strap receiving portion 3304 may have a width approximately equivalent to the width of the strap attachment portion 3305. In some examples, the width of the anterior end may be equivalent to the width of the strap attachment portion 3305. In other examples, the width of the anterior end may be greater than the width of the strap attachment portion 3305. This may allow the strap attachment portion 3305 the ability to adjust to a greater plurality of angular positions while remaining within the boundaries of the strap receiving portion 3305.

The strap attachment portion 3305 may engage the posterior end of the strap receiving portion 3304 when in one or more of its possible positions. The posterior end of the strap receiving portion 3304 may overlie the cheek of the patient's face and preferably overlies the upper cheek region. The posterior end of the strap receiving portion 3304 is preferably relatively large, in some examples around 20 $cm^2$, to provide a large number of possible positions for engaging the strap attachment portion 3305 and therefore a greater range of possible headgear vectors. In other words, the area of the posterior end of the strap receiving portion 3304 is greater than the area of the strap attachment portion 3305, and can accommodate the strap attachment portion 3305 in a plurality of positions.

In the embodiment shown the strap attachment portion 3305 comprises a hook material. The strap receiving portion 3304 has a patient facing surface and an opposite non-patient facing surface. The non-patient facing surface is provided with an unbroken loop material to engage the hook material of the strap attachment portion 3305. In other embodiments the strap attachment portion 3305 may comprise an unbroken loop material that engages the non-patient facing surface of strap receiving portion 3304 which comprises a hook material.

In the embodiment shown the connection portion 3306 comprises a loop through which the anterior strap portion 3303 passes. In other embodiments (not shown) the connection portion 3306 may comprise a hook formation which the anterior strap portion loop can engage. In this way the anterior strap portion 3303 can be removed from the connection portion 3306 without removing the strap attachment portion 3305 from the strap receiving portion 3304. This may enable the strap attachment portion 3305 to maintain substantially the same position relative to the strap receiving portion 3304. Thus the anterior strap portion 3303 may be removed from and reattached to the connection portion 3306 without substantially altering a headgear force vector provided by the anterior strap portion 3303.

In some embodiments (not shown) the connection portion 3306 attaches to a frame which connects to the cushion module. In other embodiments the connection portion 3306 connects directly to the cushion module of the interfacing portion 3500. Preferably the connection portion 3306 connects by a removable connection. In some examples this may comprise a magnetic catch. In other examples the connection may be through a clip attachment. The anterior strap portion 3303 may be removed from the interfacing portion 3500 without removing the strap attachment portion 3305 from the strap receiving portion 3304. In other embodiments the connection portion 3306 is fixedly engaged to the frame or cushion module.

The ability to modify the direction and/or the magnitude of the headgear vector enables the patient to better create a seal between the seal-forming structure and the patient's face. As shown in FIGS. 8 and 9, the ultra-compact full-face mask may include separate sealing portions for the patient's nose and mouth. In other words, a portion of the plenum chamber 3200 seals under the patient's nose, and around the patient's mouth. In some examples, the portion of the seal-forming structure that seals under the patient's nose may be separate from the portion of the seal-forming structure that seals around the patient's mouth. In other words, the portion of the seal-forming structure that seals under the patient's nose may have a separate perimeter than the portion of the seal-forming structure that seals around the patient's mouth. In other examples, the single seal may seal under the patient's nose and around the patient's mouth, so that only a single seal portion is needed. This may provide a shorter total length needed to seal against the patient's face.

Generally, the upper seal-forming structure 3100 seals around a periphery of the patient's nose. Specifically, this may include contacting the patient's subnasale, the nasal ala proximate to the alar rims (e.g., around the opening to each nostril), and/or the nasolabial sulcus. As shown in FIG. 7-1, the sealing force $F_1$ associated with the upper seal-forming structure 3100 is directed in a superior and posterior direction. In other words, the sealing force is directed both in the superior direction (i.e., up and into the columella) and in the posterior direction (i.e., into the lip superior and nasolabial sulcus), and into the patient's head.

Generally, the lower seal-forming structure 3100 seals around a periphery of the patient's mouth. Specifically, this may include contacting the patient's lip superior and/or lip inferior, around an area that is wider than the patient's mouth width. In other words, the lower seal-forming structure 3100 seals radially outside of the patient's cheilion, or corner of mouth region. As shown in FIG. 7-1, the sealing force $F_2$ associated with the lower seal-forming structure is directed in the posterior direction only. In other words, the sealing force associated with the patient's mouth is ideally directed straight into their head, and does not deviate in the inferior/superior direction.

The anterior strap portion 3303 determines a resultant force $F_R$ that will act on the seal-forming structure 3100 as a whole. Changing the direction of the resultant force $F_R$ applied by the headgear (e.g., changing the position of the strap attachment portion 3305 relative to the strap receiving portion 3304) may provide different magnitudes of force to both of these sections (i.e., under the patient's nose and around the patient's mouth). This may allow the patient to selectively adjust the sealing force in these two areas. In other words, the patient may be able to increase the sealing force around their mouth without substantially increasing the sealing force around their nose, in order to provide improved sealing without decreasing comfort. For example, the resultant force $F_R$ will be angled with respect to a generally horizontal axis (e.g., the Frankfort horizontal). The angle with respect to this axis is small when the strap attachment portion 3305 is coupled to the strap receiving portion 3304 proximate to the lower edge of the anterior strap portion 3303 (see e.g., solid strap in FIG. 11). The angle increases as the strap attachment portion 3305 is coupled to the strap receiving portion 3304 closer to the upper edge of the anterior strap portion (see e.g., dashed strap in FIG. 11).

The strap attachment portion 3305 is adjusted by the patient so that it is ideally neither completely horizontal (i.e., only in the posterior direction) nor completely vertical (i.e., only in the superior direction). This way a component of the resultant force $F_R$ will be directed in both the posterior and superior directions, so that the seal-forming structure 3100 will have component forces in both directions (e.g., in order to help seal against both the nose and mouth). In some examples, the headgear may be positioned so that the strap attachment portion 3305 extends below the horizontal when coupled to the strap receiving portion 3304, so that a component of the resultant force $F_R$ is directed in the inferior direction instead of the superior direction.

The connection portion 3306 may be rotationally fixed relative to the interfacing portion 3500 when the two are couple together. The cushion module (i.e., the seal-forming structure 3100 and/or the plenum chamber 3200) and the connection portion 3306 may therefore move together when the position of the strap attachment portion 3305 changes. If the strap attachment portion 3305 is attached substantially parallel to or at a relatively small angle relative to the inferior strap portion 3302 the cushion module will pivot such that the superior portion of the cushion module moves in the posterior direction. For example, this may occur if the bottom edge of the strap attachment portion 3305 is collinear with or within approximately 5° from a bottom edge of the inferior strap portion 3302 and/or the bottom edge of the strap receiving portion 3304. This may allow the patient to apply a greater sealing force in the posterior direction. In other words, the posterior component of force increases as the strap attachment portion 3305 becomes more collinear with the bottom edge of the inferior strap portion 3302, which in turn decreases the superior component. For the same magnitude, a greater proportion of the resultant force $F_R$ is directed in the posterior direction. Thus, the patient will fell a greater force against their lip superior, lip inferior, and/or nasolabial sulcus, as compared to their subnasale and/or columella.

If the strap attachment portion 3305 is attached at a larger angle, for example aligned with the superior strap portion 3301, this causes the cushion module to pivot such that the superior portion of the cushion module moves in the anterior direction. For example, this may occur if a top edge of the strap attachment portion 3305 is collinear with or within approximately 5° from a top edge of the superior strap portion 3301 and/or a top edge of the strap receiving portion 3304. This may allow the patient to apply a greater sealing force in the superior direction. In other words, the superior component of force increases as the strap attachment portion 3305 becomes less collinear with the bottom edge of the inferior strap portion 3302, which in turn decreases the posterior component. For the same magnitude, a greater proportion of the resultant force $F_R$ is directed in the superior direction. Thus, the patient will fell a greater force against their subnasale and/or columella, as compared to their lip superior, lip inferior, and/or nasolabial sulcus.

By adjusting the position of the strap attachment portion(s) 3305 the patient can achieve personalised sealing forces optimised for seal, stability and comfort. Some patient's may be able to tolerate a greater force on their subnasale and/or columella, and may therefore achieve a better seal around their nares, although potentially at the expense of the seal around their mouth. Conversely, some patient's may be able to tolerate less force on their subnasale and/or columella, and may therefore achieve a better seal around their mouth, although potentially at the expense of the seal around their nares. In either situation described above, decreasing the force around one of the orifices (i.e., the nose or the mouth), will not decrease the sealing force enough that the air within the plenum chamber 3200 can leak out into the ambient. However, increasing the sealing force in one location may increase, decrease, or keep constant the sealing force in the other location. For example, if only the angle changes and the magnitude remains the same, then increasing the force in one location (e.g., the mouth) would decrease the sealing at the other location (e.g., the nose). However, if both the magnitude and the angle are adjusted, then the sealing forces may increase, decrease, or stay the same at each respective location (i.e., proximate to the nose and mouth).

The superior strap portion 3301 and inferior strap portion 3302 may be adjustable, for instance by means of a buckle (not shown) configured to change the length of the respective portion, or through having a portion formed from an elastic material.

In another embodiment (not shown) the superior strap portion 3301 bifurcates into a first strap portion which overlies a superior surface of the patient's parietal bone and a second strap portion which overlies a posterior surface of the patient's parietal bone. The first and second strap portions may re-join on the opposite side of the patient's head to form a single strap portion. In some embodiments, the first and second strap portions have a smaller width than the superior strap portion 3301. Bifurcating the superior strap portion 3301 into first and second strap portions may assist the headgear in achieving stability of the patient interface 3000.

In the embodiment shown in FIGS. 7 to 14, the superior strap portion 3301 is joined to the inferior strap portion 3302 by posterior connecting strap portions 3310. In one example the superior strap portion 3301 and the posterior connecting strap portions 3310 form a substantially loop shape. In other embodiments the crown portion of the superior strap portion 3301 may join with the posterior connecting strap portions 3310 to form a substantially loop shape while lateral portions of the superior strap portion 3301, which lie against lateral surfaces of the patient's head, still connect to the anterior strap portion 3303. In some examples parts of the inferior strap portion 3302 also form part of the substantially loop shape.

In some embodiments (not shown) the headgear may comprise more than two anterior strap portions 3303. In alternate embodiments the anterior strap portion 3303 may be connected to only one of the superior or inferior strap portions 3301, 3302. The anterior strap may connect to an alternative strap or straps that form part of the headgear. The two-point headgear therefore increases modularity. Many different headgear styles are possible. There are a plurality of different headgear designs that can include the anterior strap portions 3303 with the strap receiving and strap attachment portions 3304, 3305 and the plurality of possible positions. Additionally, as long as the interfacing portion 3500 includes suitable connection portions 3306 then the patient can choose the most comfortable or stable headgear from the different headgear styles.

In some embodiments the entire headgear may be formed from a single piece of material rather than separate pieces stitched or otherwise joined together.

A benefit of having a two-point headgear connection whilst maintaining control of both the magnitude and direction of the headgear vector is that the patient may only need to adjust the two anterior strap portions 3303, rather than needing to adjust four connection points, as is common with many examples of prior art headgear. Changing the direction of the headgear vector is also easier since it only requires adjustment of the position of the strap attachment portion 3305 (e.g., changing the strap attachment portion 3305 between the plurality of angular positions). Many examples of prior art headgear require adjustment of both upper/superior and lower/inferior straps. The headgear of the present invention may therefore be easier to adjust. Additionally, if connecting portions are used that are releasably engageable with the interfacing portion 3500 then only initial setup may be required. Once adjusted, the headgear can be removed from the mask and so the patient can easily don and doff the patient interface 3000 without readjusting the headgear strap portions.

In some embodiments, the anterior strap portions 3303 may be made from a different textile to the remainder of the headgear, for instance with different patterns or textures to improve the aesthetics of the headgear. The anterior strap portions 3303 provide an increased textile region for the implementation of cosmetic features. These may be customisable to the patient. An improved aesthetic of the headgear may lead to improved compliance with the therapy.

The two-point headgear is less complicated than many examples of prior art headgear, and requires only two pieces of hook material and two connector portions. This may lead to an improved manufacturability and may result in easier, quicker, and/or cheaper manufacture of the headgear. The two-point headgear connection to the interfacing portion 3500 may also improve the manufacture of the interfacing portion 3500, as the interfacing portion 3500 will only require the capability to attach to two connection portions 3306. This will lead to a less complicated design and may result in easier, quicker, and/or cheaper manufacture of the headgear.

5.3.4 Connection Member

FIGS. 15 to 30 show a further embodiment of the present technology comprising a connection member 3800 for a patient interface 3000. FIGS. 15 to 22 show the connection member 3800. FIGS. 23 to 30 show the connection member 3800 connected to the right side of a full-face mask of the patient interface 3000. The left side of the full-face mask is also configured to receive a second connection member 3800 (not shown). The connection member 3800 is configured to removably connect one side of a positioning and stabilising structure 3300 to a side of an interfacing portion 3500 of the patient interface 3000. The connection member 3800 is configured to engage at least two strap portions of a positioning and stabilising structure 3300 which comprises multiple headgear straps.

The connection member 3800 comprises strap connection portions for connection, in use, to two strap portions of the headgear. The connection member 3800 may comprise a superior strap connection portion 3801 for connection, in use, to a superior strap portion 3301 of the headgear. The connection member 3800 may also comprise an inferior strap connection portion 3802 for connection, in use, to an inferior strap portion 3302 of the positioning and stabilising structure. In the embodiment shown the connection member 3800 comprises a single superior strap connection portion 3801 and a single inferior strap connection portion 3802. The superior strap connection portion 3801 is located superior to the inferior strap connection portion 3802.

In the embodiment shown in FIGS. 15 to 30, the superior strap connection portion 3801 comprises a first loop 3803 configured to receive an end of the superior strap portion 3301. The first loop 3803 is substantially rectangular. In use an anterior end of a superior strap portion 3301 is threaded through the aperture created by the first loop 3803 and then removably attached (for example by a hook and loop attachment) to a posterior end of the superior strap portion 3301 to create a superior strap portion loop. Similarly, the inferior strap connection portion 3802 comprises a second loop 3804 configured to receive an end of the inferior strap portion. The second loop 3804 is also substantially rectangular. An anterior end of the inferior strap portion 3302 is threaded through the aperture created by the second loop 3804 and then removably attached to a posterior end of the inferior strap portion 3302 to create an inferior strap portion loop.

In an alternative embodiment (not shown) the superior strap connection portion 3801 may comprise a first hook configured to receive an end of the superior strap portion 3301. An anterior end of the superior strap portion 3301 may be passed around the first hook and then removably attached onto a posterior end of the superior strap portion 3301 to form a superior strap portion 3301 loop. The superior strap portion 3301 loop may be able to engage and disengage the first hook without detaching the anterior end of the superior strap portion 3301 from the posterior end. The inferior strap connection portion 3802 may comprise a second hook configured to receive an end of the inferior strap portion 3302. As described above for the superior strap portion 3301, an anterior end of the inferior strap portion 3302 may be passed around the second hook and removably attached onto a posterior end of the inferior strap portion 3302 to form an inferior strap portion loop. The inferior strap portion loop may be able to engage and disengage the second hook without detaching the anterior end of the inferior strap portion from the posterior end.

The connection member 3800 further comprises an interface connection portion 3805 configured to removably connect to the interfacing portion 3500. The interface connection portion 3805 may be located inferior to the superior strap connection portion 3801. The interface connection portion 3805 may also be located superior to the inferior strap connection portion 3802. The interface connection portion 3805 may be movably coupled to the remainder of the connection member 3800 (e.g., the superior strap connection portion 3801 and the inferior strap connection portion 3802).

The interface connection portion 3805 and the interfacing portion 3500 may be configured to prevent or limit rotation of the interface connection portion 3805 relative to the interfacing portion 3500 when the patient interface 3000 is in use. In other words, the connection member 3800 may be unable to rotate as one piece, while connected to the interfacing portion 3500. For example, one or more mechanical features may be provided that mechanically engage the connection member 3800 to the interfacing portion 3500. The interface connection portion 3805 or the interfacing portion 3500 may comprise one or more lugs which fit into corresponding notches on the other portion. The mechanical features may lock the connection member 3800 in a predetermined orientation with respect to the interfacing portion 3500 when the two parts are engaged. Fixing the position of the connection member 3800 with respect to the interfacing portion 3500 may provide a better transfer of forces from the headgear strap portions to the interfacing portion 3500, thereby improving stability and seal. In the embodiment shown in the FIGS. 23 to 30, the interfacing connection member 3800 comprises a bearing formation 3806. The bearing formation 3806 is configured to engage a complementary bearing formation 3560 of the interfacing portion 3500. The engagement between the first bearing formation 3806 and the second bearing formation 3560 limits rotation of the connection member 3800 relative to the interfacing portion 3500 around a substantially horizontal axis of rotation when in use. A similar bearing arrangement may be used with the connection portions 3306 of FIGS. 7 to 14. In other examples, engagement between the first and second bearing formations 3806, 3560 may limit rotation of the connection member 3800 relative to the interfacing portion 3500 around a substantially vertical axis of rotation when in use.

The connection member 3800 may connect to the interfacing portion 3500 by a variety of different connection means, for example a clip or magnetic catch. In the embodiment shown in FIGS. 15 to 30 a magnetic catch connects the interface connection portion 3805 and the interfacing portion 3500. A first component 3807 of the magnetic catch is part of the interface connection portion 3805 and a second component 3550 (shown in FIGS. 26 to 30) of the magnetic catch is part of the interfacing portion 3500. The second component 3550 of the magnetic catch may be overmoulded or bonded to the interfacing portion 3500. The first component 3807 of the magnetic catch may comprise a protrusion 3808 (see FIG. 16) that fits into slot 3551 of the second component 3550 of the magnetic catch. The protrusion 3808 may be integrally formed from the interface connection portion 3805. In the embodiment shown, the protrusion 3808 is cylindrical in shape and protrudes from a surface of the interface connection portion 3805. The slot 3551 is generally rectangular but may have rounded ends. The protrusion 3808 may assist in ensuring that the two components of the magnetic catch are correctly aligned when the catch is in use. In some examples, the protrusion 3808 may be non-uniformly shaped, so that it cannot be inserted into the slot 3551 in all orientations. The non-uniform shape of the protrusion 3808 may further assist in limiting rotation of the connection portion 3800 relative to the interfacing portion 3500. The non-uniform shape may also assist the patient in properly positioning the connection portion 3800 (e.g., so that the superior and inferior strap connection portions 3801, 3802 extend in a posterior direction).

The magnetic catch may comprise one or more magnets as one of the first 3807 or second 3550 components and either another magnet or a piece of magnetically attractive material (for example steel) as the other component. The first 3807 and second 3550 component of the magnetic catch are therefore removably attached to each other by the attraction of the magnets. Preferably, the magnets are of a suitable strength to allow a user to easily disengage the catch whilst also preventing unintentional disengagement during the patient's sleep. In the embodiment shown the magnet(s) and/or magnetically attractive material are not shown in the figures. First recess 3809 in the first component 3808 and second recess 3552 (shown in FIG. 30) in the second component 3550 are configured to receive the magnet(s) and/or magnetically attractive material.

In other examples (not shown) the magnet is cylindrical in shape and protrudes from the surface of the interface connection portion 3805. The magnet engages with a corresponding notch on a surface of the interfacing portion 3500. The notch contains or is adjacent a piece of magnetically attractive material or another magnet to engage the first magnet. In such cases an additional protrusion of the magnetic catch may not be required.

In other examples the magnet may be embedded in a lug protruding from the surface of either the interface connection portion 3805 or the interfacing portion 3500, and may be configured to engage with a corresponding notch in the other portion. In other examples the magnet or the lug may have a different shape such as cuboidal. These shapes may limit the rotation of the connection member 3800 with respect to the interfacing portion 3500.

The magnetic catch may comprise other mechanical features which also lock the connection member 3800 to the interfacing portion 3500. In these embodiments the first 3807 and second 3550 components may be embedded in the connection member 3800 and the interfacing portion 3500 and may only make contact on a single surface. In some examples multiple corresponding notches may be provided to receive the lugs or magnets. This may allow for variability in the position of the connection member 3800 with respect to the interfacing portion 3500 and therefore a more customised fit for the patient.

In embodiments such as that shown in FIGS. 23 to 30, the interface connection portion 3805 is configured to connect to a frame 3580, the frame 3550 being configured to connect to the cushion module of the plenum chamber 3200. In some embodiments the interface connection portion 3805 is configured to connect to a shell of a cushion module of the patient interface 3000.

When the orientation of the connection member 3800 is constrained with respect to the interfacing portion 3500, adjustment of the headgear strap portions enables pivoting of the interfacing portion 3500, in particular the cushion module. For example, the connection member 3800 as a whole may be unable to pivot relative to the interfacing portion 3500. Tension in the superior and inferior strap portions 3801, 3802 therefore cause the connection member 3800, the interfacing portion 3500, and the cushion module to rotate as a single body. This enables a personalised fit for the patient 1000. The relationship between the two different forces applied to the connection member 3800 by the superior strap portion 3301 and the inferior strap portion 3302 of the headgear can enable pivoting of the cushion module. In one example tightening the superior strap portion 3301, thereby increasing the force applied by the superior strap portion 3301 to the interfacing portion 3500, without adjusting the inferior strap portion 3302, will cause the cushion to pivot such that the superior portion of the cushion (as well as the superior portions of the connection member 3800 and interfacing portion 3500) moves in a posterior direction. Similarly, tightening the inferior strap portion 3302, thereby increasing the force applied by the inferior strap portion 3302 to the interfacing portion 3500, without adjusting the superior strap portion 3301 will cause the cushion to pivot such that the inferior portion of the cushion (as well as the inferior portions of the connection member 3800 and interfacing portion 3500) moves in a posterior direction. The patient may therefore better be able to achieve a personalised fit by having a greater ability to customise sealing force vectors.

Unlike in the ultra-compact full-face mask as shown, for example, in FIG. 8, cushion of the full-face mask of FIGS. 23-30 does not include separate seal portions for the patient's nose and mouth. In other words, a single seal is formed around the patient's nose and mouth (which could also be the case in some examples of an ultra-compact full face mask). The seal-forming structure 3100 may contact a ridge of the patient's nose, an area outside of the nasolabial sulcus, and the lip inferior, so that the patient's pronasale and mouth are within the plenum chamber 3200. Pivoting the cushion will not create a better sealing force around only one of the nose or the mouth, because this sealing force applies to both orifices (i.e., increasing the strength of the seal proximate the patient's nose also increases the seal around the patient's mouth). The pivoting in the full-face mask may specifically apply to comfort. For example, the patient may pivot the superior portion of the cushion in the anterior direction (e.g., by tightening only the lower strap) in order to relieve pressure against the patient's nose (e.g., against the ridge of the patient's nose). This may increase the force proximate to the patient's mouth (e.g., against the patient's lip inferior), where the patient may be tolerant of greater forces. In another example, the patient may pivot the superior portion of the cushion in the posterior direction (e.g., by tightening only the upper strap) in order to apply pressure against the patient's nose (e.g., against the ridge of the patient's nose). This may increase the force proximate to the patient's nose.

In some forms, pivoting of the full-face mask caused by adjusting the anterior strap portions 3303 may not may not substantially reduce the sealing force along any portion of the perimeter of the seal-forming structure 3100. Rather, a patient may adjust the length of any number (i.e., one, two, three, or four) of the anterior strap portions 3303 without affecting the position of any other anterior strap portions 3303. In other words, adjusting only one anterior strap 3303 per side will increase the sealing force proximate that respective region (e.g., proximate the mouth) without necessarily decreasing the sealing force at the other region (e.g., proximate the nose), because the position of the unadjusted anterior strap portions 3303 may not change. Only adjusting one set of anterior strap portions (e.g., the top straps or the bottom straps) may still increase the total overall sealing force throughout the full-face mask. This differs from what is shown in FIG. 7-1, where an angular adjustment of anterior strap portion 3303 may increase the sealing force around the nose, potentially at the expense of the sealing force around the mouth.

A patient may adjust the full-face mask of FIGS. 23-30 in order to maximize their comfort, without necessarily decreasing the sealing force of the seal-forming structure 3100. Patients may adjust the length of each anterior strap portion 3303 (e.g., and therefore the force applied by each anterior strap portion 3303) in order to sufficiently conform to their individual facial geometry. The patient may also be able to make finer adjustments (e.g., as compared to the examples shown in FIGS. 7-14).

The force applied by the superior and inferior strap portions 3301, 3302 to the interfacing portion 3500 may be adjusted by changing the size of the superior and inferior strap portion loops, for instance by adjusting where the anterior attachment ends of the strap portions attach to the posterior receiving end of the strap portions. Increasing the size of the superior strap portion loop will increase the magnitude of the force applied by the superior strap portion 3301 to the interfacing portion 3500. Similarly, decreasing the size of the superior strap portion loop will decrease the magnitude of the force applied by the superior strap portion 3301. The same applies for the inferior strap portion 3302.

In the embodiment shown the interface connection portion 3805 comprises an outwardly curved edge 3810 which is adapted to be gripped by the user when disconnecting the interface connection portion 3805 from interfacing portion 3500. The curved edge 3810 is provided to the anterior side of the interface connection portion 3805. The curved edge 3810 assists the patient to more easily lift-off the connection member 3800 and disconnect it from the interfacing portion 3500.

The connection member 3800 may be used on various styles of interfacing portions with different cushion modules including full-face masks, compact full-face masks, and ultra-compact full-face masks. The size of the connection member 3800 may vary depending on the type of mask it is configured to be used with. The distance between the superior strap connection portion 3801 and the inferior strap connection portion 3802 may also vary depending on the type and size of the mask it is configured to be used with. The connection member 3800 may also be configured to be used with existing four-point connection headgears.

A patient interface assembly may comprise an interfacing portion 3500, a positioning and stabilising structure 3300 comprising a superior strap portion 3301 and an inferior strap portion 3302 and two connection members 3800. Each of the connection members 3800 may be configured to receive a respective end of the superior strap portion 3301 and a respective end of the inferior strap portion 3302. Each of the connection members 3800 may also be configured to be removably attachable to a respective left or right hand side of the interfacing portion 3500.

A connection member 3800 such as that described above provides several advantages. The headgear straps may only need to be adjusted once during the initial fitting of the patient since the headgear can be removed without disconnecting the headgear from the interfacing portion 3500. This makes the patient interface 3000 easier and quicker to use for the patient. They are also able to replicate the best seal and stability once fitted properly. The headgear is easier and quicker to don and doff, particularly as the strap portions do not need tightening/loosening every time the mask is donned/doffed. The manufacture of the frame or the cushion module may also be easier and/or cheaper given there are only two-connection points required rather than a typical four-point connection. The connection member 3800 also enables a two-point headgear connection whilst maintaining the benefits of four-point connection headgear, for instance increased stability, better fit and increased adjustment range.

5.3.4.1 Modularity of Connection Member and Connection Portion

The interfacing portion 3500 may be configured to connect to various different connection members 3800 and/or connection portions 3306 as described herein. For instance, compatible magnetic catches may be present on different headgear connection members 3800 and/or connecting portions 3306 (e.g. by having the same first component 3807 of the magnetic catch) that are therefore able to connect to the same frame or cushion of the interfacing portion 3500 (i.e. the second component 3550 of the magnetic catch). Different types of headgear, for instance two-point headgear and four-point headgear, can therefore be used with the same mask. In other words, the mask may provide the same type of seal against the patient's face (e.g., a nose seal, a mouth seal, a nose-and-mouth seal, etc.) regardless of whether the connection members 3800 or the connecting portions 3306 are being used. Changing the connection members 3800 and/or connecting portions 3306 may only change headgear vectors that different types of headgear (e.g., associated with the connection members 3800 and/or the connecting portions 3306), but may not change where the vectors originate from. In other words, the same mask receives the connection members 3800 or the connecting portions 3306 in the same location, so force vectors applied by different styles of headgear generally originate from the same or substantially the same location (e.g., from a connection point).

An embodiment of the present technology comprises a patient interface system, the patient interface system comprising an interfacing portion 3500, a first headgear configured to removably connect to the interfacing portion 3500, and a second headgear configured to connect to the interfacing portion 3500. The first and second headgear may be two-point or four-point connection headgear. The first and/or second headgear may be in the form of one of the headgears described above. In some examples the patient interface system comprises at least one connection member 3800, connected to one side of the first and/or second headgear. There are preferably two connection members 3800, one connected to each side of the first and/or second headgear. The patient interface system may further comprise a connection portion 3306 configured to connect the first and/or second headgear to the interfacing portion 3500. The connection portion 3306 and the connection member 3800 are configured to removably connect to the interfacing portion 3500 at the same position (e.g., a connection point). A single magnet catch connects the connection portion 3306 and the connection member 3800 to the interfacing portion 3500, wherein a first component 3807 of the magnetic catch is part of the connection portion 3306 or the connection member 3800 and a second component 3550 of the magnetic catch is part of the interfacing portion 3500. The second component 3550 may be part of the frame of the interfacing portion 3500 or it may be part of the cushion, for instance the shell, of the interfacing portion 3500. The first component 3807 of the connection portion 3306 and the first component 3807 of the connection member 3800 are substantially the same size (e.g., same length, same diameter, etc.), so that either may couple to the second component 3550 with substantially the same fit.

In some examples, the first headgear and the second headgear extend toward generally the same position. For example, the first headgear and the second headgear each extend generally toward the connection point. Thus, the patient feels the straps of the first and second headgear in approximately the same place regardless of which headgear is connected to the interfacing portion 3500. In other words, the straps of both the first and second headgears may overlay the patient's cheek region and extend toward the patient's nasolabial sulcus, although the terminus of the straps may not be identical. For example, in a two-point connection system, the single strap on each side of the patient's head may extend toward one location of the interfacing portion 3500, while in a four-point connection system, a pair of straps one each side of the patient's head may extend toward two separate points that are each radially outside of the location in the two-point connection system. While the exact locations in the two-point and four-point connections differ, the straps on each generally extend toward the second component 3550, so that the origin of the headgear vectors are substantially the same.

There are a number of benefits to having an interfacing portion 3500 configured to connect to different headgears. These include improved modularity, which increases flexibility and variety in the way different headgear arrangements can be connected to the same cushion module. Another advantage may be improved usability. By allowing patients to change to a different headgear whilst keeping the same mask, the patient can trial different headgear options with the same mask to find one that provides the best comfort, stability and seal. When switching between different styles of headgear, the patient by be able to maintain the desired length adjustment (e.g., to deliver the desired sealing force) while the respective headgear is disconnected from the interfacing portion 3500. This allows the patient to easily reconnect the any style of headgear to the interfacing portion 3500, and not have to readjust the length of the respective straps. In other words, the headgear vector may be pre-set and maintained so that the same direction and magnitude of the force provided by the headgear is present after the headgear is reattached to the interfacing portion 3500. The ability to connect to different headgear may also allow for reduced face marks or sores. Headgear may sometimes cause face marking, especially with repeated use of the same headgear which contacts the patient's face in the same place. In one example, straps of different style headgear may extend toward the same position on the patient's face, but may not overlay exactly the same surface of the patient's cheek. The ability to change headgear without changing the whole mask enables patients to use different headgear which contacts the face at different positions thereby avoiding face marking in the same place on the face. A patient may repeatedly change (e.g., every other day, every other week, every other month, etc.) the style of headgear in order to reduce face marking. The headgears of the patient interface system may vary significantly (for example one being two-point connection headgear and one being four-point connection headgear, as described above), or they may vary less significantly, for example by having substantially the same configurations but varying such that one of the headgears touches an area of the patient's face which the other does not. For example, the area of the straps may be different from one headgear to another. In one form the location or presence of at least one strap portion of the second headgear is different to that of the first headgear.

Another benefit may be to use a single style of headgear (e.g., two-point, four-point, etc.) with a different style of mask. This may allow the patient to try out different styles of masks, while continuing to use a style of headgear that the patient finds comfortable. For example, when beginning the therapy, the patient may be given a mask that seals only around the patient's nostrils, and a mask that seals around the patient's nose and mouth. The patient may try the fit and comfort of each style mask, while continuing to use the same style of headgear. In some examples, the patient may be able to switch the headgear from a first style mask to a second style mask without having to adjust the headgear vector (e.g., reposition the strap attachment portion 3305 with respect to the strap receiving portion 3304) on the headgear. The patient is able to easily switch the preferred headgear between different masks, while maintaining the same headgear vector (e.g., sealing force). In other examples, a different headgear vector is necessary for a different style of mask. This is because the different styles of masks seal onto different locations of the patient's face. Different vectors are needed in order to provide a sufficient sealing force to the different seal areas associated with the different styles of masks. The interchangeable headgear still permits the patient to use a preferred style of headgear, while using different styles of masks.

5.3.4.2 Tailored Connection Member

In some embodiments the connection member 3800 may be tailored for the specific anthropometric data of the patient. The connection member 3800 has a number of directional variables that affect the fit and the forces on the mask. These include dimensions, relative spacing and orientations. For instance: the vertical position with respect to the interfacing portion 3500; lateral-medial position with respect to the interfacing portion 3500; anterior-posterior position with respect to the interfacing portion 3500; rotational orientation about a vertical axis; rotational orientation about a lateral-medial axis; rotational orientation about an anterior-posterior axis; and overall rotational orientation about the connection between the interface connection portion 3805 and the interfacing portion 3500, for instance the rotation about the magnetic catch.

In some embodiments the angle of the superior strap connection portion 3801 relative to the interface connection portion 3805 may be adjustable. Additionally, or alternatively, the angle of the inferior strap connection portion 3802 relative to the interface connection portion 3805 may be adjustable.

The connection member 3800 may be customisable to individual patients such that one or more of the variables are specific to the anthropometric data of the patient. This allows the connection member 3800 to be adapted to enable the best fit for comfort, stability and seal. In some examples the connection member 3800 is formed using additive manufacturing techniques (e.g. 3D printing) to produce a customised design specific to the anthropometric data of the patient. This may involve taking measurements of the patient, creating a model of the patient and running an analysis to optimize the best shape and size of the connection member 3800.

In other examples, the connection member 3800 is formed from a material which has the ability to retain a new shape after being heated and deformed into the new shape. In these embodiments the connection member 3800 is heated and bent to adjust the shape provide the best position for the patient. This may be done by a sleep technician when fitting the patient with the mask.

In other examples a range of different connection members 3800 are provided which include pre-defined options configured for different patient head shapes and sizes. The connection members 3800 may be different in size and shape and may each be configured to fit a different set of anthropometric data.

In other examples the connection member 3800 may include one or more ball and socket connections, as shown in the embodiment of FIGS. 15 to 30. The superior strap connection portion 3801 may be connected to the interface connection portion 3805 by a first ball and socket mechanism 3811. Similarly, the inferior strap connection portion 3802 may be connected to the interface connection portion 3805 by a second ball and socket mechanism 3812. The superior and inferior strap connection portions 3801, 3802 are therefore able to rotate with respect to the interfacing portion 3500. For example, the ball and socket mechanisms 3811, 3812 may allow the superior and inferior connection portions 3801, 3802 respectively to move (e.g., pivot) while the connection member 3800 is coupled to the interfacing portion 3500. The ball and socket mechanisms 3811, 3812 permit rotation even while the first and second bearing formations 3806, 3560 limit movement between the interface connection portion 3805 and the interfacing portion. Each ball and socket mechanism 3811, 3812 is also independent of the other ball and socket mechanism 3812, 3811, thus allowing the ball and socket mechanisms 3811, 3812 to have independent angular positions. In some examples the ball and socket mechanisms 3811, 3812 may be tight enough that they do not move in use but may be manually adjusted by the patient or clinician/technician. In other words, the ball and socket mechanisms 3811, 3812 may not be freely rotatable, and are instead retained in a particular position unless manually actuated by the patient or clinician/technician. For example, moving the strap attachment portion 3305 relative to the strap receiving portion 3304 may cause at least one of the ball and socket mechanisms 3811, 3812 to rotate. In other words, changing the angular position of the strap attachment portion 3305 with respect to the strap receiving portion 3304 changes the magnitude and direction of the headgear vector. The respective ball and socket mechanism 3811, 3812 rotates as the headgear vector changes so that the respective ball and socket mechanism 3811, 3812 is aligned with the headgear vector (e.g., a surface of the respective connection portion 3801, 3803 is orthogonal with respect to the headgear vector). In other examples, the patient or clinician/technician may adjust the rotational position of the ball and socket mechanisms 3811, 3812 prior to the strap attachment portion 3305 being coupled to the strap receiving portion 3304. In other words, a position of the ball and socket mechanisms 3811, 3812 can be adjusted in order to determine the direction of an eventual headgear vector. The strap attachment portion 3305 can be coupled to the strap receiving portion 3304 at a desired position in order to set the magnitude for the headgear vector.

Since the ball and socket mechanisms 3811, 3812 are independent of one another, the patient or clinician/technician may only actuate one or the other depending on the particular needs of the patient. In other examples, the ball and socket mechanisms 3811, 3812 may be rotatably coupled through the first bearing formation 3806 (e.g., the ball and socket mechanisms 3811, 3812 and the first bearing formation 3806 are rotatable together). When the first and second bearing formations 3806, 3560 are engaged, the ball and socket mechanisms 3806, 3560 are unable to rotate, thereby limiting adjustment of the superior and inferior connection portions 3801, 3802 while the connection member 3800 is coupled to the interfacing portion 3500 (e.g., so adjustment does not occur while the patient sleeps).

5.3.5 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.6 Decoupling Structure(s)

In one form the patient interface 3000 includes at least one decoupling structure, for example, a swivel or a ball and socket.

5.3.7 Connection Port

Connection port 3600 allows for connection to the air circuit 4170.

5.3.8 Forehead Support

In one form, the patient interface 3000 includes a forehead support 3700.

5.3.9 Anti-Asphyxia Valve

In one form, the patient interface 3000 includes an anti-asphyxia valve.

5.3.10 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT DEVICE

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components, including pneumatic components 4100, in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

5.4.1.4 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier 5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.7 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Anatomy 5.8.2.1 Anatomy of the Face (nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Nares (Nostrils): Approximately ellipsoidal apertures forming the entrance to the nasal cavity. The singular form of nares is naris (nostril). The nares are separated by the nasal septum.

5.8.2.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.3 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.4 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.4.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.4.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.4.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since $T2>T1$, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.4.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 Other Remarks

A portion of the disclosure of this patent document contains material which is subject to copyright protection.

The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 REFERENCE SIGNS LIST

1000 Patient
1100 Bed partner
3000 Patient interface
3100 Seal-forming structure
3200 Plenum chamber
3210 Chord
3220 Superior point
3230 Inferior point
3300 Positioning and stabilising structure
3301 Superior strap portion
3302 Inferior strap portion
3303 Anterior strap portion
3304 Strap receiving portion
3305 Strap attachment portion
3306 Connection portion
3310 Posterior connection strap portion
3400 Vent
3500 Interfacing portion
3550 Second component of the magnetic catch
3551 Slot
3552 Second recess
3560 Second bearing formation
3580 Frame
3600 Connection port
3700 Forehead support
3800 Connection member
3801 Superior strap connection portion
3802 Inferior strap connection portion
3803 First loop of the superior strap connection portion
3804 Second loop of the inferior strap connection portion
3805 Interface connection portion
3806 First bearing formation
3807 First component of magnetic catch
3808 Protrusion
3809 First recess
3810 Curved edge
3811 First ball and socket mechanism
3812 Second ball and socket mechanism
4000 RPT device
4010 External housing
4012 Upper portion
4014 Lower portion
4015 Panel(s)
4016 Chassis
4018 Handle

4020 Pneumatic block
4100 Pneumatic components
4110 Air filters
4112 Inlet air filter
4114 Outlet air filter
4120 Muffler
4122 Inlet muffler
4124 Outlet muffler
4140 Pressure generator
4142 Blower
4144 Brushless DC motor
4160 Anti-spill back valve
4170 Air circuit
4180 Supplemental oxygen
4200 Electrical components
4202 Printed Circuit Board Assembly (PCBA)
4210 Power Supply
4220 Input devices
4270 Transducers
5000 Humidifier
5002 Humidifier inlet
5004 Humidifier outlet
5006 Humidifier base
5110 Reservoir
5120 Conductive portion
5130 Humidifier reservoir dock
5135 Locking lever
5150 Water level indicator
5240 Heating element

The invention claimed is:

1. A patient interface comprising:

a plenum chamber pressurisable to a therapeutic pressure of at least 6 cm $H_2O$ above ambient air pressure, said plenum chamber including a plenum chamber inlet port sized and structured to receive a flow of air at a therapeutic pressure for breathing by a patient;

a seal-forming structure constructed and arranged to form a seal with a region of the patient's face surrounding an entrance to the patient's airways for sealed delivery of a flow of air at the therapeutic pressure of at least 6 cm $H_2O$ above ambient air pressure throughout the patient's respiratory cycle in use, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; and a positioning and stabilising structure for a patient interface, the positioning and stabilising structure comprising:

a superior strap portion;

an inferior strap portion;

at least one anterior strap portion connected to or formed integrally with the superior strap portion and the inferior strap portion;

wherein the at least one anterior strap portion comprises:

a strap receiving portion; and a strap attachment portion which is releasably connectable to the strap receiving portion such that the at least one anterior strap portion forms a loop, wherein in use the loop engages a connection portion which engages the plenum chamber;

wherein the strap receiving portion is configured to engage the strap attachment portion in a selected one of a plurality of possible positions, wherein the plurality of possible positions comprises a plurality of possible angular positions of the strap attachment portion relative to the strap receiving portion, and wherein the angle between the strap attachment portion and the strap receiving portion when connected is configured to cause pivotable movement in the plenum chamber and/or seal-forming structure.

2. The patient interface according to claim 1, wherein the superior strap portion and the inferior strap portion join the at least one anterior strap portion anterior to the patient's ear, in use.

3. The patient interface according to claim 1, wherein a width of the strap receiving portion decreases from a posterior end to an anterior end thereof, and wherein the width of the strap receiving portion is not narrower than the strap attachment portion between the posterior end and the anterior end.

4. The patient interface according to claim 1, wherein the strap attachment portion comprises a hook material.

5. The patient interface according to claim 4, wherein the strap receiving portion comprises a patient facing surface configured to face the patient and an opposite non-patient facing surface configured to face away from the patient, wherein the non-patient facing surface is provided with an unbroken loop material to engage the hook material of the strap attachment portion.

6. The patient interface according to claim 1, wherein a maximum width of the strap receiving portion is two to four times wider than the maximum width of the strap attachment portion.

7. The patient interface according to claim 1, wherein a superior portion of the plenum chamber and/or the seal-forming structure is configured to move in a posterior direction when the strap attachment portion is parallel to the inferior strap portion.

8. The patient interface according to claim 1, wherein a superior portion of the plenum chamber and/or the seal-forming structure is configured to move in an anterior direction when the strap attachment portion is aligned with the superior strap portion.

9. The patient interface according to claim 1, wherein the connection portion is releasably engageable via a magnet.

10. The patient interface according to claim 1, wherein the at least one anterior strap portion passes through a slot of the connection portion.

11. The patient interface according to claim 1, wherein the superior strap portion is configured to overlie the parietal bone of the patient's skull.

12. The patient interface according to claim 1, wherein the inferior strap portion is configured to overlie or lie inferior to the occipital bone of the patient's skull.

13. The patient interface according to claim 1, wherein the connection portion attaches to a frame which connects to a cushion module of the plenum chamber.

14. The patient interface according to claim 1, wherein the connection portion attaches to a cushion module of the plenum chamber.

15. The patient interface according to claim 1, wherein at least a part of the at least one anterior strap portion is configured to overlie a cheek area of the patient's face.

16. The patient interface according to claim 1, wherein the superior strap portion, inferior strap portion, and at least one anterior strap portion or portions are integrally formed from a single piece of material.

17. The patient interface according to claim 1, wherein the superior strap portion bifurcates into a first strap portion which overlies a superior surface of the patient's parietal bone and a second strap portion which overlies a posterior surface of the patient's parietal bone.

18. The patient interface according to claim 1, wherein the superior strap portion is joined to the inferior strap portion by posterior connecting strap portions.

19. The patient interface according to claim 18, wherein the superior strap portion and the posterior connecting strap portions form a substantially loop shape.

20. The patient interface according to claim 1, wherein the at least one anterior strap portion having a generally triangular surface with a first width and a second width being less than the first width and disposed more anterior than the first width while in use, the superior strap portion and the inferior strap portion each connected to or formed integrally with the at least one anterior strap portion at a respective corner of the generally triangular surface.

* * * * *